US012691234B2

(12) United States Patent
Confino et al.

(10) Patent No.: US 12,691,234 B2
(45) Date of Patent: Jul. 28, 2026

(54) METHODS EMPLOYING GASEOUS NITRIC OXIDE FOR INHIBITING TUMOR GROWTH

(71) Applicant: Beyond Air, Inc., Garden City (IL)

(72) Inventors: Hila Confino, Rehovot (IL); Steven A. Lisi, Garden City, NY (US); Rinat Kalaora, Rehovot (IL); Amir Avniel, Rehovot (IL)

(73) Assignee: Beyond Air, Inc., Garden City, NY (US)

( * ) Notice: Subject to any disclaimer, the term of this patent is extended or adjusted under 35 U.S.C. 154(b) by 852 days.

(21) Appl. No.: 17/779,709

(22) PCT Filed: Nov. 25, 2020

(86) PCT No.: PCT/IB2020/061150
§ 371 (c)(1),
(2) Date: May 25, 2022

(87) PCT Pub. No.: WO2021/105901
PCT Pub. Date: Jun. 3, 2021

(65) Prior Publication Data
US 2023/0338416 A1    Oct. 26, 2023

Related U.S. Application Data

(60) Provisional application No. 63/090,345, filed on Oct. 12, 2020, provisional application No. 63/027,120, filed on May 19, 2020, provisional application No. 62/985,611, filed on Mar. 5, 2020, provisional application No. 62/984,926, filed on Mar. 4, 2020, provisional application No. 62/982,817, filed on Feb. 28, 2020, provisional application No. 62/963,849, filed on Jan. 21, 2020, provisional application No. 62/939,975, filed on Nov. 25, 2019.

(51) Int. Cl.
| | |
|---|---|
| *A61K 33/00* | (2006.01) |
| *A61K 9/00* | (2006.01) |
| *A61K 39/00* | (2006.01) |
| *A61K 40/24* | (2025.01) |
| *A61M 13/00* | (2006.01) |
| *A61M 39/22* | (2006.01) |
| *A61P 35/00* | (2006.01) |

(52) U.S. Cl.
CPC ......... *A61M 13/003* (2013.01); *A61K 9/0019* (2013.01); *A61K 33/00* (2013.01); *A61K 39/0011* (2013.01); *A61K 40/24* (2025.01); *A61M 39/223* (2013.01); *A61P 35/00* (2018.01); *A61M 2202/0275* (2013.01); *A61M 2205/3334* (2013.01); *A61M 2205/3344* (2013.01); *A61M 2205/7536* (2013.01)

(58) Field of Classification Search
CPC ..... A61M 13/003; A61M 35/30; A61K 33/00; C12N 5/0693–0694
See application file for complete search history.

(56) References Cited

U.S. PATENT DOCUMENTS

| | | | |
|---|---|---|---|
| 5,345,928 | A | 9/1994 | Lindkvist |
| 5,873,359 | A | 2/1999 | Zapol et al. |
| 6,962,154 | B2 | 11/2005 | Krebs |
| 7,955,294 | B2 | 6/2011 | Stenzler et al. |
| 8,017,582 | B2 | 9/2011 | Shirwan et al. |
| 8,168,232 | B2 | 5/2012 | Graham et al. |
| 12,569,628 | B2 * | 3/2026 | Scholz ............... A61M 13/003 |
| 2002/0078958 | A1 | 6/2002 | Stenzler |
| 2002/0155164 | A1 | 10/2002 | Figley et al. |
| 2004/0258772 | A1 | 12/2004 | Otterbein |
| 2005/0004511 | A1 | 1/2005 | Figley et al. |
| 2005/0217679 | A1 | 10/2005 | Miller et al. |
| 2006/0290525 | A1 | 12/2006 | Andersen et al. |
| 2007/0275100 | A1 | 11/2007 | Miller |
| 2008/0193566 | A1 | 8/2008 | Miller et al. |
| 2009/0205655 | A1 | 8/2009 | Montgomery et al. |
| 2013/0239962 | A1 | 9/2013 | Goldstein |
| 2015/0320951 | A1 | 11/2015 | Acker et al. |
| 2017/0043115 | A1 | 2/2017 | Murphy et al. |
| 2018/0280654 | A1 | 10/2018 | Borrello |
| 2022/0111173 | A1 | 4/2022 | Lautner et al. |

FOREIGN PATENT DOCUMENTS

| | | |
|---|---|---|
| DE | 10306766 A1 | 8/2004 |
| WO | 2005110441 A2 | 11/2005 |
| WO | WO 2008/095311 | 8/2008 |

(Continued)

OTHER PUBLICATIONS

Wang et al. "Nitric Oxide Delivery System for Cell Culture Studies" Annals of Biomedical Engineering, vol. 31, pp. 65-79, 2003 (Year: 2003).*
Olson, S. Y, et al., "Abstract 5631: Nitric oxide-based immune response modifications: A novel paradigm in tumor vaccine development against melanoma", Can. Res., 51(8), Suppl., Apr. 1, 2010, 1 pg.
International Preliminary Report on Patentability Dated Jun. 9, 2022 From the International Bureau of WIPO Re. Application No. PCT/IB2020/061149. (8 Pages).
International Preliminary Report on Patentability Dated Jun. 9, 2022 From the International Bureau of WIPO Re. Application No. PCT/IB2020/061150. (15 Pages).
International Search Report and the Written Opinion Dated Jul. 9, 2021 From the International Searching Authority Re. Application No. PCT/IB2020/061150. (27 Pages).

(Continued)

*Primary Examiner* — Thane Underdahl
(74) *Attorney, Agent, or Firm* — Elmore Patent Law Group, P.C.; Joseph C. Zucchero; Carolyn S. Elmore

(57)    ABSTRACT

Methods of inhibiting growth of cells or tissue of a primary and/or secondary tumor, and/or of stimulating an immunological response to the tumor, in a subject in need thereof, and systems for performing same, are provided. The methods employ local administration of a gas, such as gaseous nitric oxide, typically at a high dose. Immune cells obtained upon treating a tumor with gaseous nitric oxide, either in vivo or ex vivo, and methods employing same are also provided.

17 Claims, 29 Drawing Sheets

(56) References Cited

FOREIGN PATENT DOCUMENTS

| WO | WO 2008/095312 | | 8/2008 | |
|----|----|----|----|----|
| WO | 2009023750 | A1 | 2/2009 | |
| WO | WO 2013/132500 | | 9/2013 | |
| WO | WO 2013/132503 | | 9/2013 | |
| WO | WO 2014/008490 | | 1/2014 | |
| WO | WO 2017/1055995 | | 7/2014 | |
| WO | 2016077635 | A1 | 5/2016 | |
| WO | WO 2016/168680 | | 10/2016 | |
| WO | 2019130117 | A1 | 7/2019 | |
| WO | WO 2021/105900 | | 6/2021 | |
| WO | WO 2021/105901 | | 6/2021 | |
| WO | WO-2021105900 | A1 * | 6/2021 | ............. A61K 40/24 |
| WO | 2022043931 | A2 | 3/2022 | |
| WO | 2022249104 | A1 | 12/2022 | |

OTHER PUBLICATIONS

International Search Report and the Written Opinion Dated May 12, 2021 From the International Searching Authority Re. Application No. PCT/IB2020/061149. (13 Pages).

Invitation to Pay Additional Fees Dated May 3, 2021 From the International Searching Authority Re. Application No. PCT/IB2020/061150. (2 Pages).

Official Action Dated Jun. 17, 2022 from US Patent and Trademark Office Re. U.S. Appl. No. 17/620,696. (13 pages).

Bonavida et al. "Nitric Oxide-Mediated Sensitization of Resistant Tumor Cells to Apoptosis by Chemo-Immunotherapeutics", Redox Biology, 6: 486-494, Available Online Aug. 18, 2015.

Confino et al. "Beyond Air® to Present New Nitric Oxide Data in an e-Poster Presentation at the North America Conference on Lung Cancer 2020 (NACLC 2020)", Globe News Wire, 7 P., Aug. 27, 2020.

Confino et al. "Gaseous Nitric Oxide at High Concentrations Is A Powerful Anti-Tumor Agent Both In-Vitro and In-Vivo", AACR, Poster, Jun. 2020.

Confino et al. "Nitric Oxide Lung Cancer Active Vaccination", 2020 North America Conference on Lung Cancer, #NACLC20, World-wide Virtual Event, Oct. 16-17, 2020, Slide Show, 14 P., Oct. 16, 2020.

Confino et al. "Nitric Oxide Tumor Ablation Stimulates An Anti-Tumor Immune Response in Mice", AACR, American Association for Cancer Research, AACR Virtual Special Conference on Tumor Immunology and Immunotherapy, Israel, Oct. 19-20, 2020, Power Point Presentation, 15 P., Oct. 19, 2020.

El-Naa et al. "Sildenafil Potentiates the Antitumor Activity of Cisplatin by Induction of Apoptosis and Inhibition of Proliferation and Angiogenesis", Drug Design, Development and Therapy, 10: 3661-3672, Published Online Nov. 16, 2016.

Huerta "Nitric Oxide for Cancer Therapy", Future Science, 1(1): FSO44-1-FSO44-9, Aug. 1, 2015.

Keisari et al. "Activation of Local and Systemic Anti-Tumor Immune Responses by Ablation of Solid Tumors With Intratumoral Electro-chemical or Alpha Radiation Treatments", Cancer Immunology, Immunotherapy, 63(1): 1-9, Published Online Aug. 17, 2014.

Knavel et al. "Tumor Ablation: Common Modalities and General Practices", Techniques in Vascular and Interventional Radiology, 16(4): 192-200, Dec. 2013.

Lin et al. "Non-Thermal Plasma as a Unique Delivery System of Short-Lived Reactive Oxygen and Nitrogen Species for Immuno-genic Cell Death in Melanoma Cells", Advanced Science, 6(6): 1802062-1-802062-15, Jan. 28, 2019.

Nath et al. "Nitric Oxide-Releasing Aspirin Suppresses NF-KB Signaling in Estrogen Receptor Negative Breast Cancer Cells In Vitro and In Vivo", Molecules, 20(7): 12481-12499, Jul. 9, 2015. 2015.

Ning et al. "Novel Nitric Oxide Generating Compound Glycidyl Nitrate Enhances the Therapeutic Efficacy of Chemotherapy and Radiotherapy", Biochemical and Biophysical Research Communi-cations, 447(3): 537-542, Available Online Apr. 13, 2014.

Rizi et al. "Nitric Oxide: The Forgotten Child of Tumor Metabo-lism", Trends in Cancer, 3(9): 659-672, Published Online Aug. 18, 2017.

Schairer et al. "The Potential of Nitric Oxide Releasing Therapies as Antimicrobial Agents", Virulence, 3(3): 271-279, Published Online May 1, 2012.

Seabra et al. "Nitric Oxide Donors for Prostate and Bladder Can-cers: Current State and Challenges", European Journal of Pharma-cology, 826: 158-168, Published Online Mar. 1, 2018.

Slovak et al. "Immuno-Thermal Ablations—Boosting the Antican-cer Immune Response", Journal for Immuno Therapy of Cancer, 5(1): 78-1-78-15, Oct. 17, 2017.

Srivatsan et al. "Allogeneic Tumor Cell Vaccines. The Promise and Limitations in Clinical Trials", Human Vaccines & Immunotherapeutics, 10(1): 52-63, Published Online Sep. 24, 2013.

Vannini et al. "The Dual Role of iNOS in Cancer", Redox Biology, 6: 334-343, Available Online Aug. 24, 2015.

Weyerbrock et al. "Growth Inhibition and Chemosensitization of Exogenous Nitric Oxide Released From NONOates in Glioma Cells In Vitro: Laboratory Investigation", Journal of Neurosurgery, 110(1): 128-136, Jan. 2009.

* cited by examiner

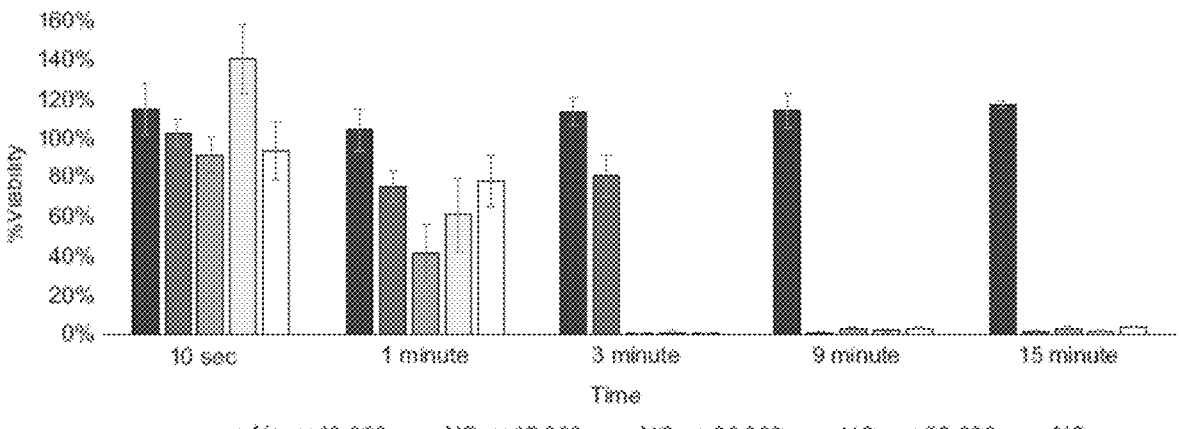
FIG. 7
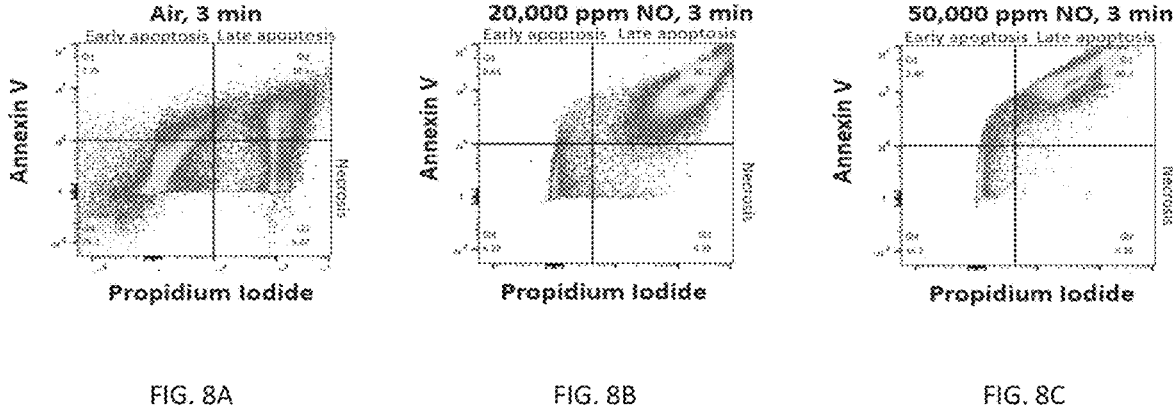
FIG. 8A                    FIG. 8B                    FIG. 8C

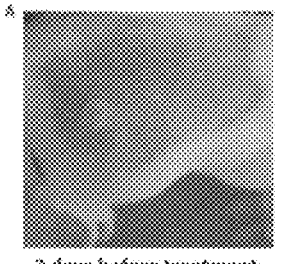
2 days before treatment
FIG. 10A
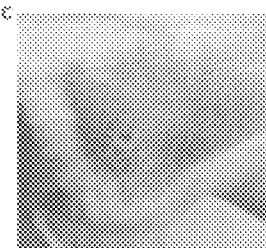
1 minute after treatment
FIG. 10B
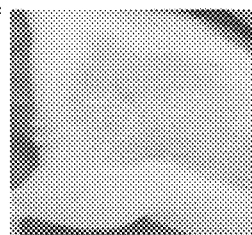
9 days after treatment
FIG. 10C
14 days after treatment
FIG. 10D
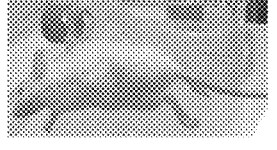
FIG. 10E
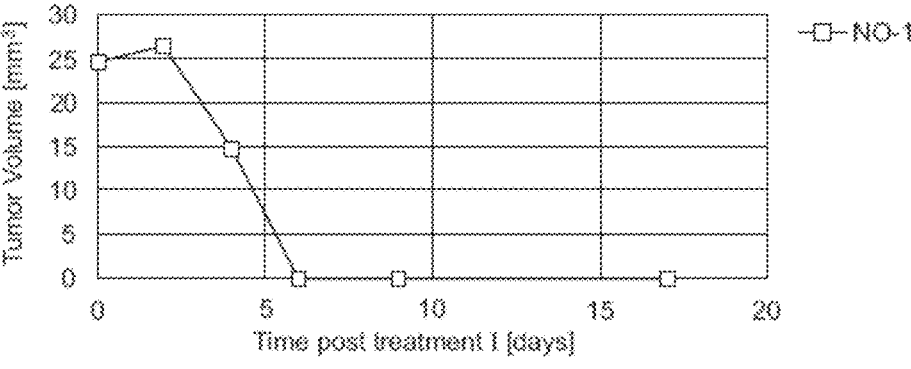
FIG. 10F

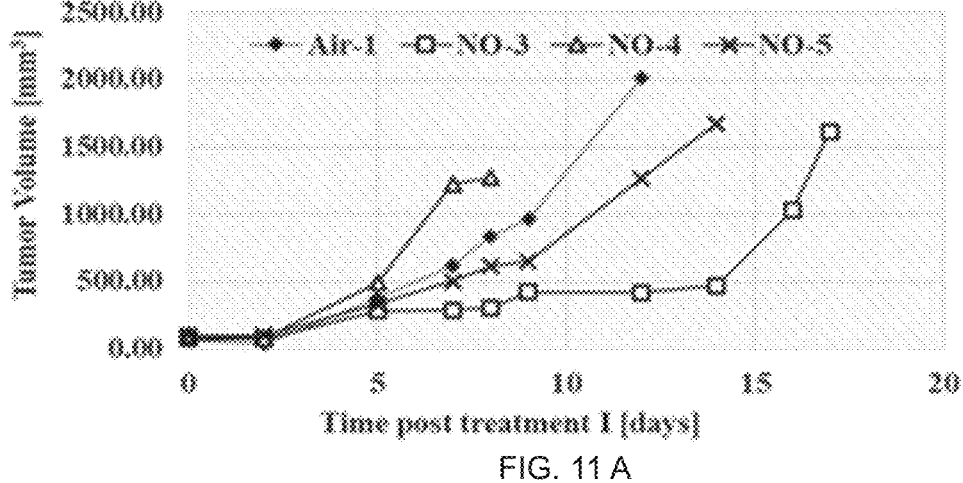
FIG. 11 A
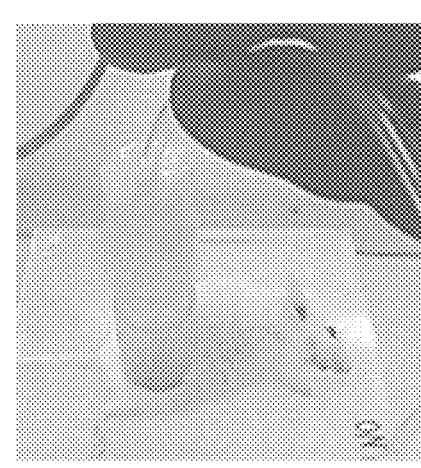
FIG. 11 B          FIG. 11 C

A.    50,000 ppm NO                    Air

Outside

B.    50,000 ppm NO                    Air

Inside

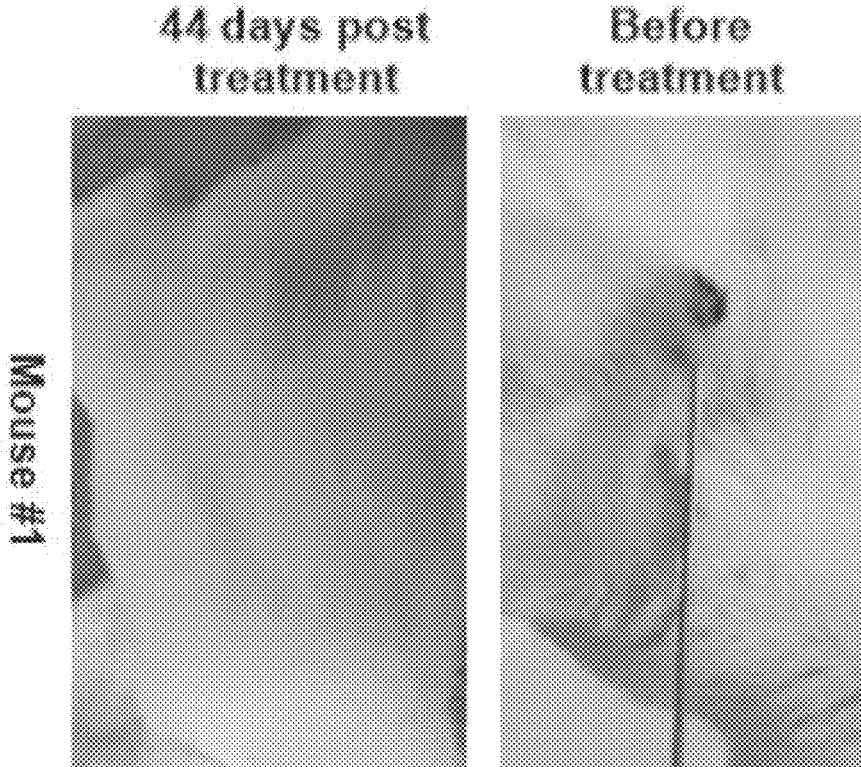
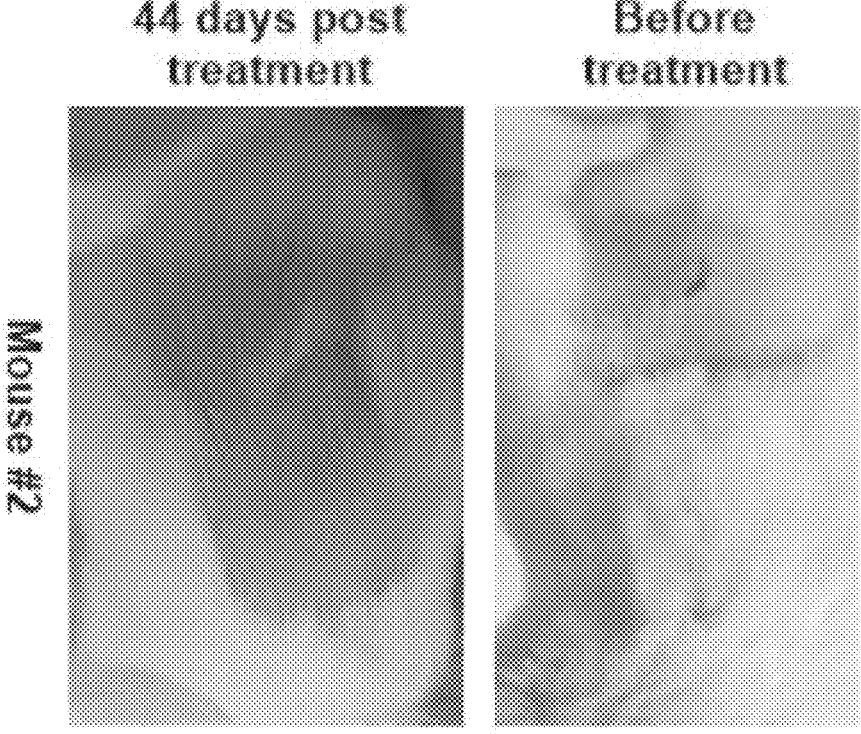
FIG. 13

Before NO gas treatment
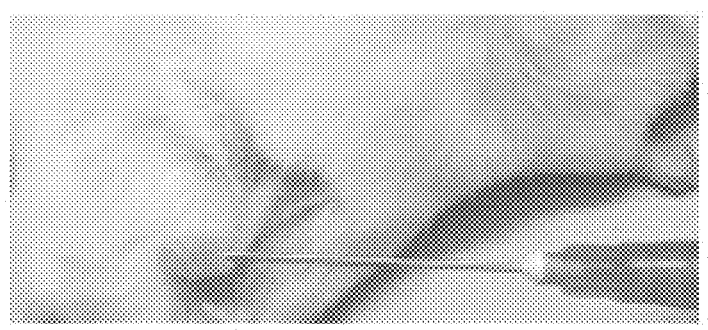
Nine days post treatment
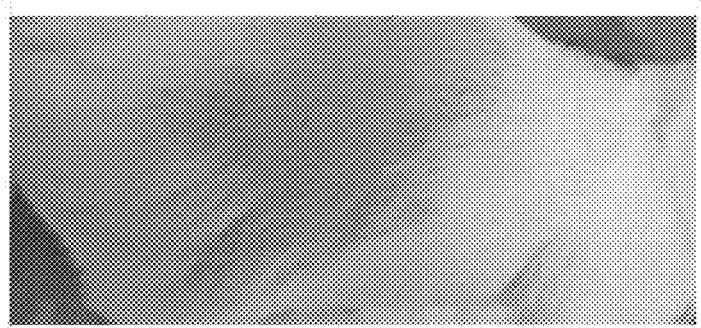
FIG. 14

| Day 0 | Day 7-14 | Day 11-25 | Follow-up |
|---|---|---|---|
| Tumor cell inoculation | Gaseous NO treatment | Challenge assay | Monitoring challenge tumor |

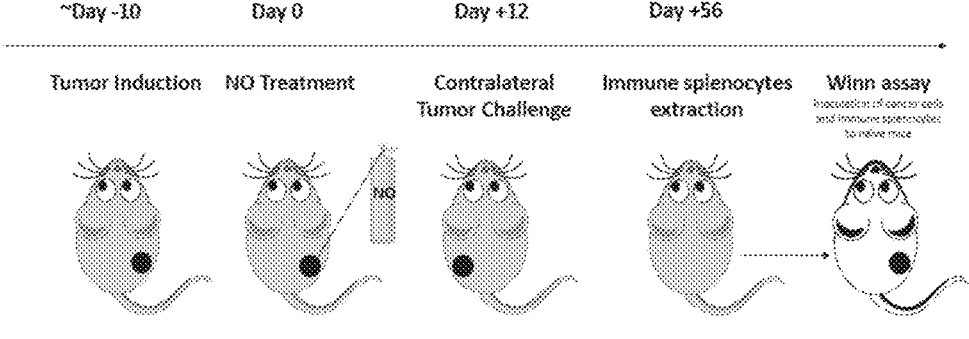
FIG. 18A
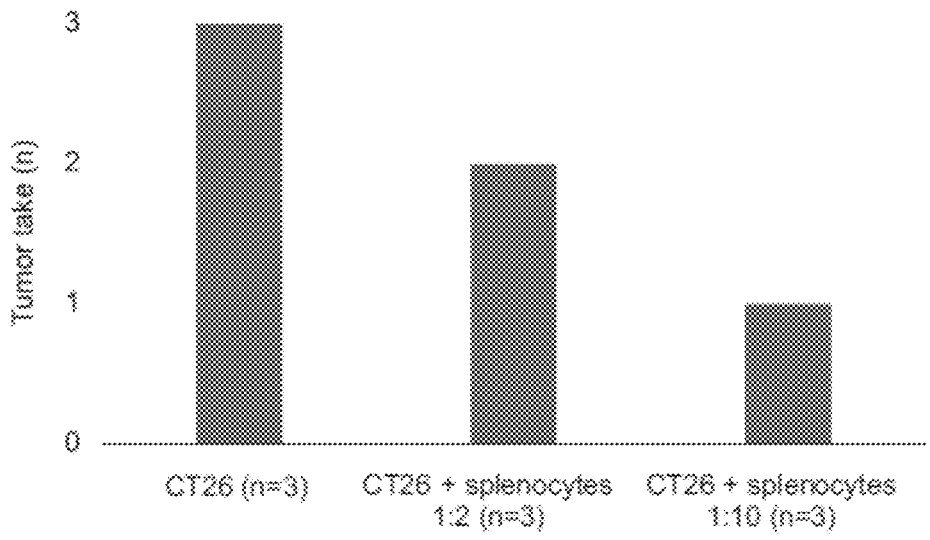
FIG. 18B
FIG. 18C

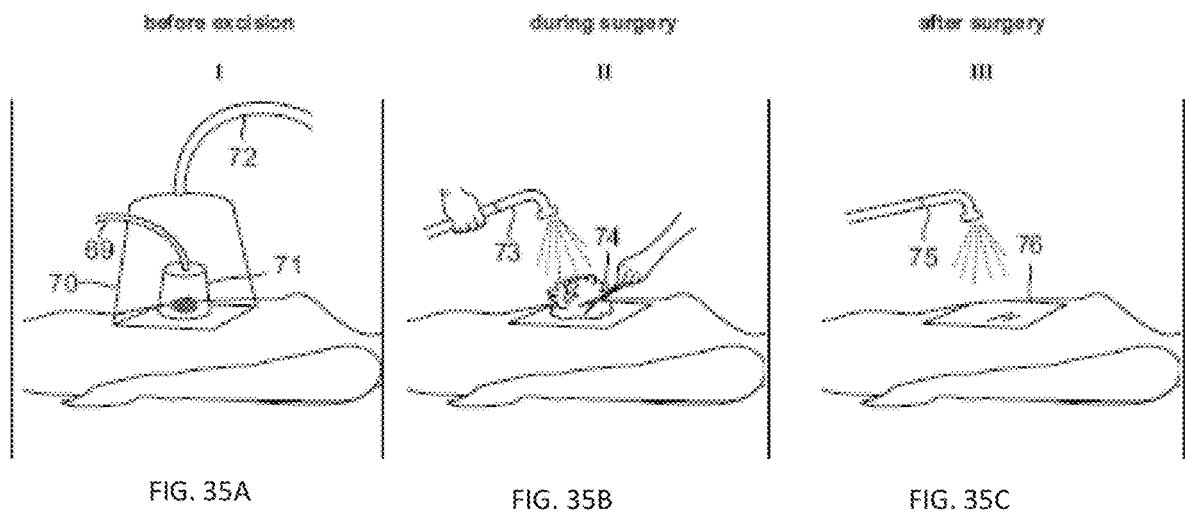
FIG. 35A                 FIG. 35B                 FIG. 35C
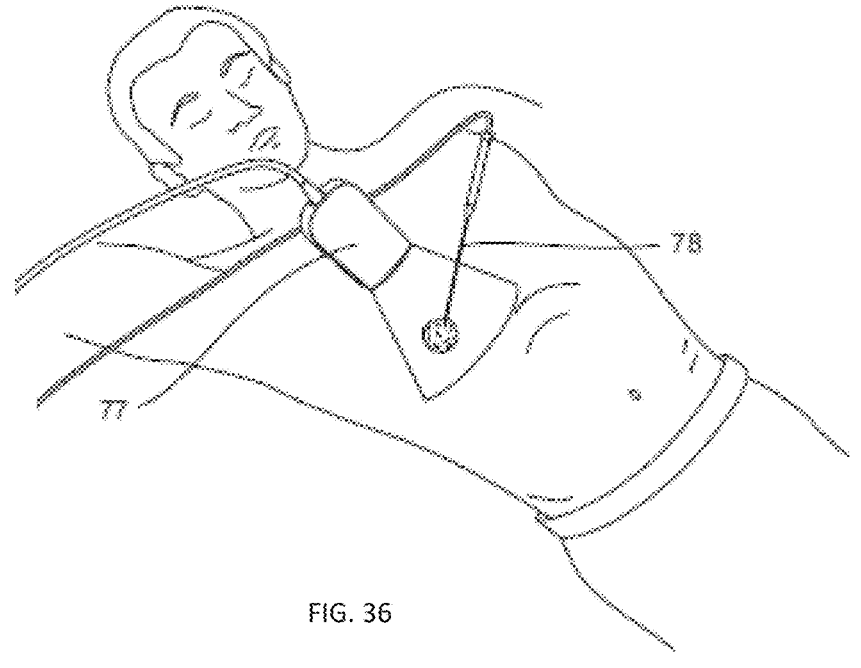
FIG. 36

1

METHODS EMPLOYING GASEOUS NITRIC OXIDE FOR INHIBITING TUMOR GROWTH

RELATED APPLICATIONS

This application is a National Phase of PCT Patent Application No. PCT/IB2020/061150 having International filing date of Nov. 25, 2020, which claims the benefit of priority under 35 USC § 119(e) of U.S. Provisional Patent Application Nos. 62/939,975 filed on Nov. 25, 2019, 62/963, 849 filed on Jan. 21, 2020, 62/982,817 filed on Feb. 28, 2020, 62/984,926 filed on Mar. 4, 2020, 62/985,611 filed on Mar. 5, 2020, 63/027,120 filed on May 19, 2020 and 63/090,345 filed on Oct. 12, 2020. The contents of the above applications are all incorporated by reference as if fully set forth herein in their entirety.

This application is also related to co-filed PCT International Patent Application No. PCT/IB2020/061149 having International filing date of Nov. 25, 2020 and entitled "SYSTEM AND METHOD FOR DELIVERY OF GAS TO A TISSUE", the contents of which are incorporated herein by reference in their entirety.

FIELD AND BACKGROUND OF THE INVENTION

The present invention generally relates to therapy, and more particularly, but not exclusively, to novel methodologies which employ a gas such as gaseous nitric oxide (gNO) for inhibiting growth of cells or tissue of a primary and/or secondary tumor.

In 2018, about 18.1 million new cases of cancer and 9.6 million deaths from cancer have been reported worldwide, and currently, the estimated number of new invasive cancer cases in the United States is around 5,000 per day. Metastases are responsible for a major portion of the morbidity and mortality of cancer, accounting for approximately 90% of all cancer-related deaths. In fact, the survival among metastatic cancer patients has not improved within the past decade. Despite the high mortality from metastatic cancers, therapeutic targets to prevent metastases are limited (Qian et al. Chin J Cancer 36(1), 38, 2017).

Over 200 anti-cancer drugs have been approved so far for clinical applications. These therapies inhibit cancer growth mechanisms, such as proliferation or angiogenesis, or enhance the host immune response. However, the effect of these therapies on survival is mitigated by their minimal inhibition of cancer metastasis (Qian et al. Chin J Cancer 36(1), 38, 2017).

Surgery is a crucial intervention and provides a chance of cure for patients with cancer. However, surgery has the potential to induce the formation of new metastatic disease. The damage to the patients' tissues during excision and manipulation of the tumor being resected and its vasculature have been shown to result in shedding of tumor cells into the blood and lymphatic circulation (Tohme et al. Cancer Res 77(7), 1548-1552, 2017).

Tumor ablation is a minimally invasive technique that is commonly used in the treatment of solid tumors. There are several ablation methods, such as radiofrequency, microwave ablation, high intensity focused ultrasound ablation, laser ablation and cryoablation (Knavel, E. M and Brace, C.L. Tech Vase Interv Radiol 16(4), 192-200, 2013). Image-guided tumor ablation for early stage hepatocellular carcinoma (HCC) is an accepted non-surgical treatment that provides local tumor control and favorable survival benefit (Kang, T. W and Rhim, H. Liver Cancer 4(3), 176-187, 2015).

Local and in situ tumor ablation methods have been shown to enhance anti-tumor immune responses resulting in the destruction of residual malignant cells in primary tumors and distant metastases (Confino et al. Cancer Immunol Immunother 64(2) 191-199, 2015). It has been suggested that tumor ablation generates cancerous debris in situ, and the release of molecules including tumor antigens and damage-associated molecular patterns (DAMPs) may initiate an immune cascade. In order to trigger an adaptive and tumor-specific anti-tumor immune response, antigen-presenting cells need to take up these tumor antigens and DAMPs and, following activation, and present them to immune effector cells (Van den Bijgaart et al. Cancer Immunol Immunother 66(2), 247-258, 2017).

Nitric oxide (NO) is a short-lived, endogenously produced gas that acts as a signaling molecule in the body (Thomas, D. D. Redox Biol 5, 225-233, 2015). Increasing evidence highlights its wide spectrum of action in different pathologic conditions, including cancer (Huerta, S. Futur. Sci. OA 1, FS044, 2015) and involvement in immune cell signaling against pathogens (Schairer et al. Virulence 3, 271-279, 2012).

Preclinical studies testing the effect of exogenously administered nitric oxide (NO) demonstrated its anti-cancer properties and suggested that NO may serve as a potent tumoricidal agent. It has been suggested that while NO treatment at low dose might possess pro-oncogenic properties, NO treatment at high doses has a role in cancer therapeutics either as a single agent or in combination with other antineoplastic compounds (Seabra, A. B and Durin, N. Eur J Pharmacol 826,158-168, 2018). Reports concerning NO donors suggest that high concentrations of NO are recognized as having an anti-tumor effects by inducing apoptosis (Ning et al. Biochem Biophys Res Commun 447(3), 537-542, 2014); that NO can lead to apoptosis via the generation of reactive nitric oxide species, including peroxynitrite, which can oxidize the DNA inducing single strand breaks in DNA; that NO can promote changes in the mitochondrial permeability transition pore, resulting in downstream apoptosis; and that cell death is also caused by the release of intracellular calcium due to the release of cytochrome C. Peroxynitrite oxidizes transcription factors and kinases, perturbing the cell redox network (Bonavida et al. Nitric Oxide. 2008 September; 19(2):152-7).

It has further been suggested that NO donors can mediate chemo-immunosensitization of resistant tumor cells to apoptosis. The upregulation of NO leads in an upregulation of death receptors on the tumor cells membrane and sensitization to death ligands (Bonavida et al. Redox Biol 6, 486-494, 2015). Specifically, studies investigating Sildenafil, a phosphodiesterase 5 (PDE5) inhibitor that restores NO signaling, have shown that it is cytotoxic to cancer cells and serves as a chemo-adjuvant (El-Naa, M. M. et al. Drug Des. Devel. Ther 10, 3661-3672, 2016).

Sensitization of tumors to chemotherapy and radiotherapy has been attributed to improvement in the tumor blood flow and drug delivery mediated by NO (Bonavida et al. Redox Biol 6, 486-494, 2015). Poor blood flow may impair the delivery of drugs and immune cells in tumors, compromises their efficacy after they accrue in tumors, and, independent of these, fuels tumor progression and metastasis and induces immunosuppression (Stylianopoulos et al. Trends Cancer 4(4), 292-319, 2018).

The role of NO donors in inhibition of cancer cell survival and sensitization of drug-resistant tumor cells to apoptosis by both chemotherapy and immunotherapy was observed in various cancer models, such as in glioblastoma cells in vitro (Weyerbrock et al. J Neurosurg 110(1), 128-136, 2009), and breast cancer mouse model in vitro and in vivo (Nath et al. Molecules 20(7), 12481-12499, 2015). NO donors were shown to induce the expression of metastatic suppressor genes (Bonavida et al. Nitric Oxide 19(2):152-157, 2008).

NO has been proven to activate innate and adaptive responses of the immune system against tumors, depending primarily on its concentration. At high concentrations, it is believed to modulate immune-mediated anti-tumor activities (Vannini et al. Redox Biol 6, 334-343, 2015). In lymphoma tumor-bearing mice, NO production in the tumor microenvironment was shown as essential for the anti-tumor activity of CD8+ T cells (Salimian Rizi et al. Trends Cancer 3(9), 659-672, 2017). In a mouse breast cancer model, nitric oxide Synthase (NOS)2 activity in cancer cells was essential for immune modulation activity. NO release to the tumor microenvironment and enhanced iNOS activity were associated with elevated anti-tumor activity in pancreatic cancer cells in vitro, a human ovarian cancer model, and rodent colon and breast models as well as murine sarcoma hepatic metastasis (Vannini et al. Redox Biol 6, 334-343, 2015). In addition, NO was reported to play a key role in the induction of immunogenic cell death of melanoma cells, suggesting stimulation of an anti-tumor immune response (Lin et al. Adv Sci (Weinh) 6(6):1802062, 2019).

Additional Background Art includes Huerta, Future Sci. OA (2015) 1(1), FS044; WO 2008/095311; WO 2008/095312; WO 2013/132500; WO 2014/0088490; WO 2013/132503; U.S. Pat. No. 8,168,232; Confino H et al. Gaseous Nitric Oxide at High Concentrations is a Powerful Anti Tumor Agent both in vitro and in vivo. AACR 2020; Confino H et al. Nitric oxide tumor ablation stimulates an anti-tumor immune response in mice, AACR Tumor Immunology and Immunotherapy 2020; and Confino H et al. Nitric Oxide Lung Cancer Active Vaccination, NACLC 2020.

SUMMARY OF THE INVENTION

According to an aspect of some embodiments of the present invention there is provided a method of inhibiting growth of cells or tissue of a primary and/or secondary tumor in a subject in need thereof, the method comprising locally administering to the tumor gaseous nitric oxide (gNO) at a dose of from about 1,000 ppm to about 1,000,000 ppm for a time period of from about 1 second to about 60 minutes at a flow volume of from about 0.00001 LPM to about 1 LPM.

According to some of any of the embodiments described herein, the gNO is administered at a dose of from about 20,000 ppm to about 200,000 ppm or from about 20,000 ppm to about 50,000 ppm.

According to some of any of the embodiments described herein, the gNO is administered for a time period that ranges from about 30 seconds to about 10 minutes.

According to some of any of the embodiments described herein, the gNO is administered at a flow volume of from about 0.001 LPM to about 0.5 LPM.

According to some of any of the embodiments described herein, the gNO is administered at two or more administration sites in the tumor.

According to some of any of the embodiments described herein, the distance between the two or more administration sites is, independently, from about 2.5 mm to about 1 cm, or from about 0.25 cm to about 0.5 cm.

According to some of any of the embodiments described herein, the gNO is administered at a dose of from about 0.1 mg to about 300 mg, per $cm^3$ tumor.

According to some of any of the embodiments described herein, the gNO is administered at a dose of from about 0.01 mg to about 100 mg, or from 0.1 mg to about 10 mg, per a tumor of 20 $mm^3$ or less.

According to some of any of the embodiments described herein, locally administering the gNO is by intratumoral injection.

According to some of any of the embodiments described herein, the method further comprises scavenging excess gNO from the administration site.

According to some of any of the embodiments described herein, locally administering the gNO is pulsed from about 2 to about 20 times.

According to some of any of the embodiments described herein, locally administering the gNO to the subject is performed at least once.

According to some of any of the embodiments described herein, locally administering the gNO to the subject is performed at least twice.

According to some of any of the embodiments described herein, a time interval between the two administrations is at least one week.

According to some of any of the embodiments described herein, the method further comprises co-administering to the subject an anti-cancer therapy, as described herein.

According to some of any of the embodiments described herein, the method is for inhibiting growth and/or killing cells of a primary tumor.

According to some of any of the embodiments described herein, the method is for preventing occurrence, inhibiting growth and/or killing cells of a secondary tumor.

According to some of any of the embodiments described herein, the secondary tumor comprises metastasizing tumor and/or a recurrent tumor.

According to some of any of the embodiments described herein, the method is for stimulating in the subject an immunological response to the tumor, thereby inhibiting growth of a primary tumor and/or a secondary tumor.

According to an aspect of some embodiments of the present invention there is provided a method of inducing an immunological response to a tumor in a subject afflicted by the tumor, the method comprising exposing at least a portion of the tumor to gNO at a dose of from about 1,000 ppm to about 1,000,000 ppm for a time period of from about 1 second to about 60 minutes at a flow volume of from about 0.00001 LPM to about 1 LPM; subsequent to the exposing, isolating immune cells from the subject; and re-introducing the immune cells to the subject.

According to some of any of the embodiments described herein, the immune cells comprise leukocytes isolated from a blood lymphatic organ of the subject and/or from the tumor.

According to some of any of the embodiments described herein, the method further comprises, subsequent to isolating the immune cells and prior to re-introducing the immune cells to the subject, proliferating and/or purifying the immune cells.

According to some of any of the embodiments described herein, isolating the immune cells is performed from about 1 to about 21 days subsequent to the exposing.

According to some of any of the embodiments described herein, the method further comprises, subsequent to the isolating, preserving the immune cells.

According to some of any of the embodiments described herein, the tumor is a primary tumor and the method is for inhibiting growth and/or killing cells or tissue of the tumor.

According to some of any of the embodiments described herein, the tumor is a primary tumor and re-introducing the immune cells to the subject is performed upon occurrence of a metastatic event and/or recurrence of the tumor, thereby inhibiting growth of a secondary tumor.

According to some of any of the embodiments described herein, exposing at least a portion of the tumor to gaseous NO is by intratumoral injection of the gNO.

According to an aspect of some embodiments of the present invention there is provided a composition comprising immune cells isolated from a subject afflicted by a tumor upon exposing at least a portion of the tumor to gaseous NO.

According to some of any of the embodiments described herein, the exposing is to a dose of gNO of from about 1,000 ppm to about 1,000,000 ppm for a time period of from about 1 second to about 60 minutes at a flow volume of from about 0.00001 LPM to about 1 LPM.

According to some of any of the embodiments described herein, the exposing comprises intratumoral administration of gNO to the subject.

According to an aspect of some embodiments of the present invention there is provided a method of stimulating an immunological response to a tumor in a subject afflicted by the tumor, the method comprising exposing a tumor sample isolated from the subject, or a biomaterial extracted therefrom, to gaseous nitric oxide (gNO); subsequent to the exposing, contacting the tumor sample or a biomaterial extracted therefrom with antigen presenting immune cells, to thereby obtain immune cells presenting an autologous antigenic biomaterial; and administering the immune cells to the subject.

According to some of any of the embodiments described herein, the method is for inhibiting growth and/or killing cells or tissue of a primary tumor in the subject.

According to some of any of the embodiments described herein, the method is for preventing and/or inhibiting growth of a secondary (recurrent and/or metastasizing) tumor in the subject.

According to some of any of the embodiments described herein, the method is for vaccinating the subject against the tumor.

According to some of any of the embodiments described herein, the exposing to gaseous nitric oxide (gNO) is at a dose of from about 100 ppm to about 1,000,000 ppm for a time period of from about 1 second to about 60 minutes at a flow volume of from about 0.00001 LPM to about 1 LPM.

According to some of any of the embodiments described herein, the method further comprises, prior to or subsequent to the exposing, processing the tumor sample to thereby extract the biomaterial from the tumor sample.

According to some of any of the embodiments described herein, the antigen presenting immune cells are autologous immune cells.

According to some of any of the embodiments described herein, the autologous immune cells are isolated from a blood organ of the subject.

According to some of any of the embodiments described herein, the method further comprises administering to the subject an anticancer therapy.

According to an aspect of some embodiments of the present invention there is provided an antigenic biomaterial extracted from tumor cells of a subject upon exposing the tumor cells or a biomaterial extracted therefrom to gaseous NO.

According to an aspect of some embodiments of the present invention there are provided antigen presenting immune cells comprising the antigenic biomaterial as described herein in any of the respective embodiments and any combination thereof.

According to an aspect of some embodiments of the present invention there is provided a method of stimulating an anti-tumor immune response in a subject in need thereof, the method comprising administering to the subject the antigen presenting immune cells of as described herein.

According to some of any of the embodiments described herein, the antigenic biomaterial is extracted from tumor cells of the subject or from tumor cells of another subject afflicted by the same tumor type.

According to some of any of the embodiments described herein, the antigen presenting immune cells are obtainable by incubating immune cells with the antigenic biomaterial, and wherein the immune cells are derived from the subject or from another subject.

According to an aspect of some embodiments of the present invention there is provided a method of inhibiting growth and/or killing cells of a primary and/or secondary tumor in a subject in need thereof, the method comprising:

exposing a tumor sample isolated from the subject, or a biomaterial extracted therefrom, to gaseous nitric oxide (gNO); subsequent to the exposing, contacting the tumor sample or a biomaterial extracted therefrom with antigen presenting immune cells, to thereby obtain immune cells presenting an autologous antigenic biomaterial; and administering the immune cells to the subject; and locally administering to the tumor gaseous nitric oxide at a dose of from about 0.1 mg to about 300 mg, per cm³ tumor.

According to some of any of the embodiments described herein, the method further comprises administering to the subject an anti-cancer therapy.

According to an aspect of some embodiments of the present invention there is provided a method of inhibiting growth of cells of a primary and/or secondary tumor in a subject in need thereof, the method comprising locally administering to the tumor a gas at a volumetric flow (flow volume) of from 0.00001 LPM to about 10 LPM and a pressure of from about 0.1 to about 10 bar, for a time period of at least 1 second.

According to some of any of the embodiments described herein, the volumetric flow ranges from about 0.0001 LPM to about 1 LPM or to about 0.1 LPM.

According to some of any of the embodiments described herein, the administering is to a tumor having a volume of less than 20 cm³, or of from 0.1 to 10 cm³.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 7 is a bar graph showing the effect of 10,000-25,000 ppm NO or air on LLC1 cells in-vitro.

FIGS. 8A-C present the effect of 10,000-20,000 ppm NO or air on LLC1 cell death type in-vitro as measured in Annexin V—Propidium Iodide apoptosis-necrosis assay.

FIGS. 10A-F are photographs depicting the effect of gNO at 10,000 ppm on a CT-26 tumor bearing mouse at 2 days before treatment, 1 minute after treatment, 9 days post treatment and 14 days post treatment, respectively (FIGS. 10A-D), and of the system used for delivering gNO by placing the tumor inside a container filled with gNO (FIG. 10E); and a tumor growth curve post-treatment with 10,000 ppm NO (FIG. 10F).

FIGS. 11A-C present tumor growth curves depicting the effect of gNO at 10,000-50,000 ppm on tumor volume in CT-26 tumor bearing mice, compared to air-treated CT-26 tumor bearing mouse as control (FIG. 11A), and photographs showing an exemplary system as used for intratumoral gNO delivery according to some embodiments of the present invention (FIG. 11B) and an exemplary system as used for gNO delivery via capping of a tumor according to some embodiments of the present invention (FIG. 11C).

FIG. 13 are photographs depicting the effect of gNO at 25,000 ppm for 2 cycles of 15-minute treatment on two CT-26 tumor bearing mice before treatment (right photographs) and 44 days post treatment (left photographs).

FIG. 14 are photographs depicting the effect of gNO at 200,000 ppm for 2 seconds on a CT-26 tumor bearing mice before treatment (upper photographs) and 9 days post treatment (lower photograph).

FIGS. 18A-C present a schematic depiction of a challenge assay in which splenocytes extracted from CT26 gNO-immunized mice where inoculated to naïve mice depict (FIG. 18A), a bar graph showing the percentage of CT26 tumor cells take when mixed with splenocytes extracted from CT26 immunized mice prior to inoculation to naïve mice (FIG. 18B) and a bar graph showing the number of mice that developed a tumor after inoculation of CT26 cells together with splenocytes from an immunized mouse (FIG. 18C).

FIGS. 35A-C illustrate an exemplary tumor excision procedure accompanied by gNO release before (FIG. 35A) during (FIG. 35B) and after (FIG. 35C) surgery, according to some embodiments of the present invention.

FIG. 36 illustrate an exemplary imaging guided gNO based treatment, according to some embodiments of the present invention.

DESCRIPTION OF SPECIFIC EMBODIMENTS OF THE INVENTION

Figure 1:
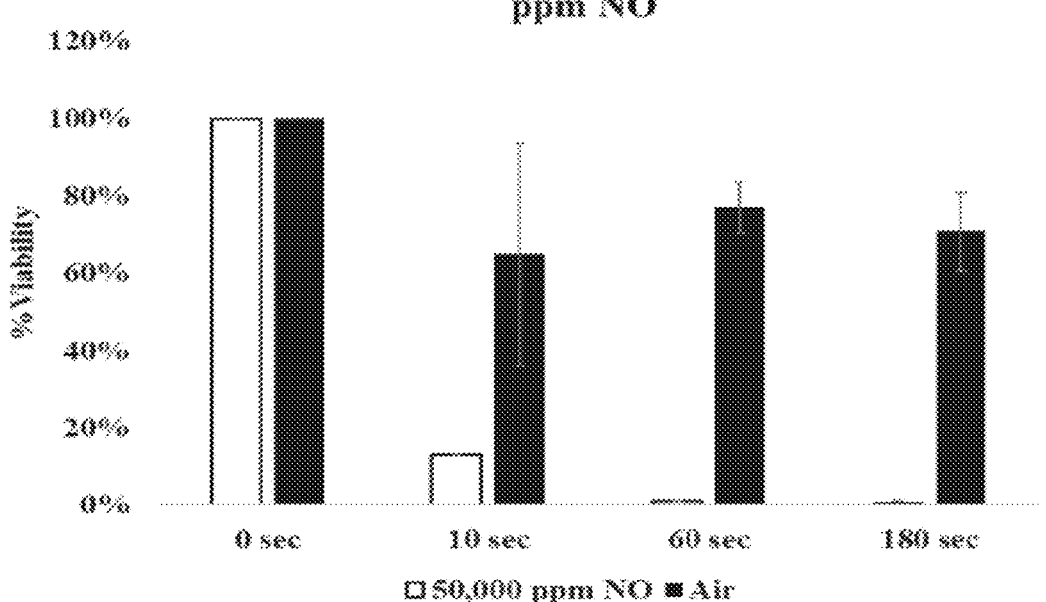
FIG. 1 is a bar graph showing the effect of 50,000 ppm NO or air on CT-26 cells in-vitro.

The present invention generally relates to therapy, and more particularly, but not exclusively, to novel methodologies which employ a gas such as gaseous nitric oxide (gNO) for inhibiting growth of cells or tissue of a primary and/or secondary tumor.

The present inventors have devised and successfully practiced a novel treatment paradigm that involves in situ tumor ablation by local administration of high dose gaseous NO (gNO) to the tumor.

The present inventors have considered the following advantages which are attributed to gNO-based local treatment (e.g., ablation) over other ablation methods: (i) the highly diffusible nature of gNO may accelerate its distribution within the tumor, while its short half-life limits its effect to the tumor site; (ii) a short-term gNO treatment is sufficient in order to stimulate an anti-tumor response; (iii) gNO plays a significant role in the immune response. The present inventors have considered reports suggesting that at high doses, gNO is believed to have immune-mediated anti-tumor activities [see, for example, Vannini et al. Redox Biol 6, 334-343, 2015], indicating that the tumor is destroyed via an immune-stimulating technique, and have designed a methodology according to which high doses of gNO are used to treat tumor cells, to thereby both eradicate the tumor cells and stimulate an immune response against the tumor, which is usable both to treat a primary tumor and to vaccinate the patient against secondary tumors (e.g., as metastases and/or recurrent tumor).

The present invention provides methods to treat tumors or cancers by local administration of gNO, preferably of high dose gNO as described in further detail hereinunder.

The present invention provides methods to treat tumors or cancers by local administration of a gas, preferably under a high pressure and for a sufficient time period, as described in further detail hereinunder.

High dose gNO is defined as the delivery of gNO in a preferably inert gas such as nitrogen at a concentration of between about 1,000 and 1,000,000 ppm, as is described in further detail hereinafter.

The methods of delivering gNO may include administration of gNO in a continuous or pulsed manner.

The present invention provides methods to stimulate an immunological response to a tumor in a subject in need thereof, which employ gNO, and which can be effected in vivo and/or ex vivo, as described in further detail hereinunder.

Local Administration of gNO:

According to aspects of some embodiments of the present invention there are provided methods of inhibiting growth of cells or tissue of a primary and/or secondary tumor in a subject in need thereof.

According to some embodiments of the present invention, the methods are effected by locally administering to the tumor gaseous NO (gNO).

By "locally administering" it is meant directly contacting the tumor cells or tissue with gNO, such that gNO is applied directly to the tumor and/or its close vicinity. In some embodiments, local administration of gNO is effected intra-tumorally, by applying gNO directly into the tumor cells or tissue. In some embodiments, local administration of gNO is effected by applying gNO to the surface of the tumor tissue, for example, by contacting the tumor's surface with gNO. In some embodiments, local administration is effected by bringing gNO in close vicinity to the tumor cells or tissue, for example, directly or up to 2 cm, or up to 1 cm, from at least one and preferably all of the tumor surfaces.

In some of any of the embodiments described herein, local administration is effected intratumorally, such that gNO is injected or otherwise delivered into the tumor.

In some of any of the embodiments described herein, local administration is effected by spraying or otherwise applying gNO onto at least one of the tumor's surface. At least some of the gNO then enters into the tumor via, e.g., diffusion.

In some of any of the embodiments described herein, local administration is effected by exposing the tumor to gNO in a close container, such that gNO is contacted with the tumor and enters into the tumor via e.g., diffusion. The container can be open or closed and can be sized to conform to the contours of the tumor.

In some of any of the embodiments described herein, local administration is effected by delivering gNO to a physi-ological space or cavity which contains at least a portion of the tumor tissue, such that the tumor is contacted with the gNO, and the gNO enters the tumor via e.g., diffusion.

These and other embodiments relating to methodologies and systems for local administration of gNO are described in further detail hereinunder.

According to an aspect of some embodiments of the invention there is provided a gaseous NO for use in inhib-iting growth of cells of a primary and/or secondary tumor, wherein the gaseous NO is locally administered to the tumor, as described herein in any of the respective embodiments.

According to an aspect of some embodiments of the present invention there is provided a use of gaseous NO as a medicament for inhibiting growth of cells of a primary and/or secondary tumor, wherein the medicament is formu-lated for local administration of gNO to the tumor cells or tissue.

According to some of any of the embodiments described herein for local administration of gNO, a high dose of gNO is administered locally, as described herein. These embodi-ments are also referred to herein as "high dose local admin-istration of gNO", "high dose gNO treatment", and gram-matical diversions of the foregoing, or simply as "high dose gNO".

In some of any of the embodiments described herein, the high dose of gNO is reflected by its relatively high concen-tration in the total amount of gas that is locally administered to the tumor, and is presented by ppm (part per million) units.

In some of any of the embodiments described herein, the high dose of gNO is presented as its fraction, in ppm units, in the gas carrier. The gas carrier can be air, and preferably an inert gas such as nitrogen or argon, preferably nitrogen.

In some of any of the embodiments described herein, the high dose of gNO is reflected by the mass of gNO that is locally administered to the tumor, per a volumetric unit of the tumor.

According to some of any of the embodiments described herein, the gNO is locally administered, as described herein in any of the respective embodiments, at a concentration of from about 1,000 ppm to about 1,000,000 ppm (0.1% to 100%), including any intermediate values and subranges therebetween, for example, from about 1,000 ppm to about 200,000 ppm, or from about 1,000 ppm to about 100,000 ppm, preferably from about 10,000 ppm to about 500,000 ppm, or from about 10,000 ppm to about 200,000 ppm, or from about 10,000 ppm to about 100,000 ppm, or from about 20,000 ppm to about 100,000 ppm, or from about 25,000 ppm to about 100,000 ppm, or from about 25,000 ppm to about 75,000 ppm, or from about 10,000 ppm to about 50,000 ppm, or from about 50,000 ppm to about 100,000 ppm, including any intermediate values and subranges between any of the foregoing, or is about 50,000 ppm.

In some of any of the embodiments described herein in the context of high dose of gNO, the high dose can be obtained by locally administering gNO at a dose of at least 10,000 ppm, or at least 20,000 ppm, or at least 50,000 ppm, and optionally up to about 1,000,000 ppm.

In exemplary embodiments, the gNO is locally adminis-tered, as described herein in any of the respective embodi-ments, at a concentration of about 50,000 ppm.

In exemplary embodiments, the gNO is locally adminis-tered, as described herein in any of the respective embodi-ments, at a concentration of about 25,000 ppm. In exemplary embodiments, the gNO is locally administered, as described herein in any of the respective embodiments, at a concen-tration of about 20,000 ppm. In exemplary embodiments, the gNO is locally administered, as described herein in any of the respective embodiments, at a concentration of about 10,000 ppm. In exemplary embodiments, the gNO is locally administered, as described herein in any of the respective embodiments, at a concentration of about 100,000 ppm. In exemplary embodiments, the gNO is locally administered, as described herein in any of the respective embodiments, at a concentration of from about 100,000 ppm to about 200,000 ppm, or from about 200,000 ppm to about 500,000 ppm, or from about 500,000 ppm to about 1,000,000 ppm or from about 50,000 ppm or about 100,000 ppm or about 200,000 ppm or about 500,000 ppm or about 1,000,000 ppm.

According to some of any of the embodiments described herein, the gNO is locally administered, as described herein in any of the respective embodiments, at a volumetric flow rate of from about 0.00001 LPM to about 10 LPM, prefer-ably from about 0.0001 LPM and about 1 LPM, or from about 0.001 LPM and 0.5 LPM, including any intermediate values and subranges therebetween. For example, the volu-metric flow rate can be from about 0.001 LPM to about 0.01 LPM, or from about 0.01 LPM to about 0.1 LPM, or from about 0.1 LPM to about 0.25 LPM, or from about 0.25 LPM to about 0.5 LPM, or from about 0.5 LPM to about 1 LPM, or from about 1 LPM to about 2 LPM, or from about 2 LPM to about 3 LPM, or from about 3 LPM to about 4 LPM, or from about 4 LPM to about 5 LPM, or from about 5 LPM to about 6 LPM, or from about 7 LPM to about 8 LPM, or from about 8 LPM to about 9 LPM, or from about 9 LPM to about 10 LPM, including any intermediate values and subranges therebetween, or it can be, for example, about 0.0001 LPM, or about 0.001 LPM, or about 0.01 LPM, or about 0.1 LPM, or about 1 LPM or about 10 LPM.

According to some of any of the embodiments described herein, the gNO is administered for a time period that ranges from about 0.1 seconds to about 10 hours, per administra-tion, including any intermediate values and subranges ther-ebetween. For example, the time period can be from about 0.1 second to about 1 hour, or from about 1 second to about 10 minutes, or from about 1 minute to about 10 minutes, or from about 10 seconds to about 10 minutes, or from about 0.1 second to about 10 minutes, or from about 30 seconds to about 3 minutes, or from about 1 minute to about 30 minutes, or from about 10 minutes to about 60 minutes, or from about 60 minutes to about 180 minutes, or from about 180 minutes to about 600 minutes, including any intermediate values and subranges between any of foregoing, or it can be about 30 seconds, about 10 minutes, about 30 minutes, or about 60 minutes.

In some of any of the embodiments related to methods and uses as described herein in the context of high dose of gNO, the high dose can be obtained by locally administering gNO, as described herein in any of the respective embodiments, at a dose of from about 1,000 ppm to about 1,000,000 ppm for a time period of from about 1 second to about 60 minutes at a volumetric flow (flow volume) of from about 0.00001 liter per minute (LPM) to about 1 LPM, including any intermediate values and subranges between any of the foregoing.

In some of any of the embodiments related to methods and uses as described herein in the context of high dose of gNO, the high dose can be obtained by locally administering gNO, as described herein in any of the respective embodiments, at a dose of at least 10,000 ppm, and optionally up to about 1,000,000, or up to about 500,000 ppm, or up to about 200,000 ppm, or up to about 100,000 ppm, for a time period of from about 1 second to about 60 minutes at a volumetric flow (flow volume) of from about 0.0001 liter per minute (LPM) to about 1 LPM, including any intermediate values and subranges between any of the foregoing.

In some of any of the embodiments described herein in the context of high dose of gNO, the high dose can be obtained by locally administering gNO at a dose of at least 10,000 ppm, or at least 20,000 ppm, or at least 50,000 ppm, and optionally up to about 1,000,000 ppm, for a time period of at least 1 second, or at least 10 seconds, or at least 30 seconds, or at least 1 minute, and optionally up to about 60 minutes, at a volumetric flow rate (flow volume) of at least 0.0001 liter per minute (LPM), or at least 0.001 LPM, or at least 0.01 LPM, and optionally up to about 1 LPM, including any intermediate values and subranges between any of the foregoing.

Alternatively or in addition, in any of the methods and uses described herein in the context of high dose of gNO, the amount of gNO locally administered to the tumor ranges from about 0.1 mg to about 300 mg, per cm³ tumor, per administration.

The parameters of the gNO concentration (ppm), volumetric flow rate (LPM) and time to achieve a desired mass of gNO, and vice versa, the gNO mass achieved by locally administering gNO at a concentration, volumetric flow and time, can be calculated using the known ideal gas equation, PV=nRT, wherein P is the pressure, V is the volume, n is the number of moles, R is the gas constant and T is the temperature.

More specifically, these relations can be calculated or converted one to the other using the following equations:

$$X = y \times 10^{-6} \qquad 1)$$

$$V = \dot{V} \times t \qquad 2)$$

$$n = \frac{V \times 10^{-3} \times 101325}{8.314 \times 298} \qquad 3)$$

14

-continued $$m = n \times X \times 30.01 \times 10^3 \qquad 4)$$

$$m = \left( \frac{(\dot{V} \times t) \times 10^{-3} \times 101325}{8.314 \times 298} \right) \times (y \times 10^{-6}) \times 30.01 \times 10 \qquad 5)$$

y is the concentration in ppm units;

X is the concentration in molar fraction units, and equation 1 presents the relation between molar fraction and ppm (y);

V is the volume, $\dot{V}$ is the volumetric flow in LPM and t is the time in minutes, and equation 2 presents the relation between Volume, volumetric flow rate and time;

Equation 3 is the Ideal gas equation, and the $10^{-3}$ factor is added for transformation from Liters to m³;

Equation 4 presents the relation between the mass (m) the mole number (n), the molar fraction X and Nitric Oxide molar mass (30.01 grams/mol); and Equation 5 is a combination of equations 1-4 into a single equation, reflecting the relation between the mass of gNO and the molar fraction, volumetric flow and time. The $10^3$ is for obtaining the mass m on a milligram (mg) scale.

Thus, for example, at a volumetric flow of 0.1 LPM, time of 1 minute and concentration of 50,000 ppm, using equation 5 above, about 6.1-6.2 mg gNO is administered.

According to some of any of the embodiments described herein, the gNO is locally administered, as described herein in any of the respective embodiments, at a concentration of from about 1,000 ppm to about 1,000,000 ppm (0.1% to 100%), preferably from about 10,000 ppm to about 500,000 ppm, or from about 10,000 ppm to about 100,000 ppm, or at about 50,000 ppm; at a volumetric flow rate of from about 0.0001 LPM to about 10 LPM, preferably from about 0.001 LPM and 1 LPM; and during a time period that ranges from about 1 second to about 30 minutes, per administration.

According to some of any of the embodiments described herein, the gNO is locally administered, as described herein in any of the respective embodiments, at a concentration (dose) of from about 20,000 ppm to about 100,000 ppm or from about 20,000 ppm to about 50,000 ppm; for a time period that ranges from about 30 seconds to about 10 minutes; at a volumetric flow (flow volume) of from about 0.001 LPM to about 0.5 LPM, per administration.

According to some of any of the embodiments described herein, the gNO is locally administered, as described herein in any of the respective embodiments, in an amount of no more 1 mg gNO per 100 mm³ tumor volume, per administration, so as to avoid possible damage to healthy tissues adjacent to, or surrounding, the treated tumor.

According to some of any of the embodiments described herein, the gNO is locally administered, as described herein in any of the respective embodiments, in an amount of about 250 mg per cm³ tumor, per administration.

According to some of any of the embodiments described herein, the gNO is locally administered, as described herein in any of the respective embodiments, in an amount of from about 0.1 to about 10 mg per a tumor of 20 mm³ or less, including any intermediate values and subranges therebetween.

According to some of any of the embodiments described herein, the gNO is locally administered, as described herein in any of the respective embodiments, in an amount of from about 0.1 to about 300 mg including any intermediate values and subranges therebetween, per 1 cm³ tumor, per administration. For example, the gNO is locally administered in an amount of from about 0.1 mg to about 250 mg, or from 0.1 mg to about 100 mg, or from 1 mg to about 50 mg, or from about 1 mg to about 100 mg, or from about 1 mg to about 300 mg, of from about 50 mg to about 100 mg, or from about 50 mg to about 300 mg, or from about 100 mg to about 150 mg, or from about 100 mg to about 300 mg, or from about 10 mg to about 100 mg, or of from about 10 mg to about 250 mg, or from about 0.1 mg to about 10 mg, or from about 10 mg to 200 mg, including any intermediate values and subranges of any of the foregoing, per 1 cm³ tumor, per administration.

According to some of any of the embodiments described herein, the gNO is locally administered, as described herein in any of the respective embodiments, to a tumor having a volume of up to 20 mm³, and an amount of gNO that is locally administered as described herein in any of the respective embodiments is from about 0.001 mg to about 10 mg, or from about 0.01 mg to about 20 mg, or from about 0.01 mg to about 2 mg, or from about 0.1 mg to about 1.0 mg, or from about 0.2 mg to about 0.8 mg, including any intermediate values and subranges between any of the foregoing, per administration.

Without being bound by any particular theory, it is assumed that a high dose (concentration or amount) as described herein in any of the respective embodiments, inhibits the growth of tumor cells, reduces tumor volume and/or stimulates an anti-tumor immune response, as described herein in any of the respective embodiments, without causing a harmful effect to healthy tissues in the vicinity of the tumor.

For any of the embodiments described herein for local administration of gNO, the administration can be either continuous or pulsed, such that for each administration, the indicated dose of gNO is administered either continuously or in a pulsed manner. When the high dose is referred to in ppm units, each pulse is at the indicated high dose concentration, as described herein in any of the respective embodiments. When the high dose is referred to as the total mass per administration, the indicated dose is divided into pulses.

According to some of any of the embodiments described herein, gNO is pulsed from about 2 to about 50 times, or from about 2 to about 30 times, or from about 2 to about 20 times, or from about 2 to about 15 times, or from about 5 to about 15 times, including any intermediate values and subranges therebetween, or about 10 times, per administration.

According to some of any of the embodiments described herein, each pulse is between about 1,000 ppm and about 1,000,000 ppm, or between 4000 ppm and about 1,000,000 ppm gNO, or between 10,000 ppm and about 1,000,000 ppm gNO, at a volumetric flow (flow volume) of from about 0.00001 LPM to about 0.5 LPM, wherein each pulse is, independently, between about 0.1 second and about 10 minutes per pulse with a break of from about 0.1 second to about 10 minutes between pulses.

According to some of any of the embodiments described herein, each pulse of gNO is, independently, from about 10 seconds per pulse to about 45 seconds per pulse, including any intermediate values and subranges therebetween.

According to some of any of the embodiments described herein, each pulse of gNO is about seconds per pulse.

According to some of any of the embodiments described herein, gNO is not administered between pulses and the time between each two pulses is, independently, from about 1 second to about 300 seconds, or from about 1 second to about 200 seconds, or from about 1 second to about 100 seconds, or from about 1 second to about 50 seconds, or from about 10 seconds to about 50 seconds, including any intermediate values and subranges therebetween, or is about 20 seconds.

According to some of any of these embodiments, the ratio between the time of gNO pulsed administration and the resting time between pulses ranges from 1:2 to 1:5. For example, for each pulse of gNO administration during 5 seconds, a following resting time is independently from 10 to 50 seconds. Preferably, the gNO is pulsed such that about 33% of the time gNO is delivered and 66% of the time is resting or waiting time between pulses.

According to some of any of the embodiments described herein, the gNO is locally administered, as described herein in any of the respective embodiments, at two or more administration sites in or on the tumor (depending in the administration mode). In some of these embodiments, the distance between the two administration sites is, independently, from about 2.5 mm to about 1 cm, or from about 0.25 cm to about 0.5 cm, including any intermediate values and subranges therebetween.

When gNO is administered to two or more tumor sites, each administration is at the ppm dose or mass amount indicated herein in any of the respective embodiments, or, the total mass (amount) administered to all tumor sites is as indicated herein in any of the respective embodiments.

According to some of any of the embodiments described herein, the method further comprises scavenging excess gNO from the one or more administration sites, as described in further detail hereinunder. In exemplary embodiments, the scavenging comprises applying a reduced pressure (vacuum) around the administration site(s).

According to some of any of the embodiments described herein for high dose local administration of gNO, the administration is performed one or more times per a treatment session.

In some embodiments, it is performed once during a treatment session. In some embodiments, it is performed twice, trice or more times during a treatment session. In some of these embodiments, the administration is performed once daily during the treatment session. Preferably, the administration is performed such that a time interval between the two administrations is at least one week, during a treatment session.

The duration of a treatment session can be determined by skilled persons such as physicians, in accordance with the subject's response to the treatment, that is, in accordance with the effect of the treatment on the growth of the cells of the primary and/or secondary tumor, as described herein.

According to some of any of the embodiments described herein for high dose local administration of gNO, the administration is performed once a day, although two or more times a day are also contemplated.

According to some embodiments, the local administration comprises injecting, or exposing the outer layer of a tumor to, or filling a space or cavity containing a tumor with, a high dose gNO, and in some embodiments, the gNO is at a concentration ranging from about 1,000 ppm to about 1,000,000 ppm, preferably 50,000 ppm, as described herein in any of the respective embodiments. The local administration to the tumor is for a period of time of from about 1 second to about 3 hours, depending on the size and location of the tumor, with a very low volume in the order of up to 0.1 LPM and preferably 0.01 LPM.

According to some of any of the embodiments described herein, the gNO local administration treatment is also referred to as a high dose, low volume, local administration or treatment.

According to some of any of the embodiments described herein, in cases where the tumor is covered by skin, peritoneum, crust or any other thick layer, this layer can be removed prior to or during exposure of the tumor to the gNO local administration.

In any of the embodiments described herein in the context of gNO local administration, the gNO may be provided by an external source, for example, a reservoir of gNO or a chemical generator of gNO. In some embodiments, gNO is provided by a reservoir of gNO, preferably of a small volume of, for example, a single administration dosage (that is, the dose of gNO used per a single administration, as described herein in any of the respective embodiments). Such reservoirs are described in further detail hereinunder.

The gNO is preferably of medical purity, that is, preferably at least about 95%, more preferably at least about 99%, and even more preferably at least about 99.5% pure gNO. The gNO is preferably provided as a mixture of gNO and other gases, such as air, nitrogen, oxygen, and so forth, preferably an inert gas such as, for example, nitrogen, and its ppm concentration is within the gas it is mixed with.

Systems and Modes of Administration:

Embodiments of the present invention further relate to a system, which is also referred to herein interchangeably as "device", which is configured for locally administering gNO to a tumor as described herein in any of the respective embodiments. Such a system is also referred to herein as a delivery system.

Generally, but not obligatory, a system for locally administering gNO at a high dose as indicated herein can include a pressure regulator, a flow meter, optionally an exposure box or container, one or more delivery lines, which are optionally terminated by or connected to a delivery device or configuration through which the gNO is administered and further optionally, a NO and/or NOx (as defined hereinunder) detector. Purging the gNO delivery system with an inert gas, such as nitrogen, may be desired.

The volume and/or flow rate of the administered (delivered) gas can be regulated by a digital flow controller, designed to deliver low volumes or low rates of gas, of less than 0.1 LPM per cm$^3$ of tissue, in accordance with any of the respective embodiments as described herein. Purging of the gNO delivery system, including purging the pressure regulator, flow meter and delivery lines can be performed before and/or after gNO local administration. The gas purge can preferably last at least 1 minute or until the NO and NOx (as described below) detectors read no signal. In exemplary embodiments, nitrogen is used as the purging gas at a flow rate of at least 0.5 LPM.

According to some of any of the embodiments described herein, the delivery device is inserted into a body and advanced adjacent to an administration site, on or near tumor cells or tissue. When a delivery device or configuration is appropriately positioned, gNO is supplied and exits the device into the tumor or on or above a surface of the tumor, depending on the nature of the delivery device and the local administration mode of choice. In some embodiments, the delivery device extends against a tumor in order to form a seal, thus further reducing damage that may be caused by the gNO to adjacent normal cells that are outside of the area sealed off by the device.

The delivery device as described herein is meant to describe a component or configuration of the delivery system through which the gas exits the delivery system and contacts the administration site (e.g., the tumor or its close vicinity).

According to some of any of the embodiments described herein, locally administering gNO to a tumor as described herein in any of the respective embodiments can be accomplished by delivery device means such as one or more needles, including, for example, perforated spray needles, non-perforated and non-spray needles, umbrella needles, or other needles. The needles can optionally be nano-sized, micron-sized or macro-sized needles (having a diameter of 1 mm or higher). Other delivery devices are described hereinunder. Embodiments in which needles are used are typically used when the gNO is locally administered intratumorally, e.g., by intratumoral injection.

In some of any of the embodiments described herein in the context of a delivery system, the opening from which the gNO is delivered can be adjusted to the size of the tumor, so as to prevent damage to the area surrounding the cancer. In some embodiments, the opening does not exceed the size of the tumor.

The methods of locally administering gNO to a tumor can include contacting at least a portion of the tumor with the gaseous nitric oxide, and subsequently removing gaseous nitric oxide and NOx gas molecules from the treated site during or after the administration step. NOx encompasses NO, when x is 1, and oxidized forms of NO, which can be formed when gNO is in contact with a physiological environment and/or the subject's environment, whereby x can be, for example, 2. Vacuuming the gas can be done in a pulsed or continuous manner, preferably synchronized with the gNO mode of administration.

A delivery system can include a full-body or a differently-sized chemical hood designed to evacuate excessive gNO or NOx during treatment, in a pulsed or continuous manner, preferably synchronized with the gNO mode of administration.

The delivery system can include an evacuation cylinder, which is connected directly to a regulator of the gNO tank. To purge the regulator safely, the evacuation cylinder can be filled with a gas accumulated in the regulator.

Another embodiment of controlling high dose gNO includes the use of a one-way valve where disconnecting the regulator or flow meter from the cylinder locks the valve, thereby preventing gas release from a gas tank.

According to some of any of the embodiments described herein, the methods, uses and delivery systems as described herein utilize a gNO cylinder, optionally equipped with a gas regulator, and one or more valves, and further optionally, the cylinder further comprises a delivery device for executing the local administration. The delivery device is in fluid communication with the cylinder, preferably via the valves and gas regulator (e.g., flow controller). Alternatively, the cylinder comprises means to connect the delivery device to the cylinder, to obtain fluid communication therebetween. The delivery device can be, for example, a scope with an annular-shape or a needle or a device configured for spraying the tumor, or else, as described in further detail hereinunder.

According to some of any of the embodiments described herein, the gNO cylinder is a miniature or at least portable cylinder.

According to some embodiments, the cylinder is of a volume of less than 1 liter, or less than 0.8 liter, or less than 0.75 liter, or less than 0.5 liter, or less than 0.3 liter.

The cylinder is preferably under low pressure, such as less than about 40 bar (about 600 psi). Thus, the cylinder can deliver about 10 liters of high concentration gNO. A regulator can optionally limit output pressure to about 50 psi, for example, and can be connected to an emergency on/off valve. The gas flow, in a case of, for example, a delivery system configured for injection, can be less than about 0.1 LPM or about 0.05 LPM. The use of such low flow rates during local administration of gNO can assist in limiting the exposure to the tumor or cancerous cells and protect the surrounding area, or healthy cells and tissues.

According to some of any of the embodiments described herein, the methods and uses involve scavenging gNO and optionally other gases, and the scavenging can be performed by applying vacuum so as to remove gNO and other gases the administration site. A delivery system as described herein is configured, according to some embodiments, as being capable of scavenging gNO from an administration site.

A delivery system according to some of the present embodiments can additionally or alternatively comprise one or more, preferably two, vacuum devices for scavenging gaseous nitric oxide and other gases that may form during the local administration. The vacuum devices can be placed or held above, or distal to, the tumor, or to the delivering device, during administration, about 15 cm away. The vacuum devices can vacuum all the gases from the area at a rate of at least about 50 liter per minute. The vacuuming of the gas can be done in a pulsed or continuous manner, preferably synchronized with gNO administration. Purging the gNO delivery system, for example, with nitrogen, before and/or after can also be performed. Purging can also be performed intermittently during the procedure.

According to some embodiments, a chemical hood is placed above the tumor or tumor mass and used to apply vacuum and scavenge gNO. The hood can be placed about 15 cm above the tumor. The hood can vacuum gas at a flow rate of at least about 50 LPM.

A whole-body chemical hood that can accommodate the patient's body can also be used. The patient's head can be placed outside the hood to minimize the risk of breathing NOx molecules. gNO can be delivered as described herein. The vacuum system can exchange the gas at a flow rate of at least 50 liter per minute.

In each of the embodiments that relate to a vacuum application, a NO and NOx filtering pump can be placed in the discharge line. A soda lime filter, such as a Sofnolime filter, or a similar filter that can absorb NOx molecule, can be used. In each instance, vacuuming can be done in a pulsed or continuous manner, preferably synchronized with gNO administration or not.

According to some of any of the embodiments described herein, the delivery system is configured for delivering gNO to one or more administration sites by a positive pressure gradient, and scavenging gNO from the one or more administration sites by a negative pressure gradient. In this way, the delivery system may deliver gNO to one or more administration sites with reduced or nullified damage to collateral host cells.

It is to be noted that a certain level of damage to collateral cells may be tolerated, and that the conditions under which the gNO gas is administered may be optimized to decrease damage to collateral cells while also providing the therapeutic effects described herein.

According to some of any of the embodiments described herein, the delivery system comprises a gas supply passage in fluid communication with gas supply openings. The delivery system can further comprise an exhaust passage in fluid communication with an exhaust opening. The delivery system can comprise one or more gas supply openings and/or one or more exhaust openings, and/or one or more gas supply passages and/or one or more exhaust passages.

Figure 22:
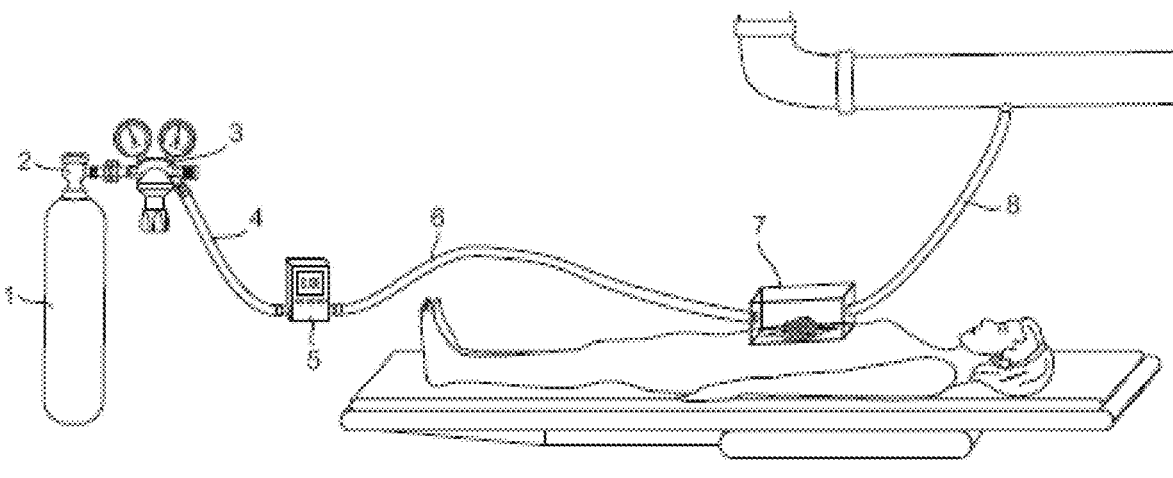
FIG. 22 illustrates an exemplary system for exposing the patient's tumor to gNO in a container, according to some embodiments of the present invention.

An exemplary system for the local administration and scavenging of gaseous nitric oxide comprises a container or box, as illustrated, for example in FIG. 22 and described in further detail hereinunder, that can be filled with high dose (e.g., concentration) gNO at a volume of at least 0.5 Liter Per Minute (LPM) supplied from a tank (a gas reservoir). The container can have 2 or more holes, or ports. A first hole or port can be an input hole, sized to allow insertion of at least a portion of the tumor or of a bodily organ containing the tumor. An output hole can be connected to a discharge conduit or pipe that can remove or evacuate excessive NOx gases out from the box to the outside air, avoiding or minimizing the risk of contaminating the room and overexposing staff and the treated subjects (patients). Applying a vacuum can be in a pulsed or continuous manner, preferably synchronized with gNO administration.

An exemplary delivery system can comprise a small bore inner cannula that delivers an adequate dose of gNO to the target site, for example, a target site of from about 1 mm$^2$ to about 2 cm$^2$ in size. The delivery system can further comprise an outer lumen through which a vacuum may be applied to scavenge excess gNO away from tumor cells and tissue that surround and border the tumor site. Such a configuration allows locally administering gNO to the target site (a tumor), without excessive damage to healthy host tissues.

In an exemplary method, a tumor or a portion thereof is inserted into a hole that substantially matches the tumors diameters. An additional output pore in the box enables lowering the pressure. The excessive gas is cleared up from the box through this output pore as described above. For example, the gas can flow into the box containing the tumor for 2 seconds followed by a suction of the gas for 2 seconds.

An exemplary delivery system comprises an outer lumen or cannula, trocar, tube, etc. An inner lumen or cannula, tube, etc. can be disposed coaxially inside of the outer lumen. The inner lumen is disposed approximately centrally in the outer lumen, although other configurations are also contemplated.

In some embodiments of such an exemplary delivery system, a space, preferably an exhaust space, is between the outer lumen and inner lumen. The exhaust space can be annular or may take any other configuration and/or geometry. A tip can be attached to the inner lumen at the distal end, and is in fluid communication with the inner lumen. In some embodiments, the tip comprises a wire mesh or screen that accesses the space inside of the inner lumen. The delivery device may be advanced to an administration site in the retracted configuration. In some embodiments, the tip is rounded and seals the outer lumen when it is in the retracted position, thus easing insertion of the tip into the body where it is brought adjacent to an administration site.

When the tip of the system is brought adjacent to an administration site, the system is adjusted to its extended configuration in order to affect the administration of the gNO. In the extended configuration, an exhaust path is opened between the distal end of the outer lumen and the tip. gNO is delivered through the inner lumen. The gNO exits the inner lumen at the tip that is in fluid communication with the inner lumen. A wire mesh or screen at the distal end of the tip may assist in diffusing the gNO gas as it exists the device. The exhausted gNO gas returns to the device at the exhaust path. In embodiments, a vacuum is applied to the exhaust space between the outer lumen and the inner lumen in order to attract the exhausted gNO. The exhausted gNO is then brought through the exhaust space to exit the body and be disposed of appropriately. In this way, the device is capable of scavenging gNO from an administration site.

In an alternative configuration, the flow of gNO could be reversed such that gNO is delivered through the space between the outer lumen and inner lumen and removed from the administration site through the inner lumen. In this alternative configuration, a vacuum can be applied to the inner lumen and a positive pressure of gNO is applied to the space defined by the inner and outer lumens. In another alternative, the tip is permanently secured to the outer lumen as well as the inner lumen, such that the tip does not have retracted and extended configurations. In this alternative, permanent passages are provided in the outer lumen for gNO to be expelled from the device or sucked into the device by vacuum. For example, the permanent passages could be small holes or slits radially disposed around the outer lumen, preferably near the distal end of the outer lumen so as to be near the tip of the device.

According to some of any of the embodiments described herein, a delivery device is attached to the end of an endoscope or bronchoscope (e.g. a blue-fluorescence endoscope or bronchoscope) so that the insertion of the delivery device into the body, advancement towards the administration site, and retraction from the body can be visually observed by or otherwise made known to the operator or someone working in concert with the operator. Alternatively, the delivery device can be attached to a guidewire in order to more effectively insert, advance, and retract the device. Additionally, the device can be coated with a fluoroscopic material or have one or more fluoroscopic tags attached to it so that its insertion, advancement, and retraction could be fluoroscopically observed.

In some embodiments, a system for delivering gNO to and scavenging gNOx from, one or more administration sites is intended to fit over the distal end or tip of an endoscope or bronchoscope. The device can be, for example, annular-shaped, having a hole in or about its center and is approximately circular in shape. The hole is preferably sized to accommodate the distal end of an endoscope or broncho-scope. For example, the hole is from about 0.5 cm to about 10 cm in diameter. The hole can be sized so as to fit snugly over the distal end of an endoscope or bronchoscope.

According to some of any of the embodiments described herein, the delivery system comprises a double-needle system in which a suction needle is located adjacent or proximal to the gas delivery needle (e.g., a distance of between 3 mm and 1 cm). The suction needle can decrease or maintain intra-tumoral pressure. Further, two or more needles can be spaced at least about 2 mm apart. gNO can be delivered at a flow rate of at least about 0.01 LPM as described herein. The needles can be designed to have holes along the length of the needle. In example, the diameter of the holes is about 1 mm and disposed every 2 mm. The needles can be disposed within a lumen, placed outside of the tumor mass, while the shaft of the needle can be placed inside the tissue. The length of the needles can be selected to be at least half the tumor's longest dimension. Vacuuming gas through one or more suction needles or holes can be done in a pulsed or continuous manner, preferably synchronized with gNO administration. For example, the gNO can flow into the tumor for 2 seconds followed by applying a vacuum or suction for 2 seconds. One or more, such as a plurality, of needles or an array of needles, such as nano-sized or micron-sized needles can be used. In some embodiments, the gas is injected into the tumor by means of an array of needles with a spacing of about 0.5 cm. The ratio of suction needles and delivery needles can be 1:10 to 10:1, preferably 1:1. The suction needles can be designed to remove less than about 1 liter per minute per cm gas or fluid.

According to some of the any of the embodiments described herein, gNO is applied to a targeted tumor through one or more intra-tumoral channels. For example, a channel 2 mm in width respective to every 4 mm of tissue can be formed through which gas can be delivered, for example at a flow rate higher than 0.01 LPM, directly to the tumor mass by a needle that is placed at the center of each channel, while the gas is cleared up from a scavenging channel. The flow rate in the scavenging channel can be lower than the delivery channel, such as at least 0.001 LPM less than the gNO delivery flow rate. The vacuuming can be accomplished through suction needles or hoses and can be pulsed or continuous, preferably synchronized with gNO administration. For example, the gNO can flow into the tumor for 2 seconds followed by a suction of the gas for 2 seconds.

According to some of the any of the embodiments described herein, gNO is sprayed onto a targeted tumor, optionally when a method as described herein is used in combination with surgical treatment (e.g., tumor resection) and/or in combination with gNO intra-tumoral injection and/or when the tumor is inoperable, flat or amorphous.

In an exemplary method, such as shown in FIGS. 35A-C, the targeted tumor is pre-treated by spraying gNO before the removal of the tumor. The dose can be sufficient to change the color of the tumor to a dark red-block color. gNO administration can optionally continue during the surgery and/or the surrounding area after the tumor is removed. The spray can be maintained for at least about 10 minutes. The spray can be applied to a physiological cavity containing the tumor, such as abdominal cavity. Excess gas can be vacuumed.

According to some embodiments of a delivery system, the delivery device is or comprises a capping configuration, and a gas tubing is connected to the capping configuration, as described in further detail hereinunder. For example, the capping configuration can have two or more layers as described herein. The gNO can be connected to a first layer and the NOx suction can be connected to a second layer.

The following describes exemplary configurations of a delivery system and of methods employing same in the context of the methods and uses as described herein in any of the respective embodiments. Additional exemplary configurations are described in the Examples section that follows.

Referring in this regard to the figures, FIG. 22 is a schematic illustration of a delivery system in which gaseous NO is stored in a cylinder 1 with a valve 2 such as, but not limited to, a one-way valve, on top of it, which is connected to a pressure regulator 3.

Cylinder 1 is optionally and preferably disposable. This is particularly advantageous when the gas is toxic, as in the case of gNO, so that the disposable cylinder can be connected to the delivery system immediately before treatment, and disposed immediately after treatment, thus reducing the time at which the toxic substance is in the treating or operating room. In various exemplary embodiments of the invention the volume of cylinder 1 is sufficiently small so that the amount of gas in cylinder 1 is no more than the typical gas dose to be delivered to the tissue. This is particularly advantageous when the gas is toxic, as in the case of gNO, because in the event of undesired leakage of the gas into the treating room, the total amount of gas that can be leaked is small, compared to the size of the room, thus reducing the risk of inhaling a hazardous concentration of the gas by the subject or medical personnel.

A digital flow controller 5 is connected to the pressure regulator 3 by a designated gas tubing 4. gNO is delivered to an exposure box 7 by a gas tubing 6 that is connected to the box 7 at its distal end and to flow controller 5 at its proximal end. The tumor is placed inside box 7 before gNO delivery. gNO is then delivered to box 7 while excessive gas is evacuated by suctioning through a designated gas tubing 8 to an evacuation system that is preferably connected to the medical center pipe to allow releasing of the gas outside (not shown).

The suctioning of the gas can be done in a pulsed or continuous manner, preferably synchronized with gNO administration. Purging of the gNO delivery system; including the pressure regulator 3, the digital flow controller 5, the exposure box 7 and the tubing lines 4, 6, and 8 can be performed before and/or after treatment. Nitrogen can be used as an exemplary purge gas for purging the system. The purge gas can be introduced from a separate cylinder, as further detailed hereinbelow in the description accompanying FIG. 24.

Figure 23:
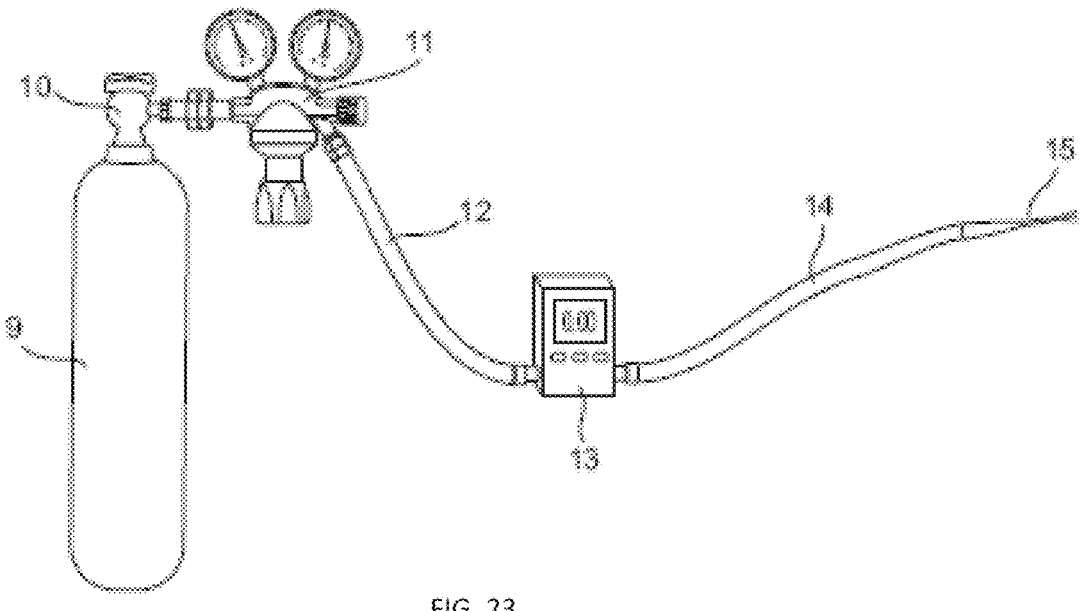
FIG. 23 illustrates an exemplary intra-tumoral delivery system of gNO by a needle, according to some embodiments of the present invention.

FIG. 23 presents a schematic illustration of a delivery system in which gNO is delivered into the tumor or to a physiological cavity containing the tumor by a needle 15. Components 9-14 are same as 1-6 as shown in FIG. 22, respectively.

Figure 24:
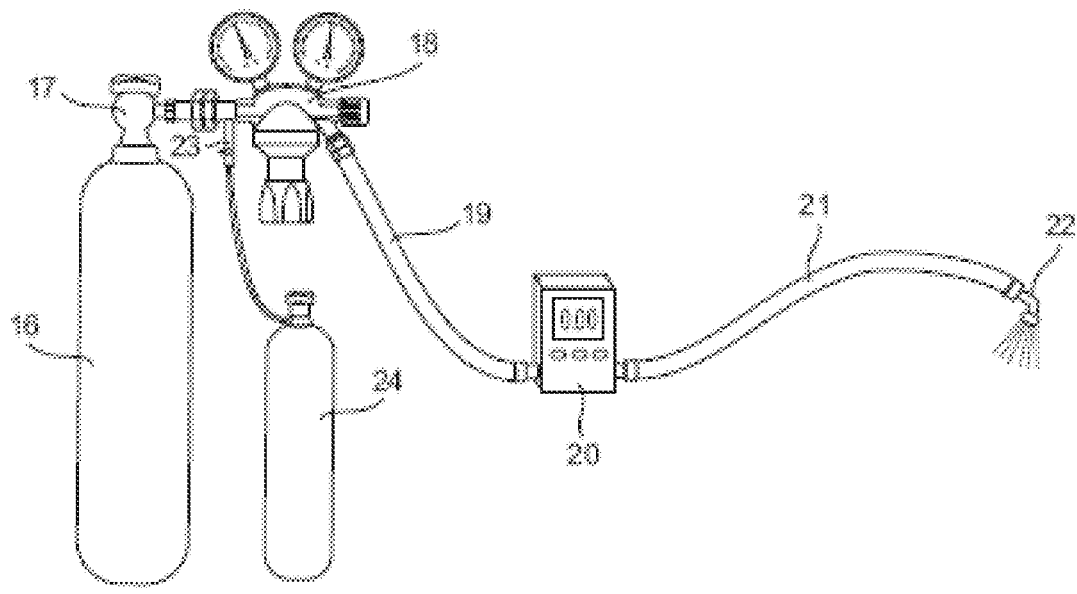
FIG. 24 illustrates an exemplary system for spraying nitric oxide, according to some embodiments of the present invention.

FIG. 24 presents a schematic illustration of a delivery system in which gNO is delivered onto a tumor's surface or into a physiological cavity containing the tumor by spraying. Components 16-21 are the same as components 1-6, respectively, in FIG. 22. The delivery system illustrated in FIG. 24 comprises a delivery device 22 that configured for spraying the gNO to a tumor's surface or into the physiological cavity that contains or is covered with the tumor. The delivery system can comprise a second cylinder 24 designated for purging the accumulated gas in the pressure regulator 18. and optionally and preferably one or more other components of the system, such as, but not limited to, the designated gas tubing(s) 19 and 21, and/or the flow controller 20. The release of the accumulated gas is done automatically, electronically or manually by a valve 23.

Second cylinder 24 may purge the accumulated gas by introducing into the designated gas tubing(s) of the system (e.g., tubing 19 and optionally tubing 21) a purge gas, optionally and preferably an inert purge gas, such as, but not limited to, nitrogen. The purge operation may begin by operating valve 23 to release the purge gas from the second cylinder 24 into the designated gas tubing(s) and prevent release of gNO from first cylinder 16 into the designated gas tubing(s). The purge gas washes the designated gas tubing(s), the pressure regulator 18, and the flow controller 20, from gNO remnants and other substances (e.g., oxygen) that can react with the gNO. Preferably, the purging is for a predetermined time period, e.g., at least 1 minute. In some embodiments of the present invention the purging includes multiple pressurize and depressurize cycles, followed by continuous flow of the purge gas. The Inventors found that such a protocol speeds up the purge and ensures that gas remnants and other substances are more effectively washed out, even from dead ended gas pathways and corners. In some embodiments of the present invention the depressurizing parts of the cycles includes application of vacuum to the gas flow lines. This can be done, for example, by temporarily connecting one of the ports of the valve 23 to a vacuum source (not shown). Alternatively, the valve 23 can include an additional port to which the vacuum source is connected, and the depressurizing parts of the cycles can include switching the valve to a state in which fluid communication is established between the additional port and the tubing 19.

While FIG. 24 illustrates cylinder 24 as smaller in size than cylinder 16, this need not necessarily be the case, since, for some applications, it may be desired to make a cylinder substantially smaller in size than cylinder 24, particularly when cylinder 16 is sufficient small so that the amount of gas in the cylinder is not more than the typical gas dose to be delivered to the tissue, as further detailed hereinabove. Further, while the second cylinder 24 is only illustrated in FIG. 24, it is to be understood, that preferred embodiments of the present invention, such or similar second cylinder 24 can be incorporated in any of the delivery systems described herein, such as, but not limited to, the systems and configurations of the embodiments illustrated in FIGS. 22, 23, 25, 26, 27, 28, 29, 30, 31, 32, 33, 34, 35A-C, 36, and 38.

Figure 25:
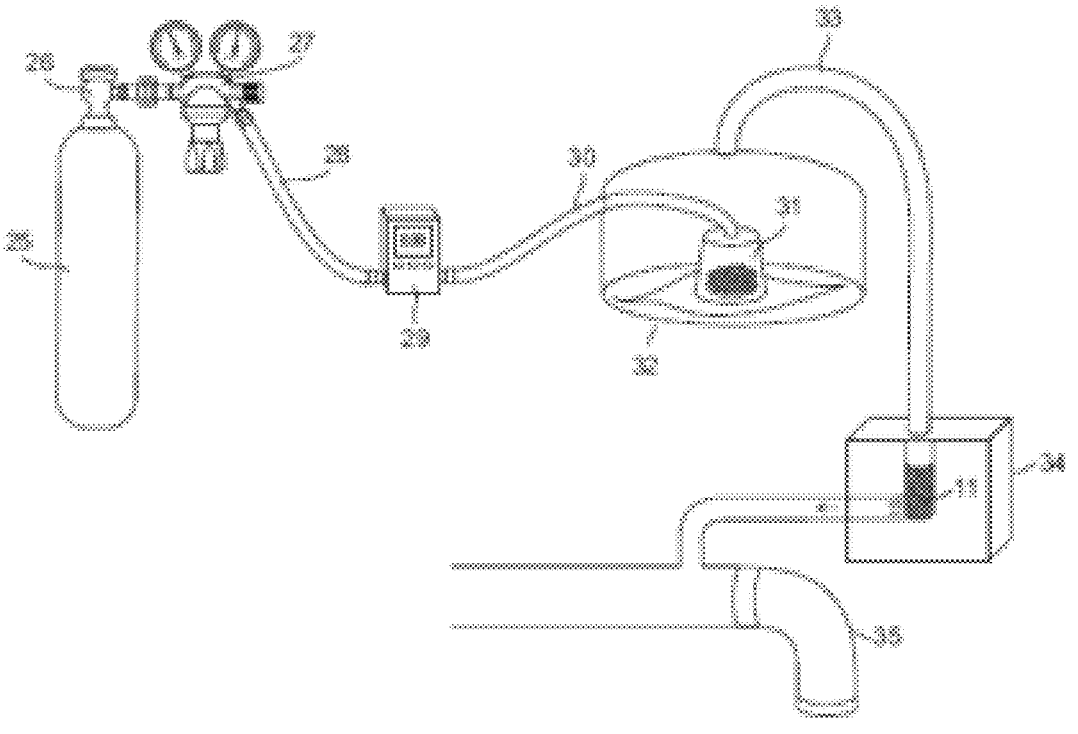
FIG. 25 illustrates an exemplary nitric oxide delivery to the tumor by capping of an outgrowth, according to some embodiments of the present invention.

FIG. 25 presents a schematic illustration of a delivery system in which gNO is delivered by means of a cap 31. Components 25-30 are same as components 1-6 shown in FIG. 22. When such a system is operated, gNO is delivered directly to the tumor's outer layer by cap 31 that covers the tumor and is placed inside a sealed cap 32 that is connected to a gas tubing 33 through which excessive gas is evacuated by suctioning and is optionally and preferably also filtered by a filter 34 (e.g., a tube filled with soda lime, available under the tradename Sofnolime), filtering out gNO and optionally also NOx from the gas mixture coming out of the tumor cap 31 to release clean air. Typically, the clean air is released into the pipes 35 of the medical center.

Figure 26:
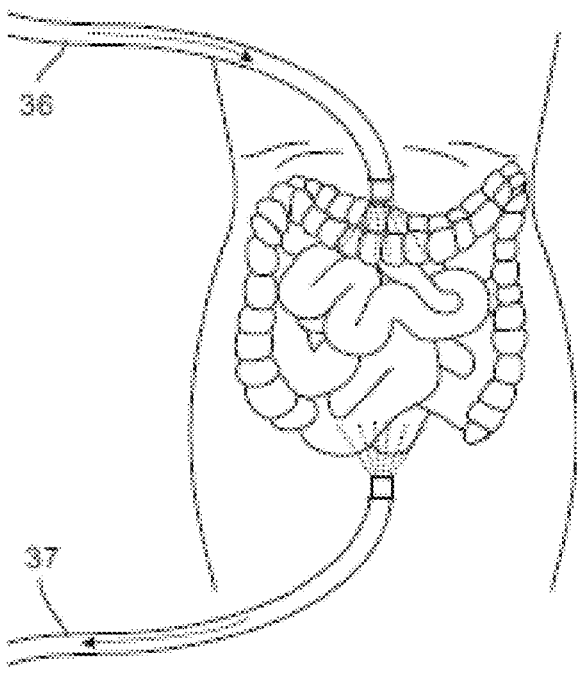
FIG. 26 illustrates an exemplary laparoscope-guided gNO administration and evacuation from the tumor site, according to some embodiments of the present invention.

FIG. 26 presents a schematic illustration of an exemplary configuration comprising a double gas tubing system using a gNO releasing laparoscope 36 for delivering gNO directly to the tumor site and an evacuation gas tubing 37 for immediate removal of excessive gas at its surroundings. Such a configuration is exemplified in FIG. 26 with spraying delivery devices but can alternatively use a needle (see FIG. 23) or any other delivering device mounted at the distal end of laparoscope 36.

Figure 27:
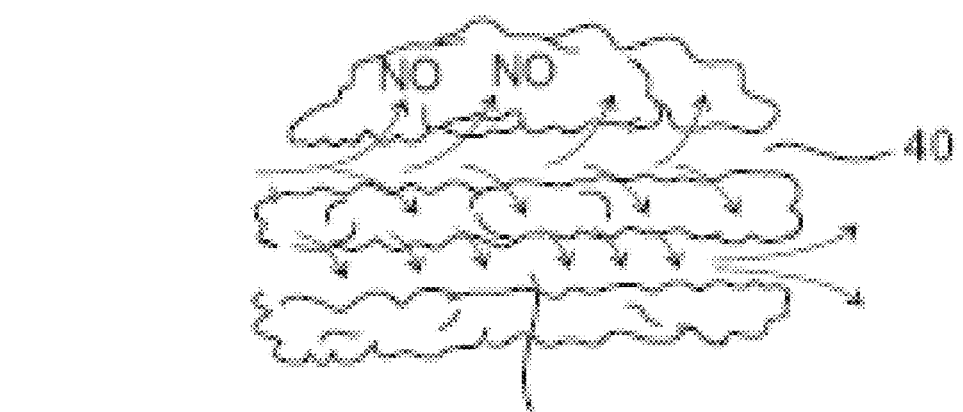
FIG. 27 illustrates an exemplary double intra-tumoral channel system for administering and removal of gNO, according to some embodiments of the present invention.

FIG. 27 presents a schematic illustration of an exemplary configuration in which a gas delivery channel 40 is placed inside the tumor. To control the intra-tumoral pressure, excessive gas is evacuated through an intra-tumoral gas-scavenging channel 41 that can be connected to a NOx filtering pump such as described herein.

Figure 28:
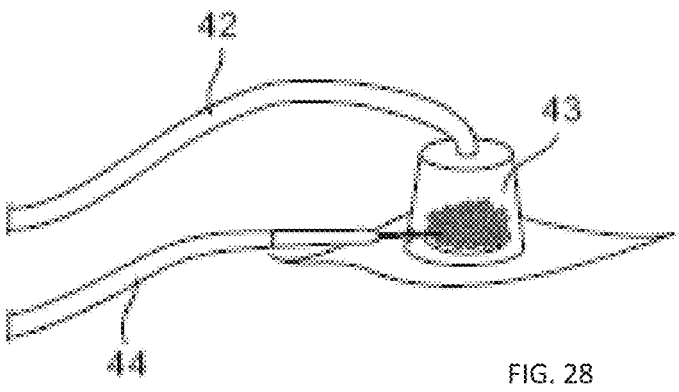
FIG. 28 illustrates an exemplary needle-capping gNO exposure system providing both intra- and out-tumor gas, according to some embodiments of the present invention.

FIG. 28 presents a schematic illustration of a configuration that combines two of the aforementioned delivery methodologies, which can increase (e.g., maximize) the number of gNO exposed cancer cells during treatment. gNO is delivered from a cylinder (such as shown in FIG. 22, 23 or 24) to a gas tubing 42 that is connected to a cap 43 that covers the entire tumor mass; while the tumor cells are at the same time treated by means of a needle 44 as a delivery device.

Figure 29:
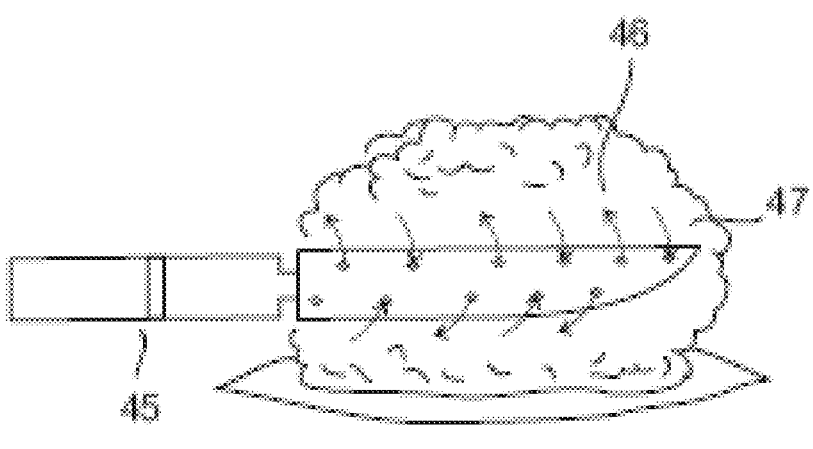
FIG. 29 illustrates an exemplary perforated scalpel for tumor excision with gNO delivery, according to some embodiments of the present invention.

FIG. 29 presents a schematic illustration of a configuration in which gNO treatment is combined with a surgical procedure, in which a tumor is excised while using a gNO-releasing scalpel. The scalpel components include a holder 45, gNO releasing pores 46 that are in fluid communication with a gNO reservoir (not shown), and gas evacuation pores 47 that are connected to NO and NOx filtering pump as described herein (not shown). The vacuuming of the gas can be done in a pulsed or continuous manner.

Figure 30:
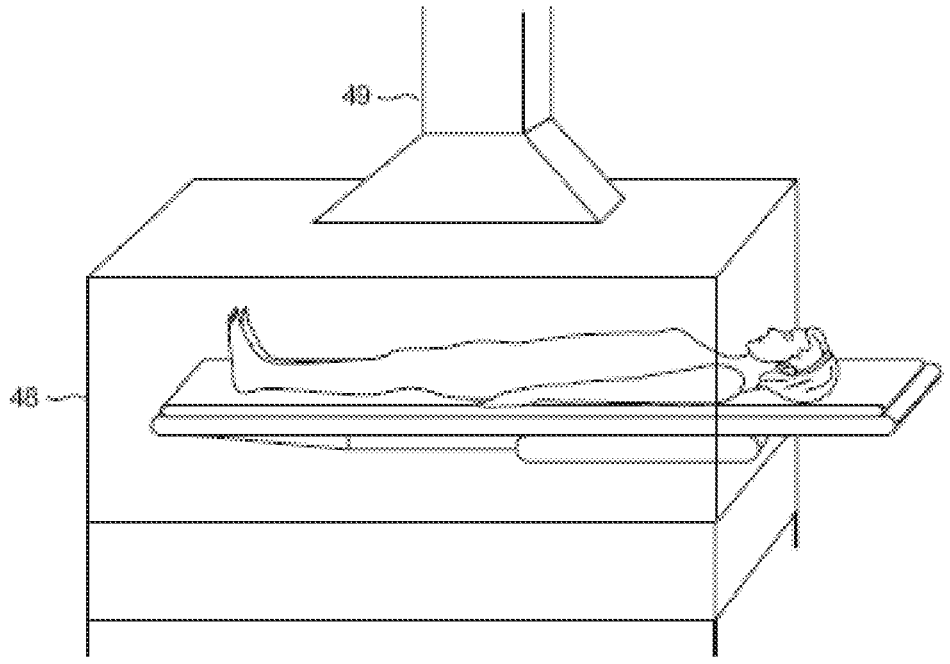
FIG. 30 illustrates an exemplary full-body chemical hood with gNO and NOx vacuuming, according to some embodiments of the present invention.

FIG. 30 presents a schematic illustration of a configuration in which a human subject is placed inside a chemical hood 48 equipped with a NO and NOx filtering pump 49.

Such a configuration can be used with any of the systems and methods as described herein.

Figure 31:
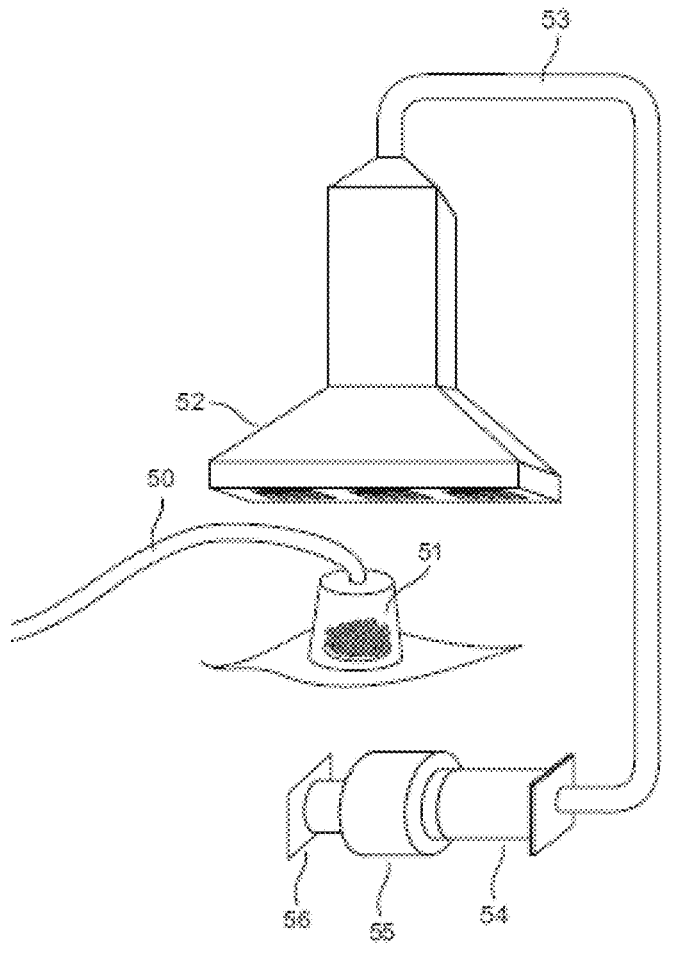
FIG. 31 illustrates an exemplary chemical vapor for local gas extraction which is located above the tumor, according to some embodiments of the present invention.

FIG. 31 presents a schematic illustration of a configuration in which gNO is delivered to the tumor via a tubing 50 connected to a capping 51 which covers tumor cells. To enable evacuation of NO and NOx from the tumor surrounding, a chemical hood 52 is placed directly above capping 51, and is connected to a gas tubing 53, which in turn is connected to a pump (not shown) via an NO and NOx filtering system 54-56.

Figure 32:
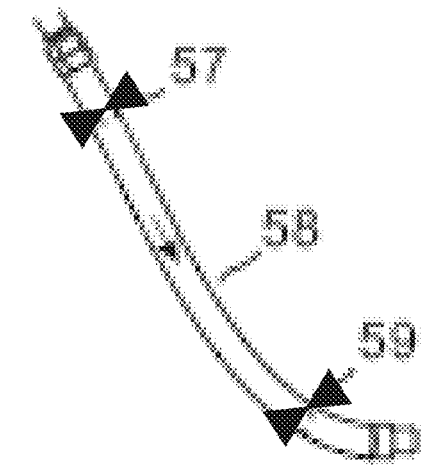
FIG. 32 illustrates an exemplary one-way gas delivering valve, according to some embodiments of the present invention.

FIG. 32 presents a schematic illustration of a one-way valve 57 that is placed nearby the main valve of the gNO cylinder (not shown) and is in fluid communication with a gas tubing 58, which in turn is in fluid communication with an additional one-way valve 59 located at the end of tubing 58 and nearby the delivery device (not shown).

Figure 33:
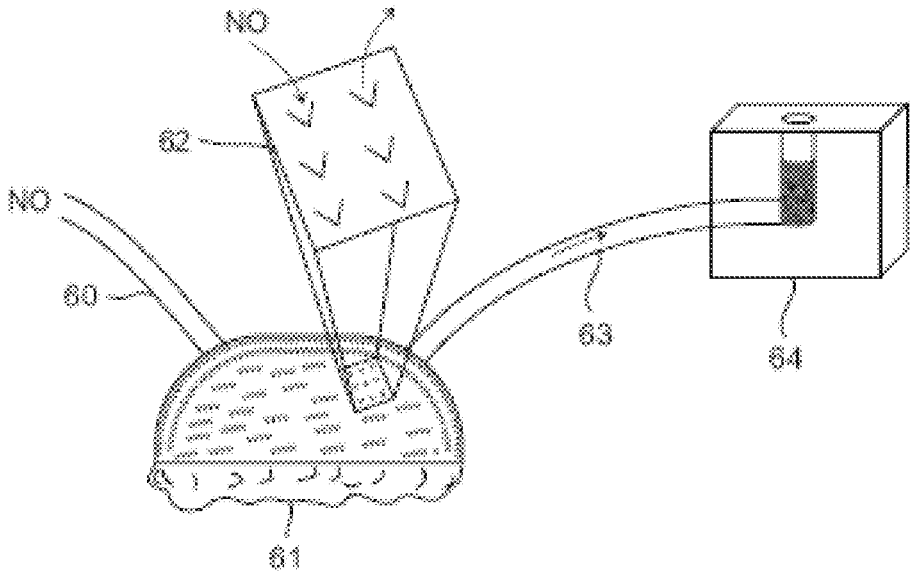
FIG. 33 illustrates an exemplary gaseous NO delivery and scavenging patch, according to some embodiments of the present invention.

FIG. 33 presents a schematic illustration of a configuration in which gNO is supplied to a gas tubing 60 that is connected to patch 61 having a plurality of needles 62 (shown in an enlarged form) on its surface. Needles 62 include gNO input needles and gas output needles for a rapid clear up of excessive gas. The output needles are connected to a suction tubing 63 that is connected to a pump (not shown) via an NO and NOx filter 64.

Figure 34:
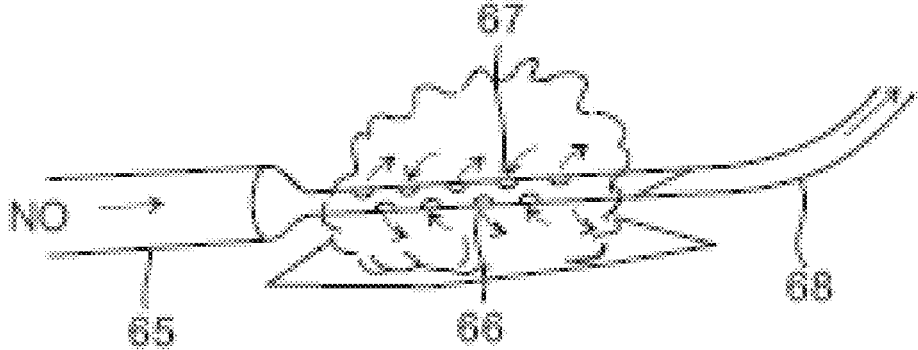
FIG. 34 illustrates an exemplary gNO perforated spray needle, according to some embodiments of the present invention.

FIG. 34 presents a schematic illustration of an exemplary configuration in which gNO is delivered through a device 65 that includes a perforated spray intra-tumoral needle with input pores 67 and output pores 66. NO and NOx clear-up is performed via a gas tubing 68 which is connected to the lumen of device 65 and to a pump via an NO and NOx filter (not shown).

FIGS. 35A-C presents a schematic illustration of an exemplary configuration in which gNO local administration is used in combination with a surgical procedure (tumor excision or resection). FIG. 35A illustrates an exemplary embodiments of this configuration including a delivery system, such as, but not limited to, the delivery system described in FIG. 25, with components 69-72 being the same as components 30-33, respectively. In operation I, gNO is delivered to the tumor site with capping 71. In operation II (FIG. 35B), during the surgical procedure, at least a portion of a tumor is exposed and gNO is applied, for example, using a spraying tube 73. The operated tumor site is being exposed to gNO spraying 73 while being excised by a scalpel 74, which can be, for example, the scalpel shown in FIG. 29. In operation III (FIG. 35C), post-surgery, the operated site is exposed again to gNO, for example, using a gNO spraying tube 75, which can be the same or different from spraying tube 73.

FIG. 36 presents a schematic illustration of an exemplary configuration which involves identifying a presence of a tumor with an imaging apparatus 77 and locally administering to the tumor gNO with a gNO delivery system 78.

According to some of any of the embodiments described herein, the methods and delivery systems as described herein are used in combination with an imaging technique or device which is used to guide and position the delivering device. Such imaging techniques include, for example, computed tomography (CT), ultrasound (US), magnetic resonance imaging (MRI), and any other imaging device or imaging involving procedure, such as used during laparoscopy, bronchoscopy and others.

Uses:

As discussed herein and is demonstrated in the Examples section that follows, the present inventors have demonstrated that locally administering high dose, and preferably low volume, of gNO to a tumor, as described herein in any of the respective embodiments, results in a myriad of therapeutic, as well as prophylactic, advantageous effects.

Embodiments of the present invention relate to methods and uses of local administration of high dose gNO for treating and/or controlling a tumor tissue easily, safely and effectively. As clearly demonstrated in the Examples section that follows, the methodology of the present embodiments is clearly superior to prior art methods in that it can be used to directly destroy primary tumors and facilitates the destruction of metastatic and/or recurrent secondary tumors by, for example, eliciting an anti-tumoral immune/inflammatory response.

As exemplified in FIGS. 1-8C, contacting various cancer cell lines with gNO at a high dose, as described herein, resulted in substantial effect on the viability of all tested cell lines.

As exemplified in FIGS. 9-14 and 20, shrinkage of tumor volume was observed upon exposure to high dose gNO treatment, both in vivo and ex vivo, and when combined with surgery.

As exemplified in FIGS. 15A-17B and 21A-D, local administration of high dose gNO as described herein stimulated an anti-tumor immune response, as demonstrated in various in vivo challenge assays.

Figure 19:
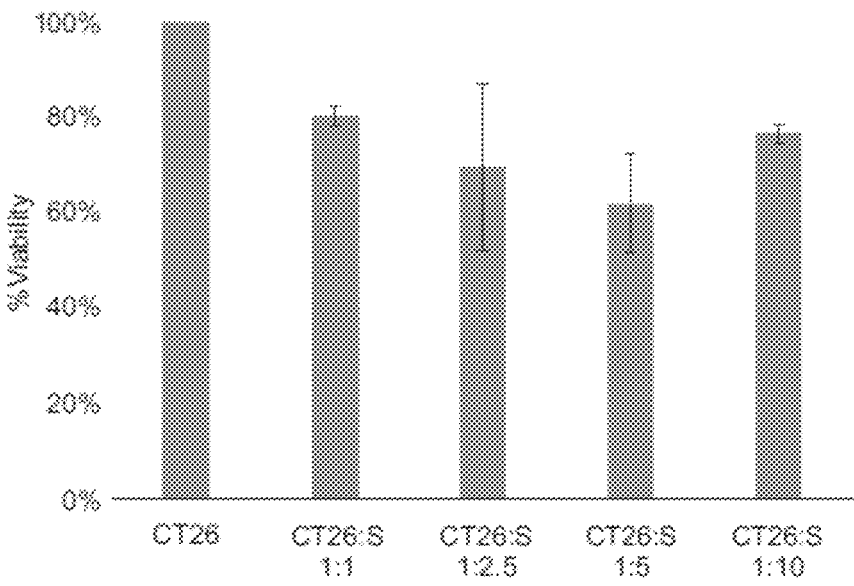
FIG. 19 is a bar graph showing the percentage of CT26 cells viability after incubation with splenocytes extracted from a CT26 gNO-immunized mouse.

As exemplified in FIGS. 18A-19, ex-vivo enrichment of splenocytes extracted of a gNO-treated subject also stimulated an anti-tumor immune response when re-introduced to the subject, as demonstrated in in vivo challenge assays.

These data clearly show the advantages of local administration of gNO at a high dose as described herein in controlling, inhibiting and even vaccinating against tumors.

The methods and uses described herein which employ local administration of gNO can be considered as tumor ablation.

According to an aspect of some embodiments of the present invention, there is provided a method of inhibiting growth of cells or tissue of a tumor in a subject (a subject afflicted by the tumor), which is effected by locally administering gNO to the tumor at a high dose as described herein in any of the respective embodiments.

According to an aspect of some embodiments of the present invention, there is provided gNO for use in inhibiting growth of cells or tissue of a tumor in a subject (a subject afflicted by the tumor), wherein the gNO is locally administered to the tumor at a high dose as described herein in any of the respective embodiments.

According to an aspect of some embodiments of the present invention, there is provided a high dose of gNO for use in inhibiting growth of cells or tissue of a tumor in a subject (a subject afflicted by the tumor), wherein the gNO is locally administered to the tumor as described herein in any of the respective embodiments.

According to an aspect of some embodiments of the present invention, there is provided a use of gNO as a medicament for inhibiting growth of cells or tissue of a tumor in a subject (a subject afflicted by the tumor), wherein the gNO is locally administered to the tumor at a high dose as described herein in any of the respective embodiments.

According to an aspect of some embodiments of the present invention, there is provided a use of a high dose of gNO, as described herein in any of the respective embodiments, as a medicament for inhibiting growth of cells or tissue of a tumor in a subject (a subject afflicted by the tumor), wherein the gNO is locally administered to the tumor as described herein in any of the respective embodiments.

As used herein throughout, the term "tumor" describes a plurality of cells or a tissue composed of the plurality of cells that are characterized by abnormal cell growth and which serve no physiological function.

By "abnormal cell growth" it is meant uncontrolled, progressive proliferation of the cells, which is no longer under normal bodily control. The growth of a tumor tissue typically exceeds, and is uncoordinated with, that of the normal cells or tissues around it.

"Abnormal cell growth" also describes cell growth that is independent of normal regulatory mechanisms (e.g., loss of contact inhibition), including, for example, abnormal growth of: (1) cancerous (or cancer) cells that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "tumor" is also referred to herein and in the art as "neoplastic tissue" encompasses benign, pro-malignant and malignant tumors.

The phrase "cell growth", as used herein, for example in the context of "tumor cell growth", unless otherwise indicated, is used as commonly used in oncology, where the term is principally associated with growth in cell numbers, which occurs by means of cell reproduction (i.e., proliferation) when the rate of the latter is greater than the rate of cell death (e.g., by apoptosis or necrosis), to produce an increase in the size of a population of cells, although a small component of that growth may in certain circumstances be due also to an increase in cell size or cytoplasmic volume of individual cells.

An agent that inhibits cell growth can thus do so by either inhibiting proliferation or stimulating cell death, or both, such that the equilibrium between these two opposing processes is altered.

The term "tissue" describes an ensemble of cells, not necessarily identical, but from the same origin, that together carry out a specific function.

The phrase "inhibiting cell growth" describes, as indicated above, altering the equilibrium between cells proliferation and cell death such that a rate of cell death is increased and is higher than the proliferation rate, resulting in a reduced or nullified number of viable cells. Thus, this phrase encompasses reducing or inhibiting proliferation of cells, killing cells, and/or reducing a volume of a tissue formed of the cells (a tumor tissue).

The phrase "tumor growth", as used herein, unless otherwise indicated, is principally associated with an increased mass or volume of the tumor, primarily as a result of tumor cell growth.

A tumor as described herein can be a primary tumor or a secondary tumor.

The term "malignant tumor" describes a tumor that is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize).

The term "primary tumor" describes a tumor that is at the original site where it first arose.

The term "secondary tumor" describes a tumor that has spread from its original (primary) site of growth to another site, close to or distant from the primary site, and is also referred to herein and in the art as metastasis, or as metastasizing tumor. The term "secondary tumor" as used herein also describes recurrent tumor, which can ne at the original site as the primary tumor and/or at another site, as a metastasizing tumor.

According to some of any of the embodiments described herein, the tumor is a malignant tumor, for example, a malignant cancerous tumor, and the tumor cells are cancer or cancerous cells.

According to these embodiments, the methods and uses as described herein in any of the respective embodiments are for treating and/or controlling cancer or a cancerous tumor is a subject in need thereof.

The methods and uses as described herein are for treating a subject having a primary cancer tumor, a metastasizing cancer and/or a recurrent cancer, as described herein.

The term "cancer" encompasses malignant and benign tumors as well as disease conditions evolving from primary or secondary tumors, as described herein.

Examples of benign tumors include, without limitation, lipomas, chondromas, adenomas, pilomatricomas, teratomas, and hamartomas.

Cancers treatable according to embodiments of the invention include, but are not limited to, carcinomas, sarcomas, blastomas, and germ cell tumors. Carcinomas include, without limitation, adenocarcinomas (e.g., small cell lung cancer, kidney, uterus, prostate, bladder, ovary and/or colon adenocarcinoma) and epithelial carcinomas.

Examples of cancers treatable according to embodiments of the invention include, without limitation, adenocarcinoma, adrenal tumors (e.g., hereditary adrenocortical carcinoma), biliary tract tumors, bladder cancer, bone cancer, brain cancer, breast cancer (e.g., ductal breast cancer, invasive intraductal breast cancer, sporadic breast cancer, susceptibility to breast cancer, type 4 breast cancer, breast cancer-1, breast cancer-3, and/or breast-ovarian cancer), bronchogenic large cell carcinoma, cervical cancer (e.g., cervical carcinoma), carcinosarcoma, choriocarcinoma, cystadenocarcinoma, dermatofibrosarcoma protuberans, ductal carcinoma, Ehrlich-Lettre ascites, embryonal rhabdomyosarcoma, endocrine neoplasia, endometrial cancer (e.g., endometrial carcinoma), ependimoblastoma, epidermoid carcinoma, epithelial adult tumor, epithelioma, erythroleukemia (e.g., Friend and/or lymphoblast), extraskeletal myxoid chondrosarcoma, fibrosarcoma, gallbladder carcinoma, ganglioblastoma, gastrointestinal tract tumors (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6, hereditary nonpolyposis type 7, small and/or large bowel carcinoma, esophageal carcinoma, tylosis with esophageal cancer, stomach carcinoma, pancreatic carcinoma, and/or pancreatic endocrine tumors), germ cell tumor (male germ cell tumor, and/or testicular and/or ovarian dysgerminoma), giant cell tumor, glial tumor, glioma, glioblastoma (e.g., glioblastoma multiforme, astrocytoma), head & neck cancer, heterohybridoma, heteromyeloma, histiocytoma, hybridoma (e.g., B-cell), hypernephroma, insulinoma, islet tumor, keratoma, large cell carcinoma, leiomyoblastoma, leiomyosarcoma, leukemia (e.g., acute lymphatic leukemia, acute lymphoblastic leukemia, acute lymphoblastic pre-B cell leukemia, acute lymphoblastic T cell leukemia, acute megakaryoblastic leukemia, monocytic leukemia, acute myelogenous leukemia, acute myeloid leukemia, acute myeloid leukemia with eosinophilia, B-cell leukemia, basophilic leukemia, chronic myeloid leukemia, chronic B-cell leukemia, eosinophilic leukemia, Friend leukemia, granulocytic or myelocytic leukemia, hairy cell leukemia, lymphocytic leukemia, mast cell leukemia, megakaryoblastic leukemia, monocytic leukemia, monocytic-macrophage leukemia, myeloblastic leukemia, myeloid leukemia, myelomonocytic leukemia, plasma cell leukemia, pre-B cell leukemia, promyelocytic leukemia, subacute leukemia, T-cell leukemia, lymphoid neoplasm, predisposition to myeloid malignancy, and/or acute nonlymphocytic leukemia), Li-Fraumeni syndrome, liposarcoma, liver cancer (e.g., hepatoblastoma, hepatocellular carcinoma, hepatocellular cancer, and/or hepatoma), lung cancer (e.g., Lewis lung carcinoma, small cell carcinoma and/or non-small cell carcinoma) lymphoma (e.g., Hodgkin's disease, non-Hodgkin's lymphoma, B-cell lymphoma, diffuse large B-cell lymphoma (DLBCL), Burkitt lymphoma, cutaneous T-cell lymphoma, histiocytic lymphoma, lymphoblastic lymphoma, T-cell lymphoma, and/or thymic lymphoma), lymphosarcoma, lynch cancer family syndrome II, mammary tumor, mastocytoma, medulloblastoma, medullary carcinoma, melanoma, mesothelioma, metastatic tumor, monocyte tumor, mucoepidermoid carcinoma, multiple *glomus* tumors, multiple meningioma, myelodysplastic syndrome, myeloma (e.g., multiple myeloma), nasopharyngeal cancer, nephroblastoma, nervous tissue glial tumor, nervous tissue neuronal tumor, neurinoma, neuroblastoma, neurogenic tumor, non-melanoma skin cancer, oat cell carcinoma, oligodendroglioma, osteochondroma, osteomyeloma, ovarian cancer (e.g., epithelial ovarian cancer, ovarian carcinoma, serous ovarian cancer, and/or ovarian sex cord tumors), papillary carcinoma, papilloma, paraganglioma (e.g., familial nonchromaffin), pheochromocytoma, pituitary tumor (invasive), placental site trophoblastic tumor, plasmacytoma, prostate cancer (e.g., prostate adenocarcinoma), renal cancer (e.g., Wilms' tumor type 2 or type 1), retinoblastoma, rhabdoid tumors (e.g., rhabdoid predisposition syndrome), rhabdomyosarcoma, sacrococcygeal tumor, sarcoma (e.g., Ewing's sarcoma, histiocytic cell sarcoma, Jensen sarcoma, myxosarcoma, osteosarcoma, reticulum cell sarcoma, soft tissue sarcoma and/or synovial sarcoma), schwannoma, small cell carcinoma, spindle cell carcinoma, spinocellular carcinoma, squamous cell carcinoma (e.g., in head and neck), subcutaneous tumor, teratocarcinoma (e.g., pluripotent), teratoma (e.g., immature teratoma of ovary), testicular cancer (e.g. testicular germ cell tumor), transitional cell carcinoma, Turcot syndrome with glioblastoma, thymoma, thyroid cancer (e.g., follicular, medullary and/or papillary thyroid cancer), trichoepithelioma, trophoblastic tumor, undifferentiated carcinoma, uterine cancer, uterine cervix carcinoma.

Methods and uses of the present embodiments can be used to treat one or more solid tumors.

As used herein, the term "solid tumor" refers to those conditions, such as cancer, that form an abnormal tumor mass, such as sarcomas, carcinomas, and lymphomas. For example, solid tumors can include, but are not limited to, ovarian tumors, prostate tumors, skin tumors, lung tumors, breast tumors, liver tumors, brain tumors, CNS tumors, kidney tumors, colon tumors, bladder tumors, intestinal tumors, melanomas, gliomas, ependymomas, oligodendrogliomas, oligoastrocytomas, astrocytomas, glioblastomas, and medulloblastomas. Suitable examples of solid tumor diseases include, but are not limited to, non-small cell lung cancer (NSCLC), neuroendocrine tumors, thyomas, fibrous tumors, metastatic colorectal cancer (mCRC), and the like.

In certain embodiments, the solid tumor disease is an adenocarcinoma, squamous cell carcinoma, large cell carcinoma, and the like.

According to some embodiments, the cancer is or comprises a solid tumor, and can be, for example, adenocarcinoma, adrenal tumors (e.g., hereditary adrenocortical carcinoma), biliary tract tumors, bladder cancer, bone cancer, brain cancer, breast cancer (e.g., ductal breast cancer, invasive intraductal breast cancer, sporadic breast cancer, susceptibility to breast cancer, type 4 breast cancer, breast cancer-1, breast cancer-3, and/or breast-ovarian cancer), bronchogenic large cell carcinoma, cervical cancer (e.g., cervical carcinoma), carcinosarcoma, choriocarcinoma, cystadenocarcinoma, dermatofibrosarcoma protuberans, ductal carcinoma, Ehrlich-Lettre ascites, embryonal rhabdomyosarcoma, endocrine neoplasia, endometrial cancer (e.g., endometrial carcinoma), ependimoblastoma, epidermoid carcinoma, epithelial adult tumor, epithelioma, extraskeletal myxoid chondrosarcoma, fibrosarcoma, gallbladder carcinoma, ganglioblastoma, gastrointestinal tract tumors (e.g., colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6, hereditary nonpolyposis type 7, small and/or large bowel carcinoma, esophageal carcinoma, tylosis with esophageal cancer, stomach carcinoma, pancreatic carcinoma, and/or pancreatic endocrine tumors), germ cell tumor (male germ cell tumor, and/or testicular and/or ovarian dysgerminoma), giant cell tumor, glial tumor, glioma, glioblastoma (e.g., glioblastoma multiforme, astrocytoma), head & neck cancer, heterohybridoma, heteromyeloma, histiocytoma, hybridoma (e.g., B-cell), hypernephroma, insulinoma, islet tumor, keratoma, large cell carcinoma, leiomyoblastoma, liposarcoma, liver cancer (e.g., hepatoblastoma, hepatocellular carcinoma, hepatocellular cancer, and/or hepatoma), lung cancer (e.g., Lewis lung carcinoma, small cell carcinoma and/or non-small cell carcinoma) lymphoma (e.g., Hodgkin's disease, non-Hodgkin's lymphoma, B-cell lymphoma, diffuse large B-cell lymphoma (DLBCL), Burkitt lymphoma, cutaneous T-cell lymphoma, histiocytic lymphoma, lymphoblastic lymphoma, T-cell lymphoma, and/or thymic lymphoma), lymphosarcoma, lynch cancer family syndrome II, mammary tumor, mastocytoma, medulloblastoma, medullary carcinoma, melanoma, mesothelioma, metastatic tumor, monocyte tumor, mucoepidermoid carcinoma, multiple glomus tumors, multiple meningioma, myelodysplastic syndrome, myeloma (e.g., multiple myeloma), nasopharyngeal cancer, nephroblastoma, nervous tissue glial tumor, nervous tissue neuronal tumor, neurinoma, neuroblastoma, neurogenic tumor, non-melanoma skin cancer, oat cell carcinoma, oligodendroglioma, osteochondroma, osteomyeloma, ovarian cancer (e.g., epithelial ovarian cancer, ovarian carcinoma, serous ovarian cancer, and/or ovarian sex cord tumors), papillary carcinoma, papilloma, paraganglioma (e.g., familial nonchromaffin), pheochromocytoma, pituitary tumor (invasive), placental site trophoblastic tumor, plasmacytoma, prostate cancer (e.g., prostate adenocarcinoma), renal cancer (e.g., Wilms' tumor type 2 or type 1), retinoblastoma, rhabdoid tumors (e.g., rhabdoid predisposition syndrome), rhabdomyosarcoma, sacrococcygeal tumor, sarcoma (e.g., Ewing's sarcoma, histiocytic cell sarcoma, Jensen sarcoma, myxosarcoma, osteosarcoma, reticulum cell sarcoma, soft tissue sarcoma and/or synovial sarcoma), schwannoma, small cell carcinoma, spindle cell carcinoma, spinocellular carcinoma, squamous cell carcinoma (e.g., in head and neck), subcutaneous tumor, teratocarcinoma (e.g., pluripotent), teratoma (e.g., immature teratoma of ovary), testicular cancer (e.g. testicular germ cell tumor), transitional cell carcinoma, Turcot syndrome with glioblastoma, thymoma, thyroid cancer (e.g., follicular, medullary and/or papillary thyroid cancer), trichoepithelioma, trophoblastic tumor, undifferentiated carcinoma, uterine cancer, uterine cervix carcinoma.

According to some of any of the embodiments described herein, the gNO is locally administered to the primary tumor and/or to a metastasizing tumor.

According to some of any of the embodiments described herein, depending on the site of the primary or metastasizing tumor, the gNO is locally administered to an organ that hosts the tumor cells or to an organ that is in close proximity (e.g., up to 5 cm or up to 2 cm) to the tumor cells. Exemplary organs to which gNO can be locally administered according to some of any of the respective embodiments as described herein include, but are not limited to, the adrenal gland, bladder, bones, brain, breast, cervix, colon, colorectum, esophagus, gastrointestinal tract, heart, kidney, liver, large intestine, lungs, mouth, ovaries, pancreas, parathyroid, pituitary gland, prostate, salivary gland, skin, small intestine, spleen, stomach, thymus, thyroid, testicles, urinary tract, uterus, or vagina. According to some embodiments, the gNO is locally administered to the liver, in case of a primary liver cancer or of liver metastases.

One of skill in the art will appreciate that the methods and uses provided herein for inhibiting abnormal growth of tumor cells or tissue, and are for treating, controlling, or preventing cancer may be generally applicable to all known or to-be-discovered cancerous cell phenotypes and cancerous growths.

The present embodiments relate to any size and shape of tumors, including large, spread and amorphic cancerous outgrowths.

The methods and uses provided herein may be especially useful for the treatment, control, and/or prevention of tumors (e.g., cancerous tumors) at localized sites, including inoperable tumors, tumors where localized treatment would be beneficial, and solid tumors.

According to some of any of the embodiments described herein, the methods and uses of the present embodiments are for inhibiting growth of cells of a primary tumor.

According to some of these embodiments, a subject as described herein, which has been diagnosed as being afflicted by a tumor, is subjected to the high dose local administration of gNO as described herein in any of the respective embodiments.

Between about 50% and about 100% of the cancerous cells or growth may be killed by the gaseous nitric oxide over the course of one or more administrations, as described herein in any of the respective embodiments.

According to some of any of the embodiments described herein, a method or use as described herein comprises identifying a tumor or cancerous or abnormal cells in a subject (e.g., a mammal, suspected as having tumor), and subsequently, locally administering the gaseous nitric oxide directly to the identified cancerous or abnormal cells as described herein in any of the respective embodiments.

Identifying the presence and location of a tumor can be made by any invasive or non-invasive technique. In some embodiments, the identifying and administering procedures are performed by the same device or system, for example, by an endoscope.

In any of the embodiments described herein, the methods and uses may be useful for the treatment, control, prevention, and/or immunization of growths of cancerous cell phenotype in animal bodies, and preferably in mammalian bodies, and more preferably in human bodies.

In some of any of the embodiments described herein, the subject is a mammal, for example, a human being.

According to some of any of the embodiments described herein, the local administration of gNO can further comprise one or more of the following steps: (a) pre-perforating the tumor or cancerous outgrowth prior to gas administration, (b) delivering the gas by perforated spray needles, (c) delivering the gas in a pulsed manner and/or (d) delivering the gas with a dual needle system, for example, as described herein. Such steps maybe desirable for reducing an increase the intra-tumoral pressure as a result for the gNO local administration, to thereby avoid possible damage to healthy tissues in case the gas leaks out of the tumor.

According to some of any of the embodiments described herein, local administration of gNO, preferably at a high dose, as described herein in any of the respective embodiments stimulates an immunological response to the tumor (an anti-tumor immune response). The stimulation of an immune response provides for inhibiting growth of and/or killing and/or eradicating cells of a primary tumor. The stimulation of an immune response can alternatively or in addition provide for inhibiting growth of and/or killing and/or eradicating cells of one or more metastases of the primary tumor.

Thus, according to some embodiments of the present invention, the gNO can be locally administered to one of the primary tumor site and a site of a metastasis, and this treatment results in stimulation of an immune response to both the primary tumor and the metastasis.

According to some of any of the embodiments described herein, local administration of gNO at a high dose is performed at the primary tumor site, and the appearance of metastases as a secondary tumor is inhibited, reduced or prevented, probably as a result of stimulating an immunological response to the tumor in the subject.

According to some of any of the embodiments described herein, the gaseous NO (gNO) local administration stimulates a systemic anti-tumor immune response that eliminates distant and/or non-treated cancerous sites or cells, other that the site to which gNO is locally administered.

Without being bound by any particular theory, it is assumed that applying high dose nitric oxide directly to the tumor (as described herein) may induce tumor-specific immune responses. Also, partially or entirely ablating primary or secondary metastatic tumors by high dose gNO as described herein may induce necrosis of tumor cells, resulting in the release of antigens and presentation of antigens to the immune system. The released tumor antigens may assist in activating anti-tumor T cells, which can destroy remaining malignant cells in local and distant tumors.

According to some of any of the embodiments described herein, local administration of gNO as described herein is for preventing occurrence, inhibiting growth and/or killing cells of a secondary tumor. The secondary tumor can be a metastasizing tumor and/or a recurrent tumor.

According to some of any of the embodiments described herein, local administration of gNO as described herein is for stimulating in the subject an immunological response to the tumor, thereby inhibiting growth of a primary tumor and/or a secondary tumor.

It is to be noted that inducing or stimulating an anti-tumor immune response, as described herein, does not require complete inhibition of growth or destruction of the cancerous outgrowth. Rather, the local administration of high dose gNO can be performed such that from 1 to 100% of the tumor cells are killed, for stimulating an immune response.

According to some of any of the embodiments described herein, local administration of gNO at a high dose, as described herein in any of the respective embodiments and any combination thereof, to a primary or metastasizing tumor, results in inhibiting growth of the primary and secondary tumor cells, by triggering an anti-tumor immune response in the subject.

According to embodiments of this aspect of the embodiments of the present invention, there is provided a method for vaccinating a subject (e.g., a mammal such as a human being) against cancer (e.g., primary tumor and/or metastases and/or recurrence of a cancer type the subject was afflicted with) comprising exposing to gaseous nitric oxide, preferably, but not obligatory, at a concentration from about 1000 ppm to about 1,000,000 ppm, a solid tumor at one or more administration sites, for a period of time of from about 1 second to 1 hour. Preferably, the gNO concentration is between about 50,000 and 200,000 ppm and the duration of the treatment is 1 second to 5 minutes. For example, the gNO can be administered at about 50,000 ppm. For example, dose between about 10,000 ppm to about 50,000 ppm, or dose between about 50,000 ppm to about 100,000 ppm, or about 100,000 ppm to about 200,000 ppm, or about 200,000 ppm to about 500,000 ppm, or about 500,000 ppm to about 1,000,000 ppm or about 50,000 ppm or about 100,000 ppm or about 200,000 ppm or about 500,000 ppm or about 1,000,000 ppm can be administered.

For any of the methods and uses described herein, excision of the treated tumor or a portion thereof via surgery can be performed, for example, from 1 day to 30 days post nitric oxide treatment, preferably 4 days to 14 days post treatment.

According to some of any of the embodiments described herein, local administration of gNO at a high dose, as described herein in any of the respective embodiments and any combination thereof, is followed by isolating from the subject a sample which includes anti-tumor immune cells. This sample can be used for providing a composition that is enriched by the immune cells, which is then re-introduced to the subject's body for further stimulating the immunological response to the tumor, to thereby reduce, inhibit or prevent growth of cells of a secondary tumor (e.g., a metastasizing tumor and/or a recurrent tumor).

According to an aspect of some embodiments of the present invention there is provided a method of inducing an immunological response to a tumor in a subject afflicted by the tumor. The method, according to these embodiments, comprises locally administering gNO to the tumor, as described herein, preferably, but not obligatory, at a high dose, as described herein; and subsequently isolating immune cells from the subject.

The isolated immune cells can then optionally be allowed to proliferate and/or are purified, and are re-introduced to the subject, to thereby stimulate the anti-tumor immune response in the subject.

According to some of any of the embodiments of this aspect of the present invention, the immune cells are derived from a sample drawn from a blood organ of the subject, for example, from a blood sample or from a blood lymphatic organ of the subject. Alternatively, or in addition, the immune cells are derived from a tumor sample, which can be obtained, for example, during a surgery as described herein, or from a biopsy, and is preferably obtained upon exposure to local administration of gNO as described herein.

According to some of any of the embodiments of this aspect of the present invention, the immune cells comprise leukocytes, for example, leukocytes isolated from a blood sample drawn from subject, a blood lymphatic organ of the subject and/or from the tumor.

The sample from which the immune cells are isolated is preferably drawn from the subject at least one day, preferably at least 4 days after the gNO treatment, for example, from 1 to 21, or from 4 to 21, or from 7 to 21, days, after a first local administration of gNO.

Isolating the immune cells (e.g., leukocytes) from a sample drawn from the treated subject can be made by techniques known to those skilled in the art.

According to some of any of the embodiments of this aspect of the present invention, subsequent to isolating the immune cells from the sample drawn from the subject, and prior to re-introducing the immune cells to the subject, the method further comprises proliferating and/or purifying the immune cells (e.g., leukocytes). Proliferating the immune cells can be performed by culturing the immune cells is a culturing medium under conditions that allow or promote proliferation, using techniques known in the art. Purification can be performed prior to or subsequent to the proliferation, using techniques known in the art.

The isolated immune cells, optionally upon further proliferation and/or purification, can be used immediately upon being processed as described herein, or can be preserved, and used when desired.

According to some embodiments, the tumor is a primary tumor and the method is for inhibiting growth and/or killing cells or tissue of the tumor.

According to some embodiments, the tumor is a primary tumor and re-introducing the immune cells to the subject is performed upon occurrence of a metastatic event and/or recurrence of the tumor, for inhibiting growth of a secondary tumor (inhibiting growth of cells of a secondary tumor as described herein).

In exemplary embodiments, at least one day post a first treatment with locally administered gNO, for example, within 1 to 21, or 4 to 21 days, or 7 to 21 days, post gNO local administration treatment, leukocytes from the patient are extracted (preferably from blood, draining lymph node or the treated tumor itself). Among these leukocytes, there are anti-cancer immune cells. Without wishing to be bound to any particular theory, these anti-cancer immune cells can specifically recognize tumor and/or cancer cells from the tumor that was treated but potentially can also recognize antigens that are expressed on different tumor types (cross-reaction).

After proliferation and purification of these leukocytes outside the patient body (ex-vivo), these cells are injected back to the patient, for example, to fight against remaining cancer cells in the patient's body (e.g., distant metastases that were not fully treated following the first gNO treatment, and/or cells of the primary tumor that were not killed). These immune cells have both preventive (prophylactic) and therapeutic effect.

According to some of any of the embodiments of this aspect, locally administering gNO to the subject is at a high dose, as described herein in any of the respective embodiments, and according to some of these embodiments, gNO is administered intra-tumorally (e.g., by injection). In some embodiments, a method or a use as described herein is for boosting the immune system of a subject against cancer.

In some of any of the embodiments described herein, the method or use comprises two or more weekly treatments. Optionally, each treatment comprises local administration of gNO to a different location on or within the tumor. In some embodiments, a first treatment is for the primary tumor and a second treatment the following week targets a metastasis. Subsequent treatments can be for the primary tumor, metastases, or combinations thereof. In some embodiments, the method comprises 10 gNO treatments.

According to an aspect of some embodiments of the present invention there is provided a composition which comprises immune cells isolated from a subject afflicted by a tumor upon exposing at least a portion of the tumor to local administration of gaseous NO, e.g., as described herein in any of the respective embodiments.

In some embodiments, the immune cells are isolated upon exposing the subject to local administration of gNO, preferably at a high dose, as described herein in any of the respective embodiments, for example, by intra-tumoral administration of gNO to the subject.

In some embodiments, the composition comprises anti-cancer immune cells purified from leukocytes extracted from a patient subjected to the gNO local administration as describe herein.

In some embodiments, the immune cells produced by a subject subjected to the gNO local administration as described herein are preserved. In some embodiments, a method is provided for the preservation of the immune cells purified from leukocytes extracted from a subject subjected to the gNO local administration described herein.

The ability to preserve the immune cells is important for their use in clinical and research applications. Preservation of cells permits the transportation of cells between locations, as well as completion of safety and quality control testing. Preservation also permits the development of a 'manufacturing paradigm' for cell therapies, thereby maximizing the number of products that can be produced. The immune cells can be purified by any method known in the art.

In some embodiments, the immune cells are preserved by cryopreservation. Cryopreservation agents which can be used include, but are not limited to, dimethyl sulfoxide (DMSO) (Lovelock and Bishop, 1959, Nature 183: 1394-1395; Ashwood-Smith, 1961, Nature 190: 1204-1205), glycerol, polyvinylpyrrolidone (Rinfret, 1960, nn. N.Y. Acad. Sci. 85: 576), polyethylene glycol (Sloviter and Ravdin, 1962, Nature 196: 548), albumin, dextran, sucrose, ethylene glycol, i-erythritol, D-ribitol, D-mannitol (Rowe et al., 1962, Fed. Proc. 21: 157), D-sorbitol, i-inositol, D-lactose, choline chloride (Bender et al., 1960, J. Appl. Physiol. 11520), amino acids (Phan The Tran and Bender, 1960, Exp. Cell Res. 20: 651), methanol, acetamide, glycerol monoacetate (Lovelock, 1954, Biochem. J. 56: 265), and inorganic salts (Phan The Tran and Bender, 1960, Proc. Soc. Exp. Biol. Med. 104: 388; Phan The Tran and Bender, 1961, in Radiobiology, Proceedings of the Third Australian Conference on Radiobiology, Ilbery, P. L. T., ed., Butterworth, London, p. 59).

A controlled slow cooling rate is desirable. Different cryoprotective agents (Rapatz et al., 1968, Cryobiology 5(1): 18-25) and different cell types have different optimal cooling rates (see, e.g., Rowe and Rinfret, 1962, Blood 20: 636; Rowe, 1966, Cryobiology 3(1): 12-18; Lewis et al., 1967, Transfusion 7(1):17-32; and Mazur, 1970, Science 168939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which can be containers with an extremely low vacuum and internal super insulation, such that heat leakage and nitrogen losses are kept to an absolute minimum.

Other methods of cryopreservation of viable cells, or modifications thereof, are available and envisioned for use (e.g., cold metal-mirror techniques; Livesey and Linner, 1987, Nature 327: 255; Linner et al., 1986, J. Histochem. Cytochem. 34(9): 1123-1135; see also U.S. Pat. No. 4,199, 022 by Senken et al., U.S. Pat. No. 3,753,357 by Schwartz, U.S. Pat. No. 4,559,298 by Fahy.

Frozen cells are preferably thawed quickly (e.g., in a water bath maintained at 37°-41° C.) and chilled immediately upon thawing.

It may be desirable to treat the immune cells in order to prevent cellular clumping upon thawing. To prevent clumping, various procedures can be used, including but not limited to the addition before and/or after freezing of Dnase (Spitzer et al., 1980, Cancer 45: 3075-3085), low molecular weight dextran and citrate, hydroxyethyl starch (Stiff et al., 1983, Cryobiology 20: 17-24), etc.

The cryoprotective agent, if toxic in humans, should be removed prior to therapeutic use of the thawed DC's.

One way in which to remove the cryoprotective agent is by dilution to an insignificant concentration.

According to some embodiments of the present invention there is provided a method of inhibiting growth of cells of a tumor (e.g., a primary and/or secondary tumor as described herein) or of controlling and/or treating cancer in a subject in need thereof, which comprises administering immune cells produced by a subject upon gNO local administration as described herein in any of the respective embodiments. In some embodiments, the immune cells are isolated from leukocytes extracted from the subject following the gNO local administration.

According to some embodiments there are provided immune cells as described herein, for use in inhibiting growth of cells of a tumor (e.g., a primary and/or secondary tumor as described herein) or in controlling and/or treating cancer in a subject in need thereof.

According to some embodiments there is provided a use of immune cells as described herein, in the manufacture of a medicament for inhibiting growth of cells of a tumor (e.g., a primary and/or secondary tumor as described herein) or for controlling and/or treating cancer in a subject in need thereof.

The subject to be treated by the immune cells can be the same subject from which the immune cells were isolated or another subject, which is preferably afflicted by the same tumor type.

According to some embodiments of the present invention there is provided a method for treating cancer in a subject by administering the immune cells as described herein, when produced by another subject exposed to gNO administration as described herein in any of the respective embodiments.

The immune cells as described herein can be for use in adoptive immunotherapy against cancer, as well as in methods for the use of the immune cells as vaccines and/or immunotherapeutics to slow or inhibit the growth of a primary or metastatic cancer. Adoptive immunotherapy, which involves the transfer of autologous immune cells, e.g., antigen-specific T-cells, generated ex vivo, is a strategy to treat cancer.

In some embodiments, the immune cells, in particular allogeneic immune cells obtained from a donor, are engineered (modified) to make them suitable for immunotherapy purposes, i.e., non-allogenic. By allogeneic it is meant that the cells are obtained from individuals belonging to the same species but are genetically dissimilar. In some embodiments, the immune cells can be engineered to be non-allogenic (non-alloreactive) by any suitable method known in the art.

In some embodiments, prior to administering the immune cells from one patient to treat cancer in another patient, the immune cells are modified to avoid or overcome an immune response to the infused cells by the receiving patient. In some embodiments, the immune cells are modified to knockout or reduce human leukocyte antigen (HLA), for example HLA-A, HLA-B, HLA-C, or HLA receptor expression. The modified immune cells derived from donors can evade an immune response and provide a foundation whereby cells from a single donor can be administered to multiple recipients. Such modified immune cells are also contemplated according to the present embodiments.

Ex Vivo gNO Treatment:

According to an aspect of some embodiments of the present invention there are provided methods and uses of gNO is which gNO is administered to tumor cells ex vivo. Such methods and uses can be for stimulating an immunological response to a tumor in a subject in need thereof. Such methods and uses can be ex vivo immunization or ex vivo vaccination of a subject against the tumor.

According to embodiments of this aspect of the embodiments of the present invention, there is provided a method of vaccination comprising exposure of tumor cells ex vivo to gNO and injecting the ex vivo treated cells, with or without an adjuvant, to a patient.

According to embodiments of this aspect of the embodiments of the present invention, there is provided a method for induction of a universal cancer-specific vaccination for a cancer patient. In some embodiments, one or more tumor samples are exposed to gaseous nitric oxide (gNO) as described herein in any of the respective embodiments and any combination thereof, and libraries of dead tumor cells are built and categorized according to the primary cancer type. The one or more tumor samples can be from the same patient. The one or more tumor samples can be from the two or more patients.

According to embodiments of this aspect of the embodiments of the present invention, there is provided a method of ex vivo immunization. The method can comprise collecting a tissue sample, or cells, from a patient's primary and/or secondary (e.g., metastases) tumor, as described herein, and suspending the sample or cells in a cell suspension. The patient's cells can be exposed to a cytotoxic dose of gNO. The dose can be between 100 ppm or 1,000 ppm to 1,000,000 ppm gNO (0.1%-100% gNO), preferably, 50,000 ppm (5%) gNO, although lower doses are also contemplated. The gNO can be delivered at from about 0.1 LPM to about 10 LPM, and between about 1 and about 30 or about 60 minutes.

The obtained dead tumor cells can be injected into a patient, either intratumorally, locally to the site of the tumor or systemically. A cell bank of dead tumor cells from multiple patients can be established which can be used to create a gNO-based cancer vaccine.

According to an aspect of some embodiments of the present invention there is provided a method of stimulating an immunological response to a tumor in a subject afflicted by the tumor, the method comprising exposing a tumor sample isolated from the subject, or a biomaterial extracted therefrom, to gaseous nitric oxide (gNO); subsequent to the exposing, contacting the tumor sample or a biomaterial extracted therefrom with antigen presenting immune cells, to thereby obtain immune cells presenting an autologous antigenic biomaterial; and administering the immune cells to the subject.

According to an aspect of some embodiments of the present invention there is provided a use of gNO for stimulating an immunological response to a tumor in a subject afflicted by the tumor, by exposing a tumor sample isolated from the subject, or a biomaterial extracted therefrom, to gaseous nitric oxide (gNO).

According to an aspect of some embodiments of the present invention there is provided a use of gNO for stimulating an immunological response to a tumor in a subject afflicted by the tumor, wherein the gNO is used to treat tumor cells ex vivo, and the gNO-treated tumor cells are then administered to the subject.

Such methods and uses are also referred to herein as ex vivo immunization or ex vivo vaccination of the subject by gNO.

The methods and uses as described in these embodiments can be for inhibiting growth and/or killing cells or tissue of a primary tumor in the subject, e.g., by stimulating an anti-tumor immunological response in the subject against its own tumor.

Alternatively or in addition, the methods as uses as described in these embodiments can be used for preventing and/or inhibiting growth of a secondary (recurrent and/or metastasizing) tumor in the subject, e.g., by stimulating an anti-tumor immunological response in the subject against its own tumor.

Alternatively, or in addition, the methods as uses as described in these embodiments can be used for vaccinating the subject against the tumor.

According to some of any of the embodiments described herein for these aspects, prior to exposing tumor cells or tissue to gNO ex vivo, a sample of the tumor, which can be a whole tumor or a portion thereof, is obtained. This can be done, for example, by surgery, biopsy, or any other method known in the art for tumor excision, resection, or sampling.

The tumor sample can then be processed, for example, for extracting therefrom biomaterial which can be a proteinacious biomaterial and/or genetic biomaterial. An exemplary processing procedure is described in the Examples section that follows. The extracted biomaterial can then be exposed to gNO, as described herein.

Alternatively, the tumor sample is exposed to gNO, and after the exposure, the treated tumor is processed for extracting therefrom the biomaterial.

Exposure to the gNO can be performed, for example, by placing the tumor sample or the biomaterial extracted therefrom in a closed container or hood, and introducing gNO to the closed container or hood, as also described hereinabove, or directly into or on the tumor, for example, by spraying or injecting, using any of the systems, devices, configurations and modes of administration as described herein in any of the respective embodiments and any combination thereof, when applied or adjusted for application ex vivo.

In exemplary embodiments, exposing to gaseous nitric oxide (gNO) is at a dose of from about 100 ppm to about 1,000,000 ppm for a time period of from about 1 second to about 60 minutes at a volumetric flow (flow volume) of from about 0.00001 LPM to about 1 LPM, including any intermediate values and subranges between any of the foregoing, and according to any of the embodiments described herein for local administration of gNO and any combination thereof.

The treated tumor cells or the biomaterial extracted therefrom can then be used for stimulating an immunological response, immunization and/or vaccination of the subject against the tumor.

According to some of any of the embodiments described herein, subsequent to the exposing, the gNO-treated tumor sample or the gNO-treated biomaterial extracted therefrom, or the biomaterial extracted from the gNO-treated tumor sample, which are collectively referred to herein as gNO-treated sample, are introduced to the subject.

The gNO-treated sample comprises an antigenic biomaterial which triggers an immunological response to the tumor.

In some of these embodiments, the gNO-treated sample is introduced per se. Preferably, the gNO-treated sample is introduced to the sample by means of antigen presenting immune cells, preferably autologous immune cells.

Autologous immune cells can be obtained from the subject, for example, from a blood organ of the subject (e.g., by drawing a blood sample from the subject, or from a sample of a lymphatic blood organ). The sample of the blood organ can be obtained by methods known in the art.

According to some of any of the embodiments described herein, the blood organ sample is processed to isolate therefrom immune cells (e.g., dendritic cells). This can be done by methods known in the art. An exemplary method is described in the Examples section that follows.

The immune cells are then contacted (e.g., incubated) with the gNO-treated sample, preferable with the extracted biomaterial, under suitable conditions to obtain antigen presenting immune cells containing the antigenic biomaterial obtained from the gNO-treated tumor. Such immune cells are presenting an autologous antigenic biomaterial.

The thus obtained immune cells are then and administered to the subject, using methods known in the art (e.g., as described herein with respect to immune cells).

An exemplary procedure for executing a method as described herein in provided in the Examples section that follows.

According to an aspect of some embodiments of the present invention there is provided a method of stimulating an immunological response to a tumor in a subject afflicted by the tumor, and corresponding uses thereof, which comprise:

exposing a tumor sample isolated from the subject, or a biomaterial extracted therefrom, to gaseous nitric oxide (gNO);

subsequent to the exposing, contacting the tumor sample or a biomaterial extracted therefrom with antigen presenting immune cells, to thereby obtain immune cells presenting an autologous antigenic biomaterial; and administering the immune cells to the subject.

According to an aspect of some embodiments of the present invention there is provided a method of stimulating an immunological response to a tumor in a subject afflicted by the tumor, and corresponding uses thereof, which comprise:

Obtaining a tumor sample from a subject;

Optionally processing the tumor sample to obtain an extracted biomaterial;

exposing the tumor sample or a biomaterial extracted therefrom (if obtained prior to the exposing), to gaseous nitric oxide (gNO), according to any of the respective embodiments described herein and any combination thereof;

optionally processing the gNO-treated tumor sample to obtain an extracted biomaterial (which can be done in cane the tumor sample was not processed prior to exposure to gNO);

obtaining a sample from a blood organ of the subject;

processing the blood organ sample to isolate therefrom immune cells (e.g., antigen-presenting immune cells)

Contacting the isolated immune cells with the gNO-treated tumor sample or the gNO-treated biomaterial extracted therefrom, to thereby obtain immune cells presenting an autologous antigenic biomaterial; and administering the immune cells to the subject.

In an alternative method, the gNO-treated sample is contacted with immune cells derived from another subject, and the immune cells can be allogeneic or non-allogeneic or modified, as described herein, to thereby provide antigen presenting immune cells that present allogeneic antigenic biomaterial. In some embodiments, the antigen presenting immune cells are engineered (modified) to make them suitable for immunotherapy purposes, namely, non-allogenic, as described hereinabove. The immune cells can be engineered to be non-allogenic (non-alloreactive) by any suitable method known in the art.

In exemplary embodiments, prior to administering the antigen presenting immune cells from one patient to another patient, the immune cells are modified to avoid or overcome an immune response to the administered cells by the receiving patient. In some embodiments, the antigen presenting immune cells are modified to knockout or reduce human leukocyte antigen (HLA), for example HLA-A, HLA-B, HLA-C, or HLA receptor expression. The modified antigen presenting immune cells derived from donors can evade an immune response and provide a foundation whereby cells from a single donor can be administered to multiple recipients. Such modified antigen presenting immune cells are also contemplated according to the present embodiments.

These immune cells can then be used as immune response stimulator, immunization, vaccination, or simple as medicament, when administered to a patient, which can be the patient from which the immune cells were derived, or any other patient, preferably upon being processed to prevent rejection, as described herein.

Thus, the gNO-treated sample, which contain an antigenic biomaterial as described herein, can be used per se as a vaccine or for stimulating an immune response to a tumor which is of the same type as the tumor from which it is derived prior to gNO treatment.

According to an aspect of some embodiments of the present invention there is provided an antigenic biomaterial extracted from tumor cells of a subject upon exposing the tumor cells or a biomaterial extracted therefrom to gaseous NO, as described herein in any of the respective embodiments.

According to another aspect of some embodiments of the present invention, there are provided antigen presenting immune cells comprising the antigenic biomaterial described herein. The immune cells can be as described herein in any of the respective embodiments.

According to another aspect of some embodiments of the present invention, there is provided a method of stimulating an anti-tumor immune response in a subject in need thereof, which comprises administering to the subject the antigen presenting immune cells containing the antigenic biomaterial as described herein.

According to another aspect of some embodiments of the present invention, there is provided a use of the antigen presenting immune cells containing the antigenic biomaterial as described herein for stimulating an anti-tumor immune response in a subject in need thereof.

According to some embodiments of these methods and uses, the antigenic biomaterial is extracted from tumor cells of the subject or from tumor cells of another subject afflicted by the same tumor type, and is exposed to gNO and optionally further processed as described herein in any of the respective embodiments.

According to embodiments of these methods and uses, the antigen presenting immune cells are obtained by incubating immune cells (e.g., antigen-presenting immune cells) with the antigenic biomaterial described herein. The immune cells can be derived from the subject to be treated or from another subject, including the subject from which the tumor sample was obtained.

Gas Treatment:

Any of methods, uses and systems as described herein can utilize a gas other than a gNO-containing gas. This includes, for example, air, oxygen, nitrogen, and any other gases.

According to an aspect of some embodiments of the present invention there is provided a method of inhibiting growth of cells of a tumor (primary and/or secondary), as described herein in any of the respective embodiments and any combination thereof, and/or of stimulating an immuno-logical response to the tumor, as described herein in any of the respective embodiments and any combination thereof, which employ local administration of a gas, as described herein, to the tumor. Corresponding uses of the gas are also provided.

According to embodiments of this aspect of the present invention, the gas is locally administered at high pressure, of from about 0.1 bar to about 10 bars, or from 1 bar to 10 bars, or from 1 bar to 5 bars, or from 1.1 bar to 5 bars, including any intermediate values and subranges therebetween.

According to some of any of the embodiments described herein, the gas is locally administered at a flow of from about 0.00001 LPM to about 10 LPM, including any intermediate values and subranges therebetween, and, for example, as described herein for gNO.

According to some of any of the embodiments described herein, the gas is locally administered at a pressure as described herein for a time period of at least 1 second, for example, from about 1 second to about 3 hours, or to about 1 hour, including any intermediate values and subranges therebetween, and, for example, as described herein for gNO.

The local administration can be continuous or pulsed, for example, as described herein for gNO.

According to some of any of the embodiments described herein, the gas is locally administered at a flow of from 0.00001 LPM to about 10 LPM and a pressure of from about 0.1 to about 10 bar, for a time period of at least 1 second.

According to some of any of the embodiments described herein, the volumetric flow (flow volume) ranges from about 0.0001 LPM to about 0.1 LPM.

According to some of any of the embodiments described herein, the gas is administered to a tumor having a volume of less than 20 cm³, or of from 0.1 to 10 cm³.

Further embodiments of the methods and uses as described for this aspect of the present invention can be the same as described herein for gNO local administration.

According to some embodiments, there is provided a method of inducing an immunological response for treating a tumor comprising locally administering a gas at a volumetric flow (flow volume) of about 0.01 LPM to 3 LPM, and at 3.5 bar (~50 psi) to a 0.1 to 10 cm³ tumor. According to some embodiments, there is provided a method of eradicat-ing distant metastases by treating a tumor or metastases comprising locally administering a gas at a volumetric flow (flow volume) of about 0.01 LPM to 3 LPM, at 3.5 bar (~50 psi) to a 0.1 to 10 cm³ tumor.

In some embodiments, gNO-free gas, when administered at 0.0001 Liter Per Minute (LPM)—LPM and 3.5 bar (~50 psi) to a 0.1-10 cm³ tumor, results in comprehensive cancer cell death, regardless the molecular composition of the gas.

According to some of any of the embodiments of this aspect, the gas is nitrogen gas. According to some of any of the embodiments of this aspect the gas is air.

Combination Therapy:

According to some of any of the embodiments described herein, in any of the methods and uses and systems as described herein, gNO local administration and/or ex vivo treatment can be used in combination with an additional therapy for treating the disease associated with the tumor (e.g., cancer).

According to some of any of the embodiments described herein, in any of the methods and uses and systems as described herein, gNO local administration and/or ex vivo treatment can be used in combination with an anti-cancer therapy.

Suitable anti-cancer therapy includes, for example, che-motherapy, radiotherapy, phototherapy and/or photody-namic therapy, surgery, nutritional therapy, ablative therapy, combined radiotherapy and chemotherapy, brachiotherapy, proton beam therapy, immunotherapy, cellular therapy and photon beam radiosurgical therapy, and any combination of the foregoing.

Chemotherapeutic drugs (e.g., anti-cancer drugs) that may optionally be co-administered to the subject prior to, con-comitant with and/or subsequent to gNO treatment as described herein in any of the respective embodiments include, but are not limited to acivicin, aclarubicin, acoda-zole, acronine, adozelesin, aldesleukin, altretamine, ambomycin, ametantrone, aminoglutethimide, amsacrine, anastrozole, anthramycin, asparaginase, asperlin, azaciti-dine, azetepa, azotomycin, batimastat, benzodepa, bicaluta-mide, bisantrene, bisnafide, bizelesin, bleomycin, brequinar, bropirimine, busulfan, cactinomycin, calusterone, carace-mide, carbetimer, carboplatin, carmustine, carubicin, carze-lesin, cedefingol, chlorambucil, cirolemycin, cisplatin, cladribine, crisnatol, cyclophosphamide, cytarabine, dacar-bazine, dactinomycin, daunorubicin, decitabine, dexorma-platin, dezaguanine, diaziquone, docetaxel, doxorubicin, droloxifene, dromostanolone, duazomycin, edatrexate, eflo-rnithine, elsamitrucin, enloplatin, enpromate, epipropidine, epirubicin, erbulozole, esorubicin, estramustine, etanida-zole, etoposide, etoprine, fadrozole, fazarabine, fenretinide, floxuridine, fludarabine, fluorouracil, flurocitabine, fosqui-done, fostriecin, gemcitabine, hydroxyurea, idarubicin, ifos-famide, ilmofosine, interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine, megestrol, melengestrol, melphalan, menogaril, mercap-topurine, methotrexate, metoprine, meturedepa, mitindo-mide, mitocarcin, mitocromin, mitogillin, mitomalcin, mito-mycin, mitosper, mitotane, mitoxantrone, mycophenolic acid, nocodazole, nogalamycin, ormaplatin, oxisuran, pacli-taxel, pegaspargase, peliomycin, pentamustine, peplomycin, perfosfamide, pipobroman, piposulfan, piroxantrone, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine, vindesine, vinepidine, vinglycinate, vinleurosine, vinorelbine, vinrosidine, vinzolidine, vorozole, zeniplatin, zinostatin, zorubicin, and any pharmaceutically acceptable salts thereof.

In some embodiments, the anti-cancer therapy comprises immunotherapy, including, for example, checkpoint inhibitors, CAR-T cell therapy, and/or vaccine adjuvants (e.g., interferon or saponin), and immune-adjuvants, such as aluminum salts, organic adjuvants, and genomic material-based adjuvants, such as CpG. Anti-tumor immunity can be further augmented by inhibition of immune suppressor cells.

According to some embodiments, the anti-cancer therapy comprises administration of an anti-cancer immune modulator agent.

As used herein, the term "anti-cancer immune modulator agent" refers to an agent capable of eliciting an immune response (e.g. T cell, NK cell) against a cancerous cell.

Exemplary such agents include a cancer antigen, a cancer vaccine, an anti-cancer antibody, a cytokine capable of inducing activation and/or proliferation of a T cell and an immune-check point regulator.

Alternatively or additionally, such modulators may be immune stimulators such as immune-check point regulators which are of specific value in the treatment of cancer.

As used herein the term "immune-check point regulator" refers to a molecule that modulates the activity of one or more immune-check point proteins in an agonistic or antagonistic manner resulting in activation of an immune cell.

As used herein the term "immune-check point protein" refers to a protein that regulates an immune cell activation or function. Immune check-point proteins can be either co-stimulatory proteins (i.e. transmitting a stimulatory signal resulting in activation of an immune cell) or inhibitory proteins (i.e. transmitting an inhibitory signal resulting in suppressing activity of an immune cell). According to some embodiments, the immune check-point protein regulates activation or function of a T cell. Numerous checkpoint proteins are known in the art and include, but not limited to, PD1, PDL-1, B7H2, B7H4, CTLA-4, CD80, CD86, LAG-3, TIM-3, KIR, IDO, CD19, OX40, 4-1BB (CD137), CD27, CD70, CD40, GITR, CD28 and ICOS (CD278).

According to some embodiments, the anti-cancer therapy comprises a surgical procedure, for example, resection or excision of at least a portion of the tumor. The tumor can be exposed to gNO local administration as described herein before, during and/or after tumor excision. To better control cancer cells spreading during surgery, a perforated scalpel connected directly to a gNO tank or cylinder can be used serving for the delivery of gNO while the tumor is being removed, as shown, for example, in FIGS. 35A-C. Purging the gNO delivery system, for example, with nitrogen, before and/or after is preferred. Purging can also be performed intermittently during the procedure.

Additional Embodiments

According to an aspect of some of embodiments of the present invention there is provided a method of treating a tumor comprising contacting the tumor with a constant dose of from about 1,000 ppm to about 1,000,000 ppm of gaseous nitric oxide (gNO) for a time period of from about 1 second to about 60 minutes daily at a flow volume of from about 0.00001 LPM to about 1 LPM.

According to some of any of the embodiments described herein, contacting is by locally administering the gNO to tumor cells or tissues in a subject in need thereof.

According to some of any of the embodiments described herein, the gNO is administered at a dose of from about 1,000 ppm to about 100,000 ppm, including any intermediate values and subranges therebetween.

According to some of any of the embodiments described herein, the gNO is administered at a dose of from about 10,000 ppm to about 50,000 ppm, including any intermediate values and subranges therebetween.

According to some of any of the embodiments described herein, the gNO is administered for a time period that ranges from about 30 seconds to about 10 minutes, including any intermediate values and subranges therebetween.

According to some of any of the embodiments described herein, the gNO is administered at a volumetric flow (flow volume) of from about 0.001 LPM to about 0.5 LPM, including any intermediate values and subranges therebetween.

According to some of any of the embodiments described herein, the gNO is administered at two or more administration sites in the tumor.

According to some of any of the embodiments described herein, the distance between the two or more administration sites is, independently, from about 2.5 mm to about 1 cm, including any intermediate values and subranges therebetween.

According to some of any of the embodiments described herein, the distance between the two or more administration sites is, independently, from about 0.25 cm to about 0.5 cm.

According to some of any of the embodiments described herein, the total amount of gNO administered is from about 0.05 mg to about 500 mg, or from about 50 mg to about 500 mg, per $cm^3$ tumor, including any intermediate values and subranges therebetween.

According to some of any of the embodiments described herein, the total amount of gNO injected per tumor is about 250 mg per $cm^3$ tumor, or from about 0.1 to about 1 mg per a tumor of 20 $mm^3$ or less.

According to some of any of the embodiments described herein, the method further comprises scavenging excess gNO from the one or more administration sites.

According to some of any of the embodiments described herein, gNO is pulsed from about 2 to about 20 times.

According to some of any of the embodiments described herein, each pulse is between about 4000 ppm and about 1,000,000 ppm gNO at a flow volume of from about 0.0001 LPM to about 0.5 LPM, wherein each pulse is, independently, between about 0.1 second and about 10 minutes per pulse with a break of from about 0.1 second to about 10 minutes between pulses.

According to some of any of the embodiments described herein, the method comprises from about 5 to about 15 pulses of gNO, including any intermediate values and subranges therebetween.

According to some of any of the embodiments described herein, the method comprises about 10 pulses of gNO.

According to some of any of the embodiments described herein, each pulse of gNO is, independently, from about 10 seconds per pulse to about 45 seconds per pulse, including any intermediate values and subranges therebetween.

According to some of any of the embodiments described herein, each pulse of gNO is about seconds per pulse.

According to some of any of the embodiments described herein, gNO is not administered between each pulse and the time is, independently, between about 1 second to about 300 seconds.

According to some of any of the embodiments described herein, the time between each pulse is about 20 seconds.

According to some of any of the embodiments described herein, the gNO is administered at a dose of from about 4,000 ppm to about 500,000 ppm, including any intermediate values and subranges therebetween.

According to some of any of the embodiments described herein, the gNO is administered at a dose of from about 50,000 ppm to about 250,000 ppm, including any intermediate values and subranges therebetween.

According to some of any of the embodiments described herein, the gNO is administered at a dose of about 100,000 ppm.

According to some of any of the embodiments described herein, the method further comprises co-administering a further agent selected from the group consisting of anticancer drugs, anticancer treatments, chemotherapeutic agent, an immune-oncological agent, immunoadjuvant, and radiation.

According to some of any of the embodiments described herein, the gNO is administered to the subject (e.g., a human patient).

According to some of any of the embodiments described herein, gNO is administered with one or more needles such as a needle selected from the group consisting of a spray needle, an umbrella needle, a perforated needle, and an array of needles.

According to some of any of the embodiments described herein, gNO is administered to a box containing the tumor connected to a NOx filtering pump.

According to some of any of the embodiments described herein, gNO is administered in a gNO cap.

According to some of any of the embodiments described herein, the method further comprises scavenging or vacuuming gNO from an administration site.

According to some of any of the embodiments described herein, gNO is delivered to an intra-tumoral channel and the gNO scavenging is from a second intra-tumoral channel.

According to some of any of the embodiments described herein, gNO is sprayed in or on the tumor.

According to some of any of the embodiments described herein, gNO is sprayed before, during or after surgery.

According to some of any of the embodiments described herein, gNO is sprayed with a NO-delivering scalpel.

According to some of any of the embodiments described herein, gNO is vacuumed in a continuous or pulsed manner.

According to some of any of the embodiments described herein, gNO is administered for 0.1 second –10 minutes followed by a suction for 0.1 second –10 minutes.

According to some of any of the embodiments described herein, the gNO is administered no more than 1 cm from the tumor surface, for example from about 2.5 mm to about 1 cm or from about 0.25 cm to about 0.5 cm from the tumor surface.

According to some of any of the embodiments described herein, the method is repeated one or more times, and wherein the method is repeated more than one time, there can be, for example, one month between treatments.

According to some of any of the embodiments described herein, the gNO is delivered to a delivery device as described herein from a tank of gNO or other positive-pressure source.

According to some of any of the embodiments described herein, the method further comprises purging a gNO delivery system with nitrogen, for example, at 0.5-1 LPM, before and/or after treatment.

According to an aspect of some of embodiments of the present invention there is provided a method of inducing an immunological response to a tumor in a subject in need thereof (e.g., a subject afflicted with the tumor), the method comprising locally administering to the tumor tissue a dose of from about 1,000 ppm to about 1,000,000 ppm gaseous nitric oxide (gNO), preferably from about 10,000 ppm to about 500,000 ppm of gNO, for a time period that ranges from about 1 second to about 60 minutes daily at a flow volume of from about 0.0001 LPM to about 10 LPM.

According to an aspect of some of embodiments of the present invention there is provided a method of eradicating distant tumor metastases in a subject in need thereof, the method comprising locally administering to the tumor tissue a dose of about 1,000 ppm to about 1,000,000 ppm of gaseous nitric oxide (gNO) preferably about 10,000 ppm to about 500,000 ppm of gNO, for about 1 second to about 60 minutes daily at a flow volume of about 0.0001 LPM to 10 LPM.

According to some of any of the embodiments described herein, the gNO is administered at a dose of from about 10,000 ppm to about 100,000 ppm, including any intermediate values and subranges therebetween.

According to some of any of the embodiments described herein, the gNO is administered at a dose of from about 10,000 ppm to about 50,000 ppm, including any intermediate values and subranges therebetween.

According to some of any of the embodiments described herein, the gNO is administered for a time period of from about 1 second to about 10 minutes, including any intermediate values and subranges therebetween.

According to some of any of the embodiments described herein, the gNO is administered at a flow volume of from about 0.001 LPM to about 1 LPM, including any intermediate values and subranges therebetween.

According to some of any of the embodiments described herein, the gNO is administered at two or more administration sites in the tumor.

According to some of any of the embodiments described herein, the distance between the two or more administration sites is, independently, from about 2.5 mm to about 1 cm, including any intermediate values and subranges therebetween.

According to some of any of the embodiments described herein, the distance between the two or more administration sites is, independently, from about 0.25 cm to about 0.5 cm.

According to some of any of the embodiments described herein, the total amount of gNO administered is from about 0.05 mg to about 500 mg, or from about 50 to about 500 mg, per $cm^3$ tumor, including any intermediate values and subranges therebetween.

According to some of any of the embodiments described herein, the total amount of gNO administered is about 250 mg per $cm^3$ tumor, or from about 0.1 to about 10 mg per a tumor of 20 $mm^3$ or less.

According to some of any of the embodiments described herein, gNO is administered at a constant dose.

According to some of any of the embodiments described herein, gNO is pulsed from about 2 to about 20 times.

According to some of any of the embodiments described herein, each pulse is between about 10,000 ppm and about 500,000 ppm gNO at a flow volume of from about 0.0001 LPM to about 0.5 LPM, wherein each pulse is, independently, between about 1 second and about 10 minutes per pulse with a break of from about 0.1 second to about 10 minutes between pulses.

According to some of any of the embodiments described herein, the method comprises from about 5 to about 15 pulses of gNO.

According to some of any of the embodiments described herein, the method comprises about 10 pulses of gNO.

According to some of any of the embodiments described herein, each pulse of gNO is, independently, from about 10 seconds per pulse to about 45 seconds per pulse.

According to some of any of the embodiments described herein, each pulse of gNO is about seconds per pulse.

According to some of any of the embodiments described herein, the time between each pulse is about 20 seconds.

According to some of any of the embodiments described herein, the gNO is administered at a dose of from about 15,000 ppm to about 500,000 ppm, including any intermediate values and subranges therebetween.

According to some of any of the embodiments described herein, the gNO is administered at a dose of from about 50,000 ppm to about 250,000 ppm, including any intermediate values and subranges therebetween.

According to some of any of the embodiments described herein, the gNO is administered at a dose of about 100,000 ppm.

According to some of any of the embodiments described herein, the method further comprises co-administering a further agent selected from the group consisting of anticancer drugs, anticancer treatments, chemotherapeutic agent, an immune-oncological agent, and immune-adjuvant and radiation.

According to some of any of the embodiments described herein, the gas is administered to a human subject.

According to some of any of the embodiments described herein, the gas is administered with one or more needles such as a needle selected from the group consisting of a spray needle, an umbrella needle, a perforated needle, and an array of needles.

According to some of any of the embodiments described herein, gNO is administered to a box containing the tumor connected to a NOx filtering pump.

According to some of any of the embodiments described herein, gNO is administered in a gNO cap.

According to an aspect of some of embodiments of the present invention there is provided a method of inducing anti-tumor immune cells in a subject in need thereof, the method comprising:

locally administering to cancer cells in the subject from about 10,000 ppm to about 1,000,000 ppm gaseous nitric oxide (gNO), for a time period of from about 1 second to about 60 minutes;

extracting and collecting leukocytes from the blood lymphatic organs (i.e. draining lymph nodes) of the subject, or from the treated tumor, from about 7 to about 21 days post treatment; and administering the leukocytes to the subject.

According to some of any of the embodiments described herein for this aspect, the method further comprises, prior to administering the leukocytes to the subject, proliferating and purifying the leukocytes outside the subject's body (ex-vivo) to about 1 to about 5 billion cells or more.

According to some of any of the embodiments described herein for this aspect, the method further comprises cryopreservation of leukocytes. According to an aspect of some of embodiments of the present invention there is provided a method of inducing subject-specific and cancer-specific immune cells, the method comprising:

locally administering to cancer cells in the subject from about 10,000 ppm to about 1,000,000 ppm gaseous nitric oxide (gNO), for a time period of from about 1 second to about 60 minutes;

extracting and collecting leukocytes from the blood lymphatic organs (i.e. draining lymph nodes), or the treated tumor, of the subject, from about 7 to about 21 days post treatment; and administering the leukocytes to the subject.

According to some of any of the embodiments described herein for this aspect, the method further comprises, prior to administering the leukocytes to the subject, proliferating and purifying the leukocytes outside the subject's body (ex-vivo) to about 1 to about 5 billion cells or more.

According to some of any of the embodiments described herein for this aspect, the method further comprises cryopreservation of leukocytes. According to some of any of the embodiments described herein, the method comprises locally administering from about 200,000 ppm to about 500,000 ppm of gNO, including any intermediate values and subranges therebetween.

According to some of any of the embodiments described herein, from about 1 to about 100 million leukocytes are collected.

According to some of any of the embodiments described herein, the method is for treating the tumor or metastases thereof in the subject.

According to some of any of the embodiments described herein, the leukocytes are administered to the subject every time there is a metastatic event.

According to some of any of the embodiments described herein, administering the leukocytes is by injecting (e.g., intravenously or intratumorally) the leukocytes into the subject's body.

According to some of any of the embodiments described herein, the method is for vaccinating the subject against the cancer.

According to some of any of the embodiments described herein, administering the leukocytes is by injecting (e.g., intravenously or intratumorally) the leukocytes into the subject.

According to some of any of the embodiments described herein, the method is for inducing a patient-specific anti-tumor immunity in the subject.

According to some of any of the embodiments described herein, administering the leukocytes is by injecting (e.g., intravenously or intratumorally) the leukocytes into the subject.

According to some of any of the embodiments described herein, the method further comprises co-administering a further agent selected from the group consisting of anticancer drugs, anticancer treatments, chemotherapeutic agent, an immune-oncological agent, immune-adjuvant and radiation.

According to an aspect of some of embodiments of the present invention there is provided a method of treating a tumor with gNO while minimizing damage to adjacent normal cells and/or tissue, the method comprising intratumoral administration of from about 1,000 ppm to about 1,000,000 ppm of gaseous nitric oxide (gNO) for a time period of from about 1 second to about 60 minutes daily at a flow volume of from about 0.0001 LPM to about 1 LPM; wherein the total dose of gNO administered to the tumor is from about 0.01 to about 300 mg, or from about 0.01 to about 200 mg, or from about 0.3 mg to about 300 mg, including any intermediate values and subranges therebetween.

According to some of any of the embodiments described herein, the gNO is administered at a dose of from about 10,000 ppm to about 500,000 ppm, including any intermediate values and subranges therebetween.

According to some of any of the embodiments described herein, the gNO is administered at a dose of from about 25,000 ppm to about 250,000 ppm, including any intermediate values and subranges therebetween.

According to some of any of the embodiments described herein, the gNO is administered for a time period of from about 30 seconds to about 10 minutes, including any intermediate values and subranges therebetween.

According to some of any of the embodiments described herein, the gNO is administered at a flow volume of from about 0.001 LPM to about 0.5 LPM, including any intermediate values and subranges therebetween.

According to some of any of the embodiments described herein, the gNO is administered at two or more administration sites in the tumor.

According to some of any of the embodiments described herein, the distance between the two or more administration sites is, independently, from about 2.5 mm to about 1 cm.

According to some of any of the embodiments described herein, the distance between the two or more administration sites is, independently, from about 0.25 cm to about 0.5 cm.

According to some of any of the embodiments described herein, the total amount of gNO administered is from about 0.1 mg to 100 mg.

According to an aspect of some embodiments of the present invention there are provided immune cells induced by a method as described herein.

According to some of any of the embodiments described herein, the immune cells are modified to be non-alloreactive.

According to some of any of the embodiments described herein, the immune cells are modified to knockout or reduce human leukocyte antigen (HLA), for example HLA-A, HLA-B, HLA-C, or HLA receptor expression.

According to an aspect of some of embodiments of the present invention there is provided a method for preserving the immune cells described herein.

According to some of any of the embodiments described herein, the immune cells are preserved through cryopreservation.

According to an aspect of some of embodiments of the present invention there is provided a method of vaccinating a patient against his/hers own tumor via locally administering a constant dose of from about 1,000 ppm to about 1,000,000 ppm of gaseous nitric oxide (gNO) for a time period of from about 1 second to about 60 minutes daily at a flow volume of from about 0.0001 LPM to about 1 LPM.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

As used herein throughout, "a" or "an" may mean one or more than one of an item.

As used herein throughout, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like, for medical and/or laboratory research purposes. Preferably, the subject is a human patient. More preferably, the subject is a human patient that has cancer.

The term throughout "about" as used herein when referring to a measurable value such as an amount of weight, time, dose, etc. is meant to encompass variations of +/−20% or +/−10% from the specified amount, as such variations are appropriate to perform the disclosed method. In embodiments, the term "about" is meant to encompass variations of +/−5%. In embodiments, the term "about" is meant to encompass variations of +/−1%. In embodiments, the term "about" is meant to encompass variations of +/−0.1%.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. As used herein, "treating" or "treatment" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient. In embodiments, "treat" or "treating" means accomplishing one or more of the following: (a) reducing tumor size; (b) reducing tumor growth; (c) reducing or limiting development and/or spreading of metastases.

The phrase "a method of treating" or its equivalent, when applied to, for example, cancer, refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented in that individual. For example, "preventing" includes inhibiting the growth, spread, and development of cancerous cell phenotypes and growths. Methods and devices disclosed herein also may be useful for eradicating cancerous cell phenotypes and growths in animal, and preferably mammal, and more preferably human, bodies. As used herein, "eradicating" includes treating, controlling, suppressing, hindering, blocking, killing, and slowing the spread or development of cancerous cell phenotypes and growths.

As used herein, a "therapeutically effective amount" is the amount of a composition sufficient to provide a beneficial effect to the individual to whom the composition is administered.

As used herein, the term "subject" includes mammals, preferably human beings at any age which suffer from the pathology. Preferably, this term encompasses individuals who are at risk to develop the pathology.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Study Drug: NO is a colorless, nonflammable, oxidizing gas. gNO was administered from 3.5-L cylinders, prepared, and supplied by Gordon Gas and Chemical (Tel Aviv, Israel) or 1 liter cylinders supplied by Impactor (Gan Yavne, Israel). As NO is a free radical that reacts within seconds, the inert gas nitrogen served as its stabilizing gas. NO concentrations used for this study were 0.015%-20% (150 to 200,000 ppm) NO in nitrogen. Air or nitrogen supplied from 3.5-liter cylinders served as the control gases.

All in vitro and ex vivo procedures were performed in a chemical hood in a well-ventilated room. Appropriate personal protection was used at all times. During gas exposure, the cylinder was placed inside a stabilizing apparatus. The gas was delivered via a pressure regulator through a designated silicone hose (International Biomedical, USA). The flow rate was set to 0.25-0.9 liters per minute (LPM) using a manual flow meter or to 0.002-0.05 LPM using a digital, remote-controlled mass flow controller (MFC, Bronkhorst).

Tumor cell lines: The mouse colon carcinoma cell line, CT26WT, was cloned from CT26, an N-nitroso-N-methyl-urethane-induced, undifferentiated colon carcinoma cell line. The mouse mammary tumor cell line, 4T1, is a 6-thioguanine resistant cell line. When injected into BALB/c mice, 4T1 spontaneously produces highly metastatic tumors that can metastasize to the lung, liver, lymph nodes and brain while the primary tumor is growing in situ. The primary tumor does not have to be removed to induce metastatic growth. Pane 02.03 is a pancreatic adenocarcinoma epithelial cell line derived in 1995 from a primary tumor removed from the head-of-the-pancreas of a female with pancreatic adenocarcinoma. CT26, 4T1 and Panc 02.03 cell lines were grown in RPMI based media (ATCC 30-2001) supplemented with fetal bovine serum and pen-strep (both from Biological Industries). The LLC1/LL/2 cell line was grown in DMEM based media (ATCC 30-2002) supplemented with fetal bovine serum and pen-strep (Biological industries). The B16.F10 cell lines was grown in DMEM based media (ATCC 30-2002) supplemented with fetal bovine serum and pen-strep (Biological industries).

Preparation of tumor cells: Tumor cell suspensions in Hanks' Balanced Salt Solution (HBSS) (Biological Industries, Israel) or RPMI or DMEM based cell culture media, at appropriate concentration of $1-2\times10^5$ cells/ml for in vitro studies or $2.5\times10^6-10.0\times10^6$ cells/ml for in vivo studies were freshly prepared. Cells were grown to 70% confluency and were harvested using trypsin (Biological Industries, Israel), and counted using a hemocytometer.

In vitro systems: One system involves a direct exposure of cancer cells to gNO in 96-well plate. Gaseous NO at 150 ppm-50,000 ppm was delivered at 0.3 LPM for 10 seconds—3 minutes. In another system, cancer cells were exposed to gNO in a box made of acrylic glass. Gaseous NO at 10,000-50,000 ppm was delivered at 0.9 LPM for 10 seconds—15 minutes.

The exposure of the cancer cells to gNO was done after removing the cell culture medium. Immediately after gas exposure, cell culture medium was added, and the cells were incubated at a 37° C. and 5% $CO_2$ incubator over-night. To test cell viability, XTT assay and Annexin V—Propidium Iodide assays were performed, according to known protocols.

Mice: All in vivo experimental procedures were carried out in accordance with the protocol approved by the Ethics Committee on the Use and Care of Animals. Institutional Animal Care and Use Committee (IACUC): 67-09-2019 and IL-20-3-149. The in vivo assays were performed on Balb/c or C57BL/6J mice: 7-10 weeks of age, obtained from Envigo (Ness-Ziona, Israel), unless otherwise indicated.

Inoculation of tumor cells: Cancer cell suspensions at a concentration of $2.5$-$10.0 \times 10^6$ cells/ml were inoculated to the right flank of mice at a dose volume of 0.1 ml. Administration was performed as soon as possible following cell suspension preparation and after manual shaking prior to inoculation. The cell suspension was then aspirated into a 1-ml syringe with a 27 G needle for subcutaneous (s.c.) injection.

Test article treatment: Mice were first anesthetized by an intraperitoneal (i.p) injection of 100 mg/kg ketamine and 20 mg/kg xylazine hydrochloride solution. After 10 minutes, tumor-bearing mice were treated with the indicated dose of gNO.

In all protocols, the gas was delivered from NO in $N_2$ cylinders. The outlet pressure was set to 2-3.5 bar using a pressure regulator that was connected directly to the cylinder.

In protocols that involve administration by needle injection, a silicone hose was connected directly to the pressure regulator on one end and to a manual or digital MFC on the other end. The flow was adjusted to 0.05 LPM-0.25 LPM. An additional silicone hose was connected to the flow controller as well as to a 23 G hypodermic needle. The needle was inserted horizontally into the center of each tumor.

Tumor volume calculation: Local tumor growth was determined by measuring 3 mutually orthogonal tumor dimensions 2-3 times per week, according to the following formula:

$$\text{Tumor volume} = \frac{\pi}{6} \times [\text{Diameter 1} \times \text{Diameter 2} \times \text{Diameter 3}] \text{ or}$$

$$\text{Tumor volume} = \text{Diamter 1} \times \text{Diameter } 2^2/2,$$

unless otherwise indicated. Diameter 1 represents length, Diameter 2 represents width and Diameter 3 represents height.

Challenge tumor inoculation: Up to 21 days after gas treatment was applied to the primary tumor, the appropriate cancer cell suspensions were prepared as described herein and inoculation of cells was repeated on the contralateral flank of the mice. Administration was performed as soon as possible following cell suspension preparation and after manual shaking prior to withdrawal of the cell suspension.

The percentage of challenge tumor take was monitored 2-3 times a week by taking a look at the inoculated site and touching this area to look for small tumors that are not yet visible. Naïve mice inoculated with tumor cells for the first time served as an internal control.

Winn assay: The Winn assay was performed by the s.c. injection of CT26 tumor cells 500,000 cells/mouse) mixed with either immune splenocytes (1,000,000 or 5,000,000 cells/mouse) or HBSS as a control.

Mixing of cells was performed immediately before injection to minimize leukocyte interactions within the syringe. Mice were observed 2-3 times a week and tumor development was determined by caliper measurements of tumor dimensions as described herein. Splenocytes were extracted from a CT26 tumor-bearing mouse, which was previously treated with 25,000 ppm NO for two 15-minute courses. This mouse was re-inoculated with CT26 cancer cells 12 days post treatment. Forty-four days after challenge assay conduction, no signs of tumor development were detected and this mouse was sacrificed and its splenocytes were extracted. The splenocytes were mixed with CT26 cells at a ratio of 1:2-1:10 (500,000 CT26 cells and 1,000,000 to 5,000,000 splenocytes, respectively). The cell mixtures were inoculated s.c. to the right flank of naïve Balb/c mice. Tumor take of visible outgrowths was monitored 2 to 3 times per week by taking a look at the inoculated site and touching this area to look for small tumors that are not yet visible. Naïve mice inoculated s.c. with 500,000 CT26 served as the control group.

Example 1

The effect of continuous gaseous nitric oxide (gNO) at 50,000 ppm compared to air (control) on the survival of CT-26 cancer cell line was tested.

CT-26 cells were prepared in RPMI medium and suspended in 96-well plates. The wells were exposed to the gas by a tubing that was directed at each well for 10, 60 or 180 seconds. The diameter of the gas tubing used was about 25% of the diameter of each well. Three wells were used for each gas and exposure time. The plates were thereafter placed in a 5% $CO_2$, 37° C. incubator for 24 hours and the viability of the cells was tested by XTT assay.

The obtained data is presented in FIG. 1 and shows about 1% viability of CT-26 cells after exposure to 50,000 ppm gNO for 10, 60, or 180 seconds, whereas more than 80% of the air-exposed CT-26 cells survived.

Example 2

The effect of continuous gaseous nitric oxide (gNO) at 150 ppm, 4,000 ppm, 10,000 ppm, or 50,000 ppm, compared to air (control), on the survival of 4T1 cancer cell line was tested.

4T1 cells were prepared in RPMI medium and suspended in six 96-well plates. The wells were exposed to the gas by a tubing that was directed at each well for 10, 60 or 180 seconds. The diameter of the gas tubing was about 25% of the diameter of each well. Three wells were used for each gas and exposure time. The plates were thereafter placed in a 5% $CO_2$, 37° C. incubator for 24 hours and the viability of the cells was tested by XTT assay.

Figure 2:
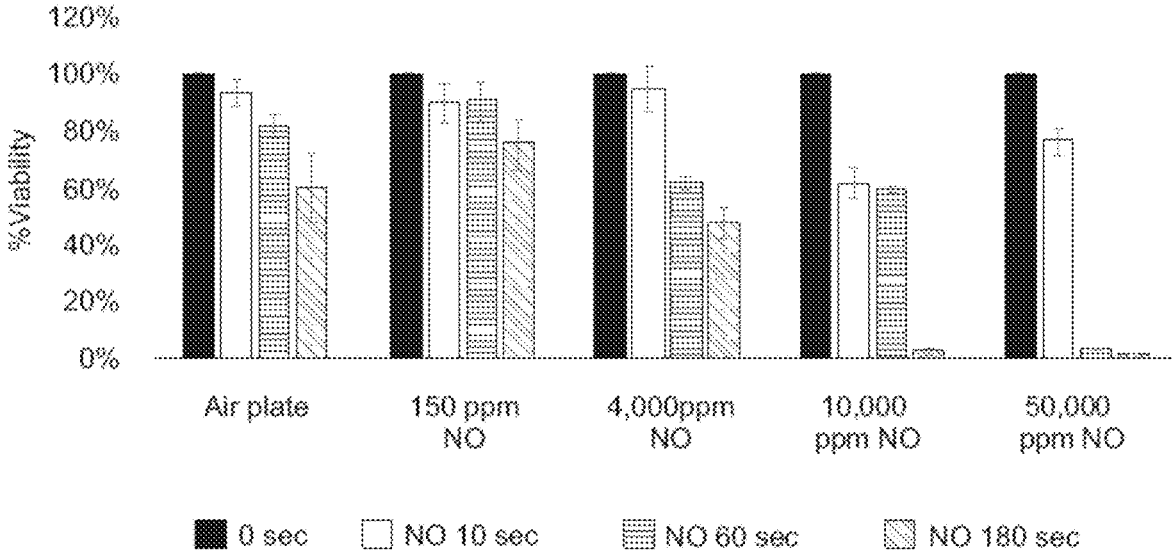
FIG. 2 is a bar graph showing the effect of 150-50,000 ppm NO or air on 4T1 cells in-vitro.

The obtained data is presented in FIG. 2 and show about 1-3% viability of 4T1 cells after exposure to 10,000 or 50,000 ppm gNO for 180 seconds, whereas more than 60% of the air-exposed 4T1 cells survived. In addition, less than 80% of 4T1 cells remained viable after 10 seconds when exposed to 10,000 ppm or 50,000 ppm gNO compared to more than 90% viability among air-exposed 4T1 cells. About 60% of 4T1 cells remain viable after 1 minute of exposure to 4,000-10,000 ppm gNO compared to more than 80% viability among air-exposed 4T1 cells.

Example 3

The effect of continuous gaseous nitric oxide (gNO) treatment at 4,000 ppm, 10,000 ppm, or 50,000 ppm compared to air (control) on the survival of A549 cancer cell line was tested.

A549 cells were prepared in RPMI medium and suspended in four 96-well plates. The wells were exposed to the gas by a tubing that was directed at each well for 10, 60 or 180 seconds. The diameter of the gas tubing used was about 25% of the diameter of each well. Three wells were used for each gas and exposure time. The plates were placed in a 5% $CO_2$, 37° C. incubator for 15-18 hours and the viability of the cells was tested by XTT assay.

Figure 3:
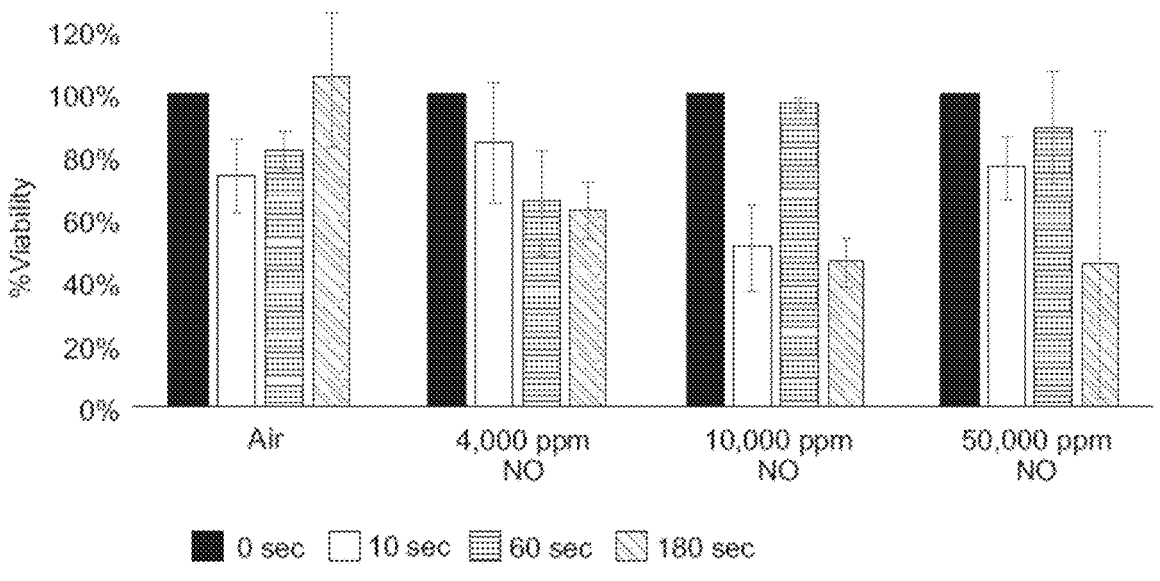
FIG. 3 is a bar graph showing the effect of 4,000-50,000 ppm NO or air on A549 cells in-vitro.

The obtained data is presented in FIG. 3 and shows about 45%-62% viability of A549 cells after exposure to 4000, 10,000, or 50,000 ppm gNO for 180 seconds, whereas about 100% of the air-exposed A549 cells survived. Results showed about 65%-96% viability of A549 cells after exposure to 4000, 10,000, or 50,000 ppm gNO for 60 seconds, whereas about 81% of the air-exposed A549 cells survived. Results showed about 50%-84% viability of A549 cells after exposure to 4000, 10,000, or 50,000 ppm gNO for 10 seconds, whereas about 73% of the air-exposed A549 cells survived.

Example 4

The effect of continuous gaseous nitric oxide (gNO) at 4,000 ppm, 10,000 ppm, or 50,000 ppm compared to air (control) on the survival of PC-3 cancer cell line was tested.

PC-3 cells were prepared in RPMI medium and suspended in four 96-well plates. The wells were exposed to the gas by a tubing that was directed at each well for 10, 60 or 180 seconds. The diameter of the gas tubing used was about 25% of the diameter of each well. Three wells were used for each gas and exposure time. The plates were placed in a 5% $CO_2$, 37° C. incubator for 15-18 hours and the viability of the cells was tested by XTT assay.

Figure 4:
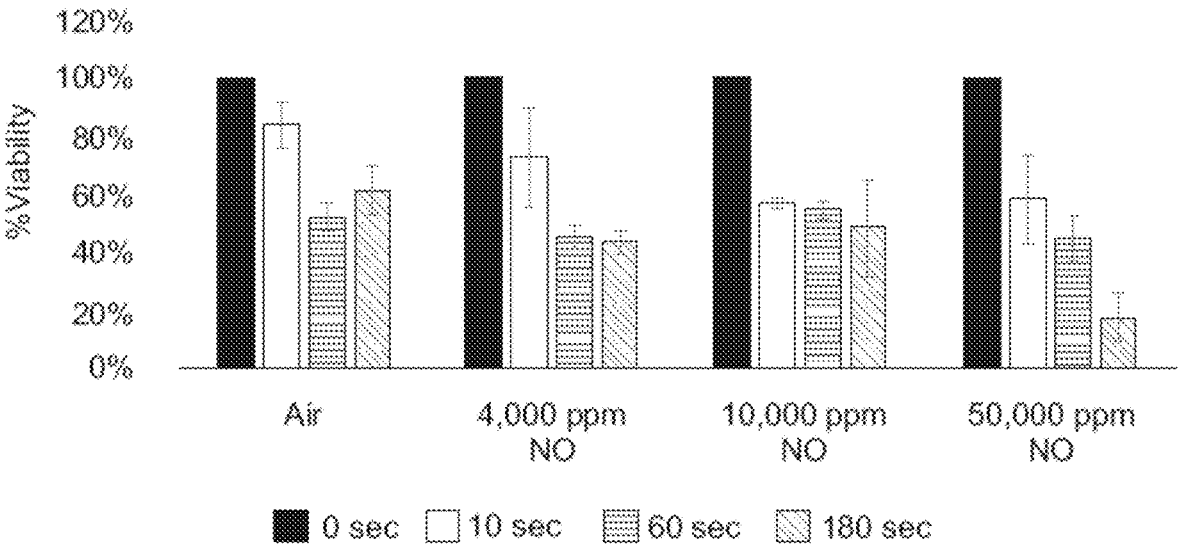
FIG. 4 is a bar graph showing the effect of 4,000-50,000 ppm NO or air on PC-3 cells in-vitro.

The obtained data is presented in FIG. 4 and shows about 17% viability of PC-3 cells after exposure to 50,000 ppm gNO for 180 seconds and 43-48% viability after exposure to 4,000 ppm and 10,000 ppm gNO for 180 seconds. The viability of air-exposed PC-3 cells was 61% after 180 seconds. In addition, 56%-72% viability of PC-3 was observed after 10 seconds of exposure to 4,000 ppm, 10,000 ppm and 50,000 ppm gNO whereas 84% of air treated PC-3 cells survived after 10 seconds. After 1 minute of exposure to 4,000 ppm, 10,000 ppm and 50,000 ppm gNO the viability of PC-3 cells was 44%-55% compared to 52% viability of air-treated PC-3 cells.

Example 5

The effect of continuous gaseous nitric oxide (gNO) at 10,000 ppm, 15,000 ppm, 20,000 ppm, 25,000 ppm, compared to air (control), on the survival of B16.F10 cancer cell line was tested.

B16.F10 cells were prepared in DMEM medium and suspended in 96-well plates. The plates were placed inside an approx. 2 liter exposure chamber. The plates were exposed to the gas by filling the chamber with gNO for 10 seconds, or 1, 3, 9 or 15 minutes. After exposure, the plates were placed in a 5% $CO_2$, 37° C. incubator for an overnight incubation and the viability of the cells was tested by XTT assay.

Figure 5:
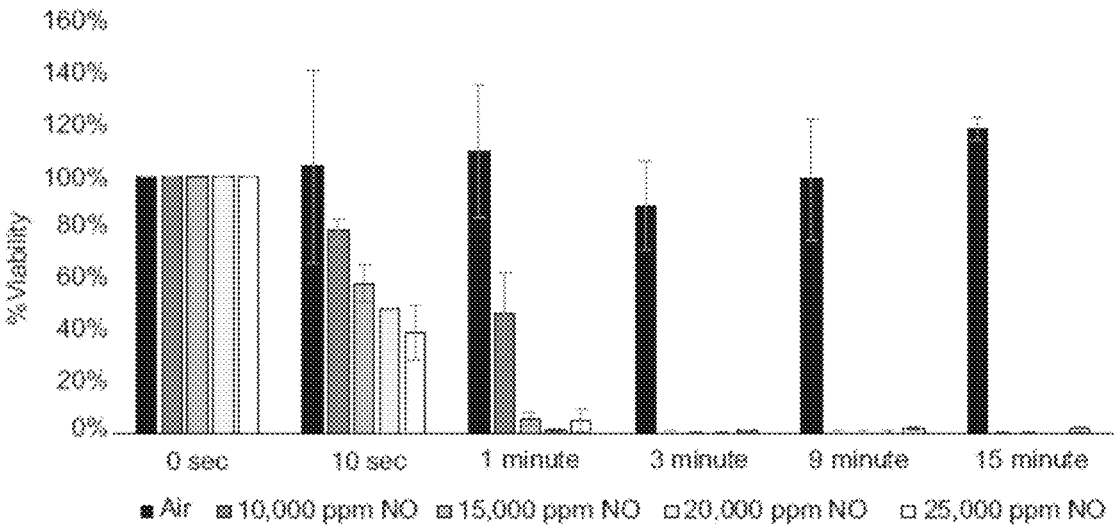
FIG. 5 is a bar graph showing the effect of 10,000-25,000 ppm NO or air on B16.F10 cells in-vitro.

The obtained data is presented in FIG. 5, and shows less than 5% viability of B16.F10 cells after exposure to 10,000 ppm-25,000 ppm gNO for 3-15 minutes.

Example 6

The effect of continuous gaseous nitric oxide (gNO) at 10,000 ppm, 15,000 ppm, 20,000 ppm, or 25,000 ppm, compared to air (control), on the survival of Panc02.03 cancer cell line was tested.

Panc02.03 cells were prepared in RPMI medium and suspended in 96-well plates. The plates were placed inside an approx. 2 liter exposure chamber. The plates were exposed to the gas by filling the chamber with gNO for 10 seconds, or 1, 3, 9 or 15 minutes. After exposure, the plates were placed in a 5% $CO_2$, 37° C. incubator for an overnight incubation and the viability of the cells was tested by XTT assay.

Figure 6:
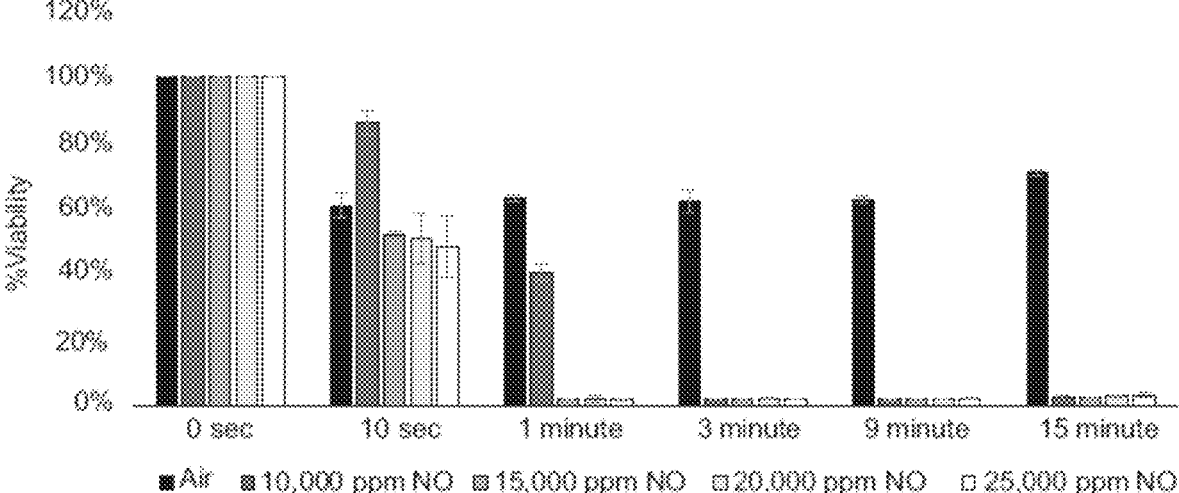
FIG. 6 is a bar graph showing the effect of 10,000-25,000 ppm NO or air on Panc02.03 cells in-vitro.

The obtained data is presented in FIG. 6 and shows less than 5% viability of Panc02.03 cells after exposure to 10,000 ppm-25,000 ppm gNO for 1-15 minutes.

Examples 7 and 8

The effect of continuous gaseous nitric oxide (gNO) at 10,000 ppm, 15,000 ppm, 20,000 ppm, or 25,000 ppm, compared to air (control), on the survival of LLC1 cancer cell line was tested. LLC1 cells were prepared in DMEM medium and suspended in 96-well plates. The plates were placed inside an approx. 2 liter exposure chamber. The plates were exposed to the gas by filling the chamber with gNO for 10 seconds, or 1, 3, 9 or 15 minutes. After exposure, the plates were placed in a 5% $CO_2$, 37° C. incubator for an overnight incubation and the viability of the cells was tested by XTT assay.

The obtained data is presented in FIG. 7 and shows less than 5% viability of LLC1 cells after exposure to 10,000 ppm-25,000 ppm gNO for 3-15 minutes.

In an additional set of experiments, the plates were exposed to the gas (at 20,000 ppm or 50,000 ppm) by filling the chamber with gNO for 3 minutes. After exposure, the plates were placed in a 5% $CO_2$, 37° C. incubator for an overnight incubation and the viability of the cells was tested via Annexin V—Propidium Iodide apoptosis-necrosis assay.

The obtained data is presented in FIGS. 8A-C and shows that 80%-90% of LLC1 cells are at late apoptosis after exposure to 20,000 ppm or 50,000 ppm gNO for 3 minutes, whereby nearly no apoptosis is observed for the air-exposed cells.

Examples 9-11

The effect of local administration of 10,000-50,000 ppm gNO on CT26 tumor bearing mice was tested.

BALB/c female and male mice were obtained from Almog Diagnostic that purchased them from Envigo, Israel. The mice were 7-8 weeks of age. Animal care and experimentation were performed in accordance with the Bar-Ilan University guidelines.

CT-26, a colon carcinoma cell line was induced in a BALB/c mouse by chemical carcinogenesis.

Cells were cultured in Roswell Park Memorial Institute (RPMI) 1640 supplemented with 100 U/ml penicillin, 100 μg/ml streptomycin, 2 mM L-glutamine; 1 mM sodium pyruvate; 1% non-essential amino acid solution; 10% fetal calf serum. Cultures were maintained at 37° C. in a humidified incubator with a 5% $CO_2$ atmosphere.

Mice were inoculated subcutaneously with $5 \times 10^5$ CT-26 cells suspended in 100 µL Hank's Balanced Salt Solution (HBSS) into the low lateral side of the back. Local tumor growth was determined by measuring two mutually orthogonal tumor diameters with a caliper. The volume of the tumor was calculated using the formula: $Vol=D1 \times D2 \times D2/2$, where D1, D2 are two mutually orthogonal tumor diameters.

Air-1 is a female Balb/c mouse that was treated twice. On day 0 the tumor volume was 64.85 mm³. The treatments were: Day 0—Air was administered intra-tumoral by a needle for 2-3 minutes at a flow rate of 0.2 using a 3 L cylinder; Day 8—gNO at 10,000 ppm was administered for 6 minutes intra-tumoral by a 23 G needle, such as shown in FIG. 11B, at a flow rate of 0.3 LPM. This was followed by air administration for 4 minutes administered to the outer layer of the tumor using a cap, such as shown in FIG. 11C. An exemplary system is also shown in FIGS. 23 and 36.

NO-1 is a female Balb/c mouse and was treated once. On day 0 the tumor volume was 24.79 mm³. gNO at 10,000 ppm at a flow rate of 0.9 LPM (liter per minute) was administered to the outer layer of the tumor by a perforated flask, such as shown in FIG. 10E., and as also illustrated in FIG. 22, for 10 minutes. Then, the skin was removed from the tumor, and the tumor was re-exposed to gNO via a perforated flask filled with gNO using the same parameters.

NO-2 is a male Balb/c mouse and was treated 3 times. On day 0 the tumor volume was 38.51 mm³. Day 0—gNO at 50,000 ppm was administered for 3.8 minutes at a flow rate of 0.9 using a cap. Day 5: gNO at 10,000 ppm was administered for 30 minutes using a cap. The shell was removed from the original tumor and gNO was delivered for 10 minutes using a cap, such as shown in FIG. 11C. Then, gNO was delivered intra-tumorally by a 23 G needle such as shown in FIG. 11B at 0.3 LPM for another 10 minutes, using an intra-tumoral channel. The tip of the needle was directed at the outside area. Lastly, gNO was delivered for 10 minutes intra-tumorally by a 23 G needle such as shown in FIG. 11B. Day 11: gNO at 10,000 ppm was delivered to the tumor for 5 minutes and at a flow rate of 0.3 LPM, using a 23 G needle and an intra-tumoral channel.

Figure 9:
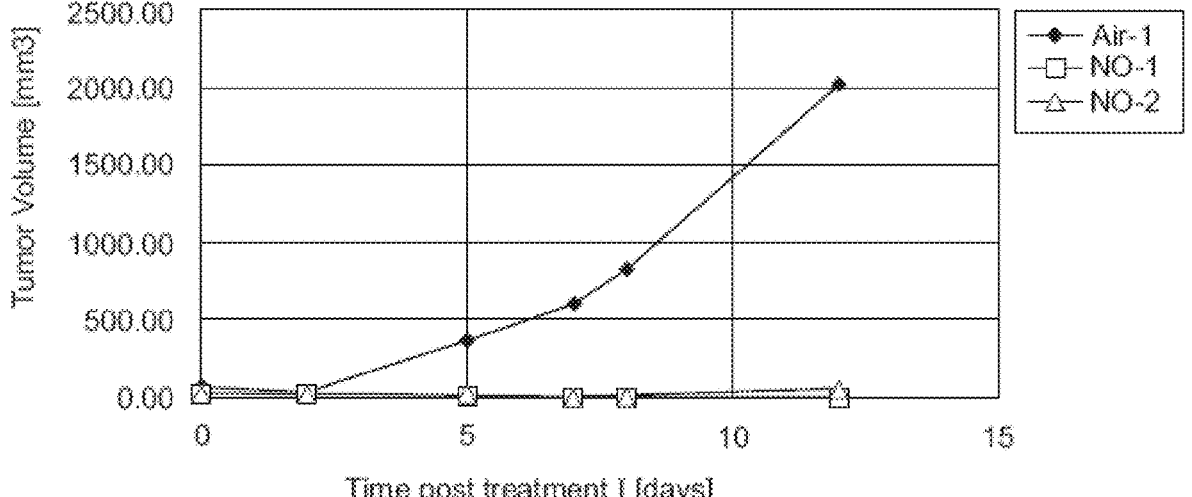
FIG. 9 presents comparative plots showing the effect of air or of gNO at 10,000 ppm or 50,000 ppm on CT26 tumor volume, in vivo.

The obtained data is presented in FIG. 9 and shows that the air-treated tumor is more than times bigger than the gNO-treated tumors 12 days post treatment 1.

In an additional set of experiments, aluminum disposable gas cylinders were used. A flow meter was connected directly to the cylinder, to which a gas delivery tubing was connected. The tumor was inserted into a small flask trough a 1 cm hole and a plastic holder. A small hole at the bottom of the flask enabled to lower the pressure inside the flask. The gNO tubing was connected to the cap of the flask as shown in FIG. 10E. The flask was filled with gNO at 10,000 ppm in $N_2$ at a flow rate of 0.9 Liter Per Minute (LPM) for 20 minutes: 10 minutes without the removal of the skin from the tumor and additional 10 minutes after removal of the skin with a scalpel.

FIGS. 10A-D present photographs taken before treatment (FIG. 10A) and 1 minute (FIG. 10B), 9 days (FIG. 10C) and 14 days (FIG. 10D), post treatment. As can be seen, the tumor was destructed by the gNO treatment.

FIG. 10F presents the tumor volume following the treatment and shows 100% CT-26 tumor destruction 1-17 days post treatment with 10,000 ppm gNO.

In an additional set of experiments, stainless steel needles were used for intra-tumoral administration. Two types of gas cylinders were used—aluminum disposable and non-disposable cylinders.

For the non-disposable cylinders, a pressure regulator was connected directly to the cylinder, which was connected to the flow meter that was connected to the gNO tubing, to which a 23 G hypodermic stainless steel was connected.

For the disposable cylinders, a flow meter was connected directly to the cylinder, to which a 23 G hypodermic stainless-steel needle was connected through a gas delivery tubing, such as illustrated in FIG. 23. gNO at two doses was used: 10,000 or 50,000 ppm gNO in $N_2$, the flow rate was set to 0.1-0.3 Liter Per Minute (LPM) and the exposure time was 2-10 minutes in a pulsed manner. Additionally, gNO at 10,000 ppm-50,000 ppm was administered for 4 minutes to the outer layer of the tumor at 0.3-1 LPM by a cap. An air treated tumor bearing mouse served as the control group.

Treatment I (day 0) and II (day 8) were applied to all mice. Treatment III (day 14) was applied to mouse NO-5 only.

Treatment I: gNO at 50,000 ppm was administered, intra-tumoral by a 23 G hypodermic needle, such as shown in FIG. 11B for 2-3 minutes at a flow rate of 0.2 LPM using a 3 L cylinder.

Treatment II: gNO at 10,000 ppm was administered for 6 minutes intra-tumorally by a 23 G needle, such as shown in FIG. 11B. Then, gNO at 10,000 ppm was administered for 4 minutes to the outer layer of the tumor by capping, such as shown in FIG. 11C. The flow rate was 0.3 LPM.

Treatment III: gNO at 50,000 ppm was administered by a cap such as shown in FIG. 11C to about 1 cm×0.5 cm cut at a flow rate of 0.9 LPM using a 3 L cylinder for 10 minutes.

The obtained data is presented in FIG. 11A and shows CT-26 tumor growth inhibition in ⅔ mice in response to gNO treatment compared to air treatment. These mice were treated with nitric oxide at 50,000 ppm administered for 2-3 minutes at a flow rate of 0.2 LPM using a 3 L cylinder. Nine days later nitric oxide at 10,000 ppm was administered for 6 minutes intra-tumorally by a 23 G needle. Then, nitric oxide at 10,000 ppm was administered for 4 minutes to the outer layer of the tumor.

Example 12

The effect of continuous gaseous nitric oxide (gNO) at 50,000 ppm on a solid CT-26 tumor ex-vivo was tested.

A 65 mm³ CT-26 tumor was excised and stored in PBS at 25° C. for 1 hour. One half of the tumor was exposed to 50,000 ppm gNO in an acrylic glass box at a volume of about 1.7 L for 6 minutes, 0.9 LPM. The remaining portion of the tumor was exposed to air.

A non-disposable NO cylinder was used for delivering gNO. A pressure regulator was connected directly to the cylinder. A flow meter was connected to the regulator. The gas delivery line was connected to the flow meter. The NO gas tubing was inserted to the box through a 1 cm hole. An additional 0.2 cm hole permitted the reduction of the pressure inside the box.

Figure 12A:
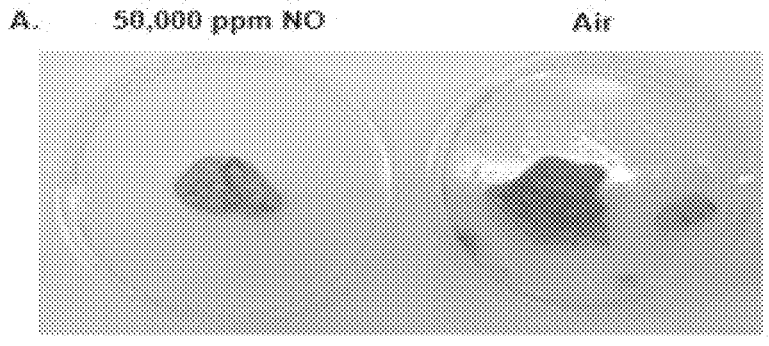
FIGS. 12A-B present photographs showing the effect of air or 50,000 ppm gNO on CT-26 tumor cells ex-vivo, outside (outer layer of) the tumor tissue (FIG. 12A) and inside (inner layer of) the tumor tissue (FIG. 12B).
Figure 12B:
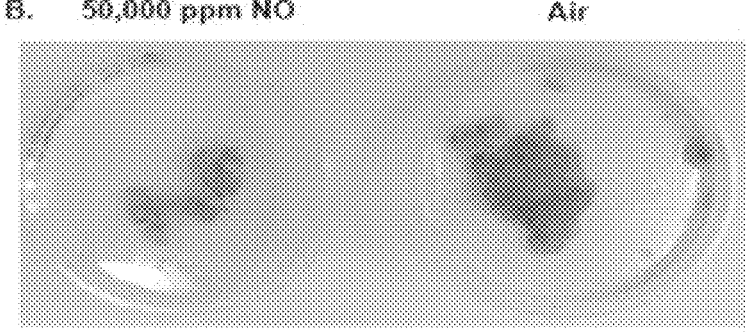

FIGS. 12A-B present the obtained data, and demonstrate the effect of continuous exposure of a CT-26 solid tumor to 50,000 ppm gNO or air, ex-vivo. FIG. 12 A presents the outer layer of the nitric oxide exposed tissue. FIG. 12 B presents the inner part of a nitric oxide exposed tissue.

Example 13

BALB/c male mice were obtained from Almog Diagnostic Ltd. (Almog). Almog purchased the mice from Envigo, Israel. The mice were 8-10 weeks of age. Animal care and experimentation were performed in accordance with the Bar-Ilan University guidelines. Institutional Animal Care and Use Committee (IACUC) approval number #67-09-2019.

Mice were inoculated with CT26 cancer cells. CT26 is a colon carcinoma cell line induced in a BALB/c mouse by a chemical carcinogenesis. Cells were cultured in Roswell Park Memorial Institute (RPMI) 1640 supplemented with 100 U/ml penicillin, 100 µg/ml streptomycin, 2 mM L-glutamine; 1 mM sodium pyruvate; 1% non-essential amino acid solution; 10% fetal calf serum. Cultures were maintained at 37° C. in a humidified incubator with a 5% CO2 atmosphere.

Mice were inoculated subcutaneously with $5 \times 10^5$ CT-26 cells suspended in 100 µL Hank's Balanced Salt Solution (HBSS) into the right flank, as shown in FIG. 13 (see, for example, upper right photograph). Local tumor growth was determined by measuring two mutually orthogonal tumor diameters with a caliper. The volume of tumor was calculated using the formula: Vol=D1×D2×D2/2, where D1, D2 are two mutually orthogonal tumor diameters.

CT26 tumor bearing mice were treated with 25,000 ppm gNO.

The gas was delivered into the tumor by a 23 G hypodermic needle for 15 minutes, at a flow rate of 0.25 LPM and outlet pressure of about 3.5 Bar using standard pressure regulators and flow meters. A week later, all mice were re-treated using the same protocol.

FIG. 13 presents photographs of 2 mice of the gNO treated group (out 4 mice in the group) which were cured (50%). The photographs show the cured flank of these mice 44 days post the first treatment.

Example 14

The tumor of a CT26 tumor bearing mouse was exposed to 200,000 ppm gNO (200,000 ppm gNO in 800,000 ppm nitrogen) for 2 seconds using a digital mass flow controller set to 0.01 LPM. In this setting, a valve is placed next to the pressure regulator, enabling manually stopping the flow. The valve was opened when the needle was in the tumor, resulting in an immediate swelling of about 1-2 cm³ of the tumor. The treatment was immediately stopped, and the mouse was transferred to its cage for recovery.

FIG. 14 presents photographs of the treated area before (upper photograph) and 9 days after (lower photograph) the gNO treatment, and show that that the tumor disappeared.

Figure 15A:
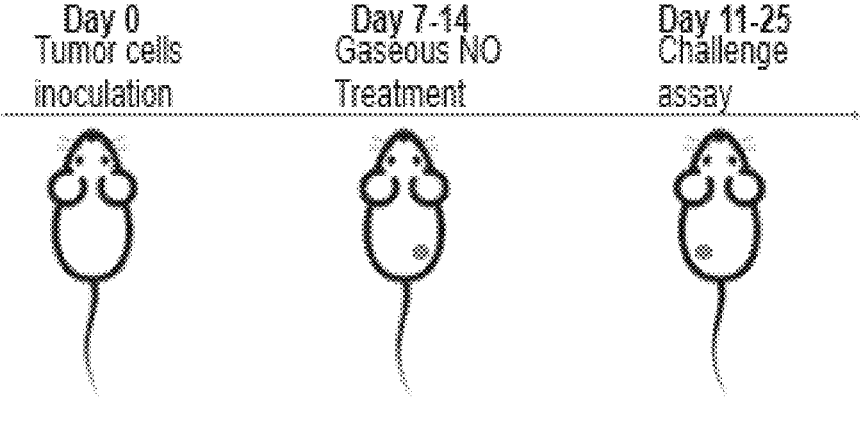
FIGS. 15A-B present a schematic depiction of a challenge assay in which tumors of LLC1 tumor-bearing mice were treated with 50,000 ppm NO for 10 minutes, and 14 days post this gNO treatment, mice were re-inoculated with LLC1 cells (FIG. 15A), and a bar graph showing the percentage of challenge tumor take 9 days post LLC1 cancer cell re-inoculation (FIG. 15B). Naïve mice, inoculated with LLC1 for the first time, served as the control group.

Examples 15-17 gNO local administration was tested in a Challenge assay, as depicted in FIG. 15A, in order to evaluate whether treating the primary tumor by gNO based ablation stimulates an anti-tumor immune response that results in rejection of a secondary tumor inoculation. A secondary, "challenge", tumor cells inoculation also serves as a metastasis model.

LLC1 tumor-bearing mice were treated with 50,000 ppm NO administered intra-tumorally by a 23 G hypodermic needle for 10 minutes. Up to 2 weeks post the first gas treatment all gas-treated mice were re-inoculated with 2.5× $10^5$ LLC1 cells suspended in 100 µL HBSS into the left flank. Naïve mice inoculated with $5 \times 10^5$ CT-26 cells served as an internal control for cells' quality.

Figure 15B:
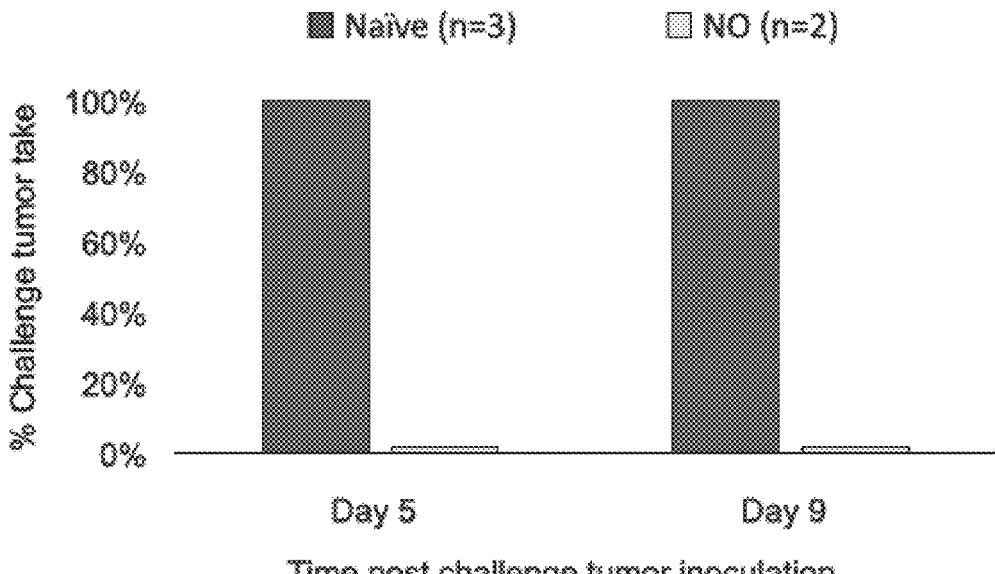

The obtained data is presented in FIG. 15B, and show the % of mice that developed a secondary tumor, as determined via palpation of the tumor cell inoculation site.

As can be seen, all naïve mice developed a tumor already 5 days post challenge tumor inoculation, whereby none of the gas-treated mice developed a secondary tumor, also 9 days post challenge tumor inoculation.

Figure 16A:
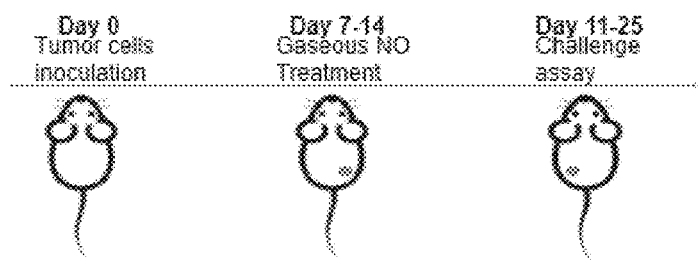
FIGS. 16A-E present a schematic depiction of a challenge assay in which tumors of 4T1 tumor-bearing mice were treated with 50,000 ppm gNO or nitrogen gas for 10 minutes, and 14 days post this gNO treatment, mice were re-inoculated with 4T1 cells (FIG. 16A), comparative plots showing the average primary tumor volume after gaseous nitrogen or gNO treatment (FIG. 16B), comparative plots showing the average challenge tumor volume 10 days post re-inoculation of cancer cells (FIG. 16C), a bar graph showing the percentage of challenge tumor take 10 days post 4T1 cancer cells re-inoculation with Naïve mice, inoculated with 4T1 for the first time being the control group (FIG. 16D), and a bar graph showing the number of mice that developed a challenge tumor 10 days post cancer cell re-inoculation in each treatment or control group.

In another challenge assay, 4T1 tumor-bearing mice were treated with 50,000 ppm gNO administered intra-tumorally by a 23 G hypodermic needle for 10 minutes, and the effect of a local treatment with gNO on the primary tumor as compared to nitrogen was tested, as depicted in FIG. 16A. Fourteen days post gNO treatment, mice were re-inoculated with $10 \times 10^5$ 4T1 cells subcutaneously (s.c.) (challenge assay). The percentage of tumor take was monitored by caliper measurements 2-3 times a week for 10 days. Naïve mice, inoculated with 4T1 for the first time, served as the control group. Up to 2 weeks post the first gas treatment all gas treated mice were re-inoculated with $10 \times 10^5$ 4T1 cells suspended in 100 µL HBSS into the left flank. In addition, naïve mice inoculated with $10 \times 10^5$ 4T1 cells served as an internal control for cells' quality.

Figure 16B:
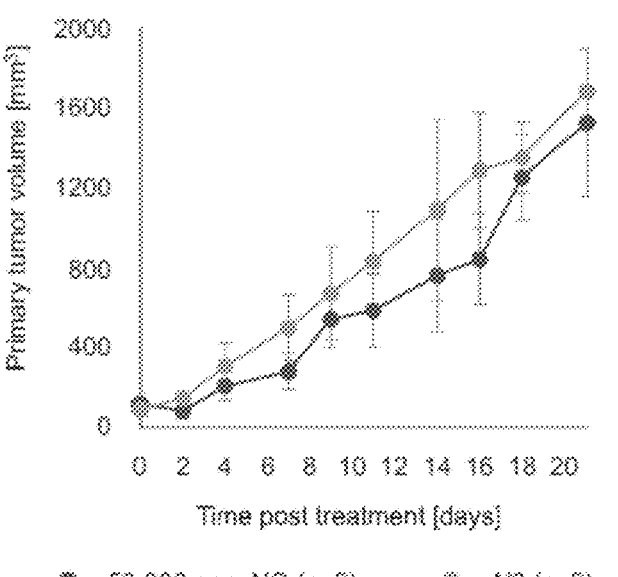

FIG. 16B presents the change in tumor volume following the first gNO local administration.

Figure 16C:
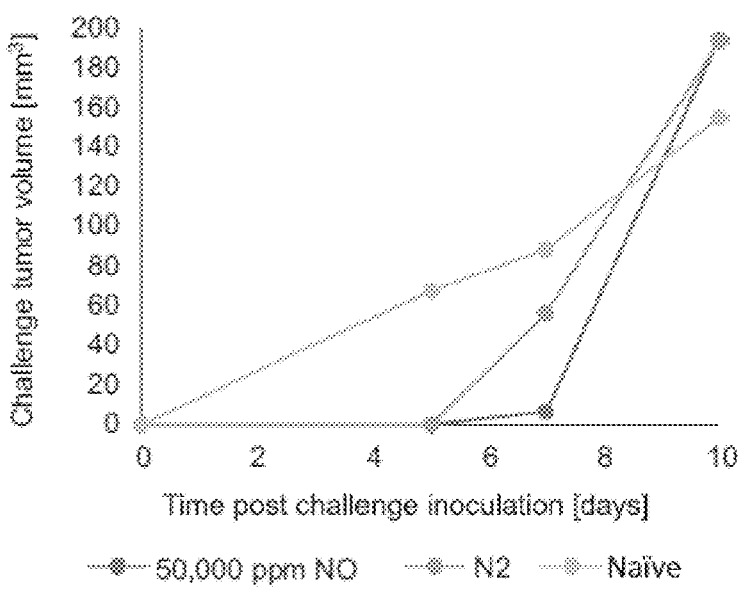
Figure 16D:
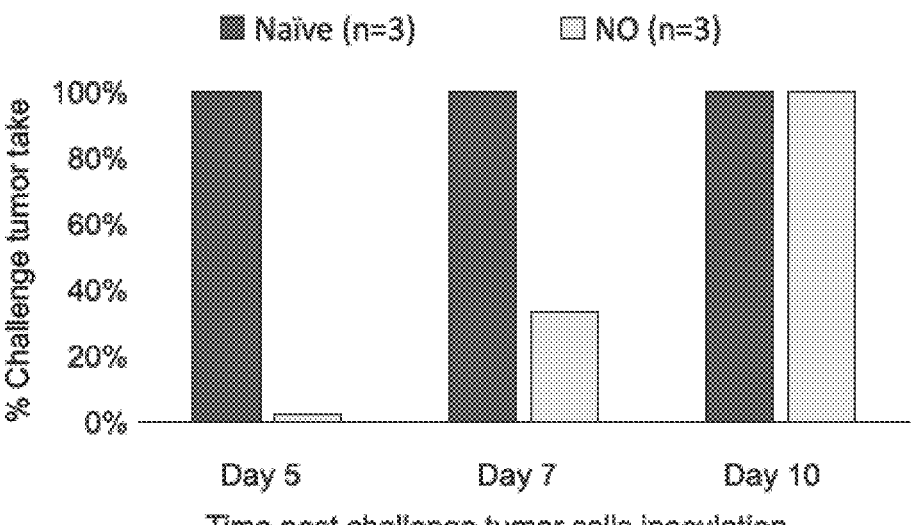
Figure 16E:
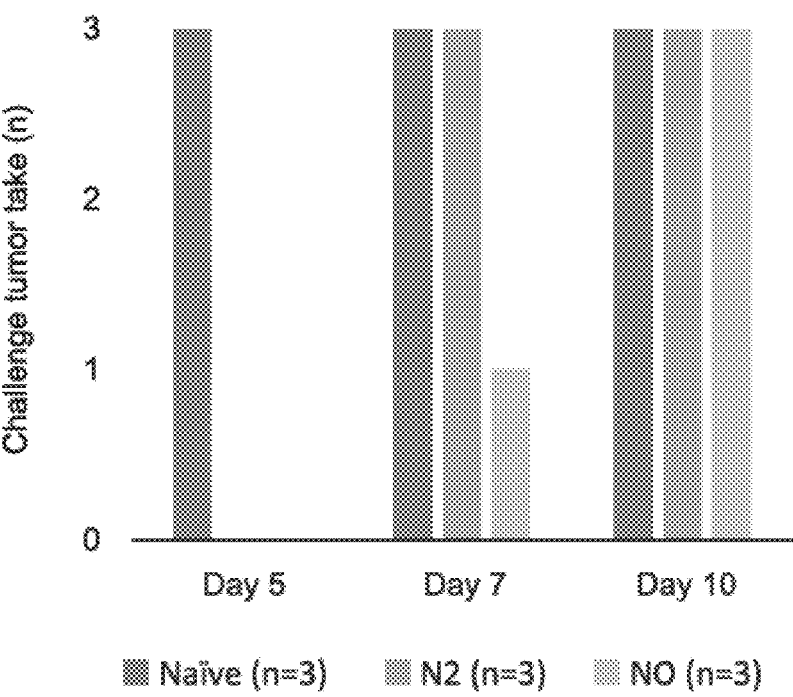

FIGS. 16C-16E present the average challenge tumor volume. As can be seen in FIG. 16C, all naïve mice developed a tumor 5 days post challenge tumor inoculation, while all the gas-treated mice (gNO—and nitrogen-treated mice) have not developed a secondary tumor 5 days post challenge tumor inoculation. As can be seen in FIGS. 16D and 16E, a delay in the challenge tumor take was achieved via gNO treatment, compared to non-treated nice and nitrogen-treated mice.

Figure 17A:
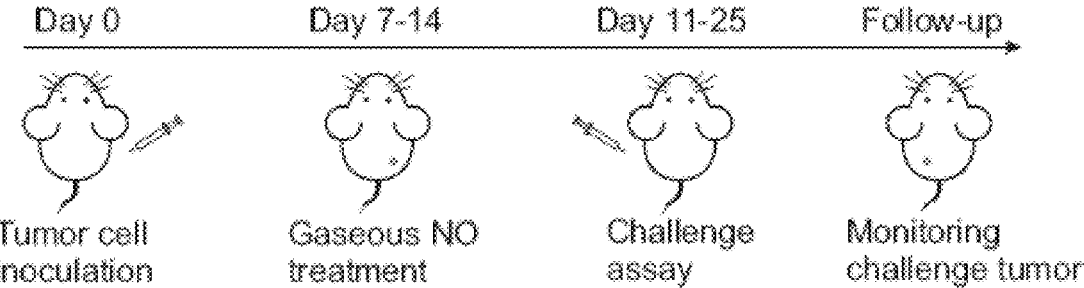
FIGS. 17A-B present a schematic depiction of a challenge assay in which tumors of CT26 tumor-bearing mice were treated with 25,000 ppm gNO for two 15 minute-cycles, 50,000 ppm gNO for 10 minutes or 200,000 ppm gNO for 2-35 seconds, and up to 14 days post this gNO treatment, mice were re-inoculated with CT26 cells (FIG. 17A), and a bar graph showing the percentage of CT26 challenge tumor take after re-inoculation (FIG. 17B). Naïve mice, inoculated with CT26 for the first time, served as the control group.

In another challenge assay, the tumors of CT26 tumor-bearing mice were treated with 25,000-200,000 ppm gNO delivered into the tumors using 23 G hypodermic needles, as depicted in FIG. 17A.

CT26 tumor-bearing mice treated with 25,000 ppm for 30 minutes, were re-inoculated with CT26 tumor cells 12 days after treatment (n=1) and 14 days after treatment (n=1). The percentage of visible challenge tumor take was assessed 2-3 times a week for more than 50 days.

An additional group of CT26 tumor-bearing mice were treated with 50,000 ppm for 10 minutes, and were re-inoculated with CT26 tumor cells 7 days (n=1) or 9 days (n=1) after treatment. The percentage of challenge tumor take was assessed 2-3 times a week for 12 days.

An additional group of CT26 tumor-bearing mice were treated with 200,000 ppm for 2-35 seconds, were re-inoculated with CT26 tumor cells 14 days (n=2) post treatment. The percentage of visible challenge tumor take was assessed 2-3 times a week for more than 50 days.

Naïve mice, inoculated with CT26 for the first time, served as the control group.

Figure 17B:
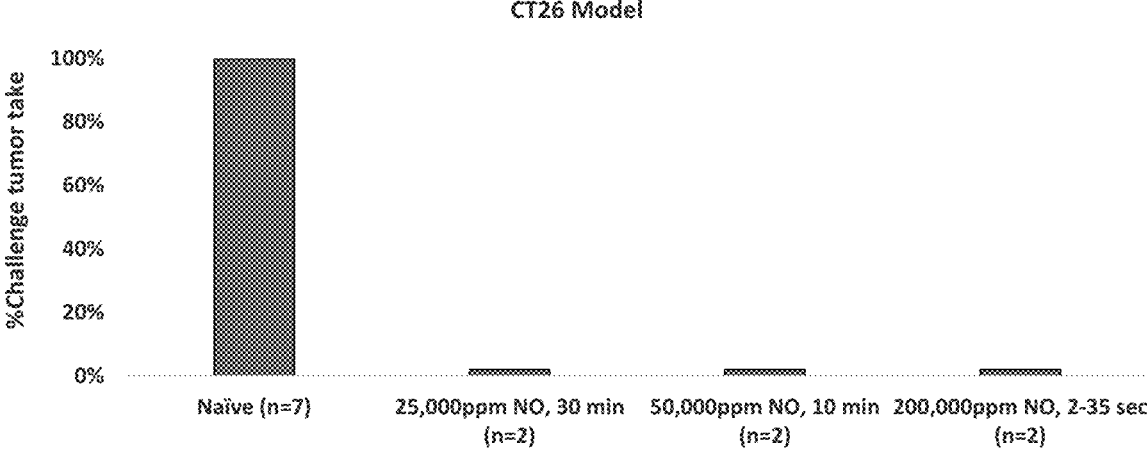

The obtained results at the end of the follow-up period are presented in FIG. 17B and show that all NO-treated mice rejected a secondary CT26 tumor cell inoculation as compared to 100% tumor take in the naïve mice control group.

Examples 18 and 19

Balb/c mouse was inoculated with 500,000 CT26 cells to the right flank. CT26 tumor was treated with 25,000 ppm NO for 15 minutes at a flow rate of 0.25 LPM. Seven days post gas treatment, this mouse was treated once again using the same protocol. Twelve days post the first NO treatment, this mouse was re-inoculated with 500,000 CT26 cells to the left flank. A third inoculation of cancer cells was performed 30 days post the second cell inoculation, using mouse breast cancer cells, was performed as well and the growth of a third inoculation of breast cancer cells, 4T1 cells. Forty-four days post challenge assay start (second inoculation), this mouse was sacrificed, and his spleen was harvested and preserved in RPMI-based media at 4° c. until processing of it. The spleen was processed into a sterile 35 mm culture dish containing 5 ml of RPMI-based media. Any extra connective tissues or fat was trimmed from the spleen. The flat end of a plunger was used to mince the spleen by crushing the spleen to release the splenocytes. A 70 μm strainer was primed by passing 1 ml of PBS through it and placed on a sterile 50 mL conical tube. The pellet was collected and transferred through the strainer via a 5 mL serological pipette. The strainer was washed with 3 mL of RPMI-based media. Tube will be centrifuged at 300×g for 10 minutes. The supernatant was discarded and resuspended in Ammonium-Chloride-Potassium (ACK) based solution to lyse red blood cells. After incubation, RPMI-based media was added, and cells will be centrifuged twice at 300×g for 10 minutes.

The splenocytes extracted from the spleen of CT26 immunized mouse were mixed with CT26 cells at a ratio of 1 CT26 cells: 2-10 splenocytes cells and inoculated to naïve mice.

The assay scheme is presented in FIG. 18A.

A third inoculation of 4T1 cancer cells, using mouse breast cancer cells, was performed as well and the growth of a third inoculation of breast cancer cells was inhibited.

The obtained data is presented in FIG. 18B and FIG. 18C. As can be seen in FIG. 18B, the growth of wild type CT26 cells that were inoculated to naïve mice together with splenocytes extracted from CT26 immunized mice is inhibited, compared to wild type CT26 cells that were inoculated to naïve mice alone. As can be seen in FIG. 18C, the growth of CT26 cells that were mixed with splenocytes at a ratio of 1:2 was inhibited in 33% (1 out of 3 mice) of inoculated mice 30 days post inoculation, and the growth of CT26 cells that were mixed with splenocytes at a ratio of 1:10 was inhibited in 67% (2 out of 3 mice) of inoculated mice 30 days post inoculation.

The potency of the extracted splenocytes to eliminate wild-type CT26 cells in-vitro was also tested by plating 10,000 CT26 cells per well in a 96-well plate and adding splenocytes at a ratio of 1-10 splenocytes to a single CT26 cell. CT26 cells viability was tested after 46 hours incubation by XTT. The obtained data is presented in FIG. 19 and show that about 60-70% of CT26 cells remain viable upon incubation with splenocytes at a ratio greater than 5. A dose-response effect is seen only in 1:1 to 1:5 ratios.

Example 20

The following in vivo experimental procedures were carried out in accordance with the protocol approved by the Ethics Committee on the Use and Care of Animals. Institutional Animal Care and Use Committee (IACUC): IL-20-3-149.

CT26 tumor-bearing mice were treated with 20,000 ppm and 50,000 ppm gNO intra-tumorally for 5 minutes. Up to fourteen days post gNO treatment, all tumors were excised, and the recurrence rate was monitored for 89 days post-excision. Tumor recurrence was detected 17 days post treatment.

Figure 20:
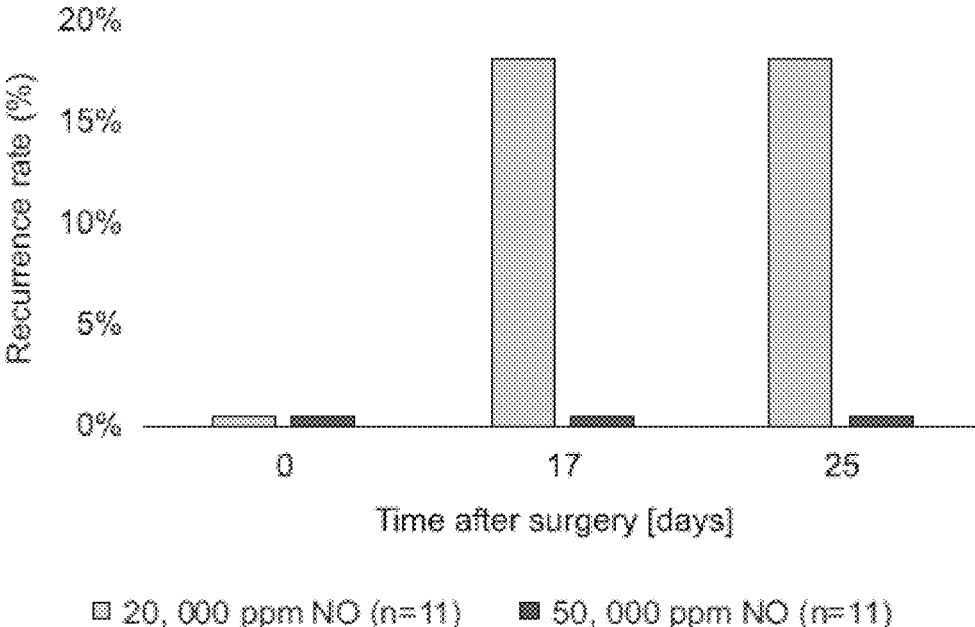
FIG. 20 is a bar graph showing the effect of combined 20,000 ppm or 50,000 ppm gNO and surgery on CT26 tumor recurrence.

The obtained data is presented in FIG. 20 and show that about 18% of the 20,000 ppm gNO-treated tumor recurred 17 days post-surgery (excision), while 0% recurrence was observed in the 50,000 ppm gNO-treated group, 17 days post surgery (FIG. 20).

Example 21

CT26 tumor-bearing male mice were treated with 20,000 ppm and 50,000 ppm gNO intra-tumorally for 5 minutes.

Figure 21A:
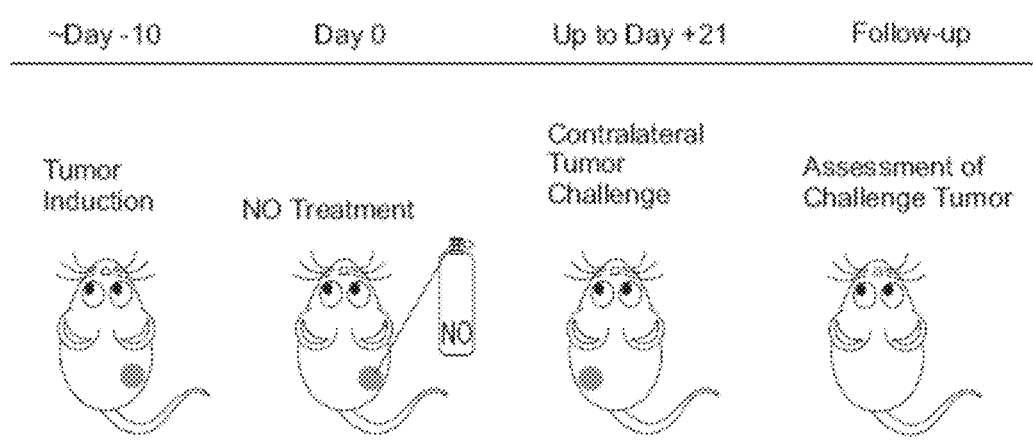
FIGS. 21A-D present a schematic depiction of a challenge assay in which tumors of CT26 tumor-bearing mice were treated with 20,000 ppm or 50,000 ppm gNO for 5 minutes and 14 days post this treatment, all tumors were excised and mice were re-inoculated with CT26 cells (FIG. 21A), a bar graph showing the percentage of challenge tumor take in each group compared to Naïve mice (FIG. 21B), comparative plots showing the tumor volume up to 21 days post re-inoculation (Challenge) (FIG. 21C), and a bar graph showing survival of mice in each group (FIG. 21D).
Figure 21B:
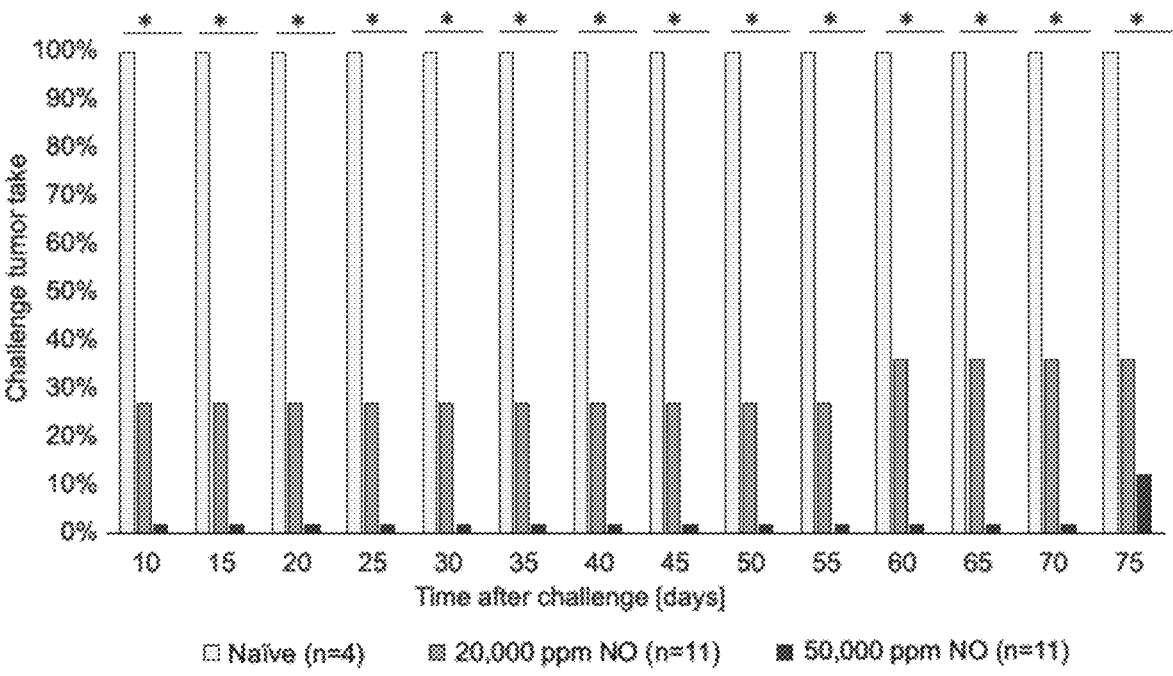
Figure 21C:
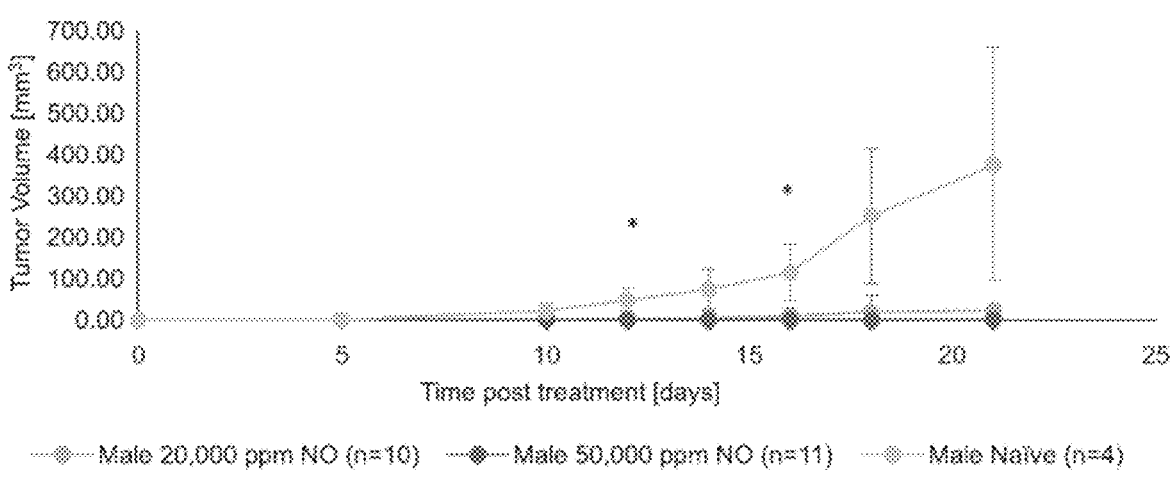
Figure 21D:
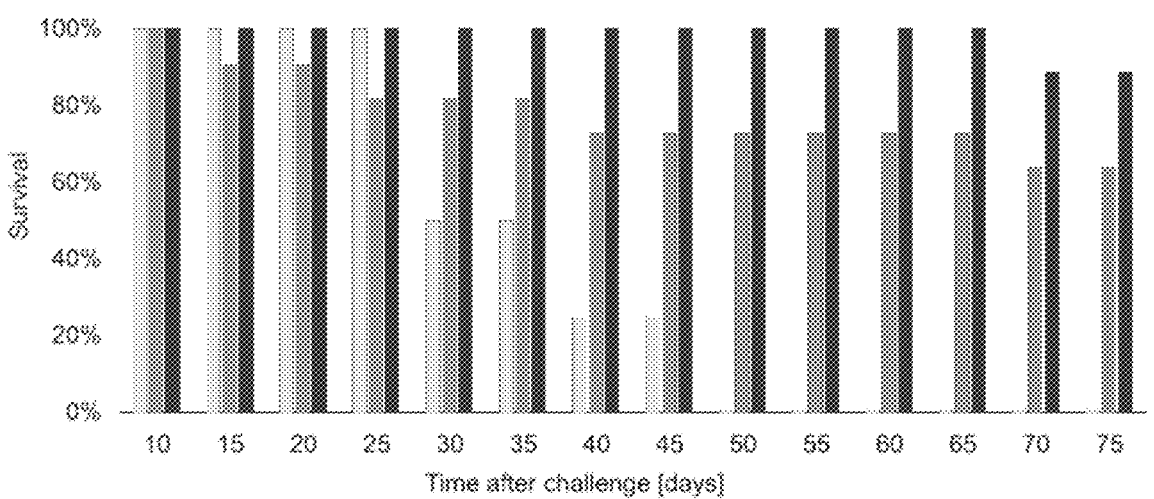

Fourteen days post gNO treatment, all tumors were excised. A week post surgery, all mice were re-challenged via a second inoculation of 5×10⁵ CT26 cells, and tumor take and survival were monitored during about 75 days, as depicted in FIG. 21A. FIGS. 21B-D present the data obtained for the percentage of challenge tumor take was monitored (FIG. 21B), the challenge tumor volume (FIG. 21C) and survival (FIG. 21D), and clearly show no tumor development in the gNO-treated, and 100% survival in mice treated with 50,000 ppm gNO, compared to nearly no survival in non-treated mice.

Example 22

Figure 37A:
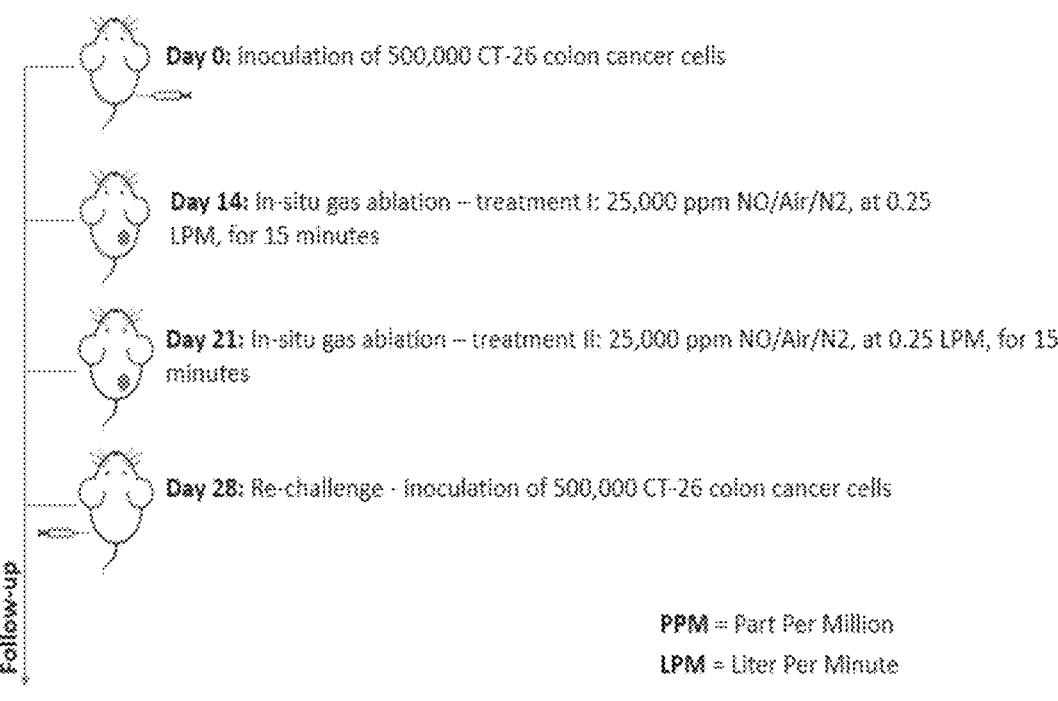
FIGS. 37A-B present a schematic depiction of a challenge assay in which tumors of CT26 tumor-bearing mice were treated with 20,000 ppm gNO, air or nitrogen for two 15-min cycles and 14 days post this treatment, mice were re-inoculated with CT26 cells (FIG. 37A), a bar graph showing the percentage of tumor-free mice, without visible primary and challenge tumors in the control group, the air or nitrogen-treated group and gNO-treated group (FIG. 37B).

The effect of high-pressure gas treatment on stimulation of anti-tumor immune response was tested in a challenge assay as depicted in FIG. 37A.

Balb/c mice were inoculated subcutaneously (s.c) with the mouse colon cancer cell line, CT26. CT26 tumor-bearing mice were treated 25,000 ppm gNO, air or nitrogen supplied by Gordon Gas and Chemicals in 3.5-liter cylinders. The outlet pressure was set to 3.5-5.17 bars. Gas was delivered to the tumors via a 23 G needle and at a flow rate of 0.25 liter per minute (LPM) for two 15-minute cycles. At days 12-14 post gas treatment, all mice were re-inoculated s.c with CT26 tumor cells to the contralateral flank of all gas-treated mice. Naïve mice inoculated with CT26 cells for the first time served as a control to ensure that these cells were not defected on challenge day.

Figure 37B:
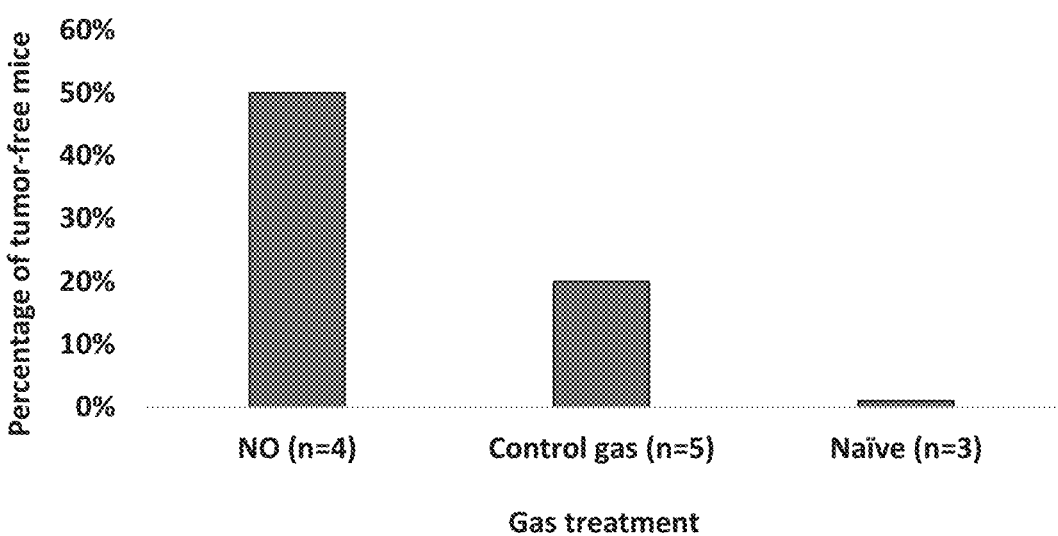

This challenge assay serves as model for metastasis development (secondary tumor). The obtained data is presented in FIG. 37B and show that while all naïve mice developed a tumor and were sacrificed when their tumor volume exceeded 2 cm³, three weeks post cells inoculation, all the gas-treated mice have not developed a secondary tumor. 50% of the gNO treated mice were tumor-free, with no primary and challenge tumors; 20% of the air or nitrogen-treated mice did not develop both visible primary and challenge tumors.

Example 23

The gNO treatment as described herein is utilized for preparing a personalized ex-vivo nitric oxide-based cancer vaccine. An autologous tumor or metastasis specimen is exposed to nitric oxide outside of the patient's body. The resulting nitric oxide-treated pool of cancer antigens is administered back to the patient for the purpose of engaging the immune response to react against systemic malignant cells.

A patient can be treated simultaneously with: (I) In situ nitric oxide cancer vaccination as described herein in any of the respective embodiments and is demonstrated in Examples 15-21 herein; (II) Ex vivo nitric oxide-based cancer vaccination as described herein in any of the respective embodiments and detailed in this example; and (III) Immune-stimulating agent or any other additional agent or adjuvant as described herein in any of the respective embodiments.

In general, in this cancer vaccination technique, the physician removes a tumor tissue sample from the patient. This sample is exposed to gaseous nitric oxide, for example, at from about 100 ppm to about 1,000,000 ppm, of from about 1,000 ppm to 1,000,000 ppm, or from 10,000 to 200,000 or from 20,000 to 200,000, or from 50,000 to 200,000 ppm, for a tome period of from 1 second to 10 hours, or from 1 minute to 2 hours, or from 1 minute to 60 minutes or from 10 minutes to 60 minutes, including any intermediate values and subranges therebetween.

The resulting nitric oxide-treated biomaterial is further purified to protein/peptide solution/non-viable cancer cells solution, or introduced to dendritic cells (DCs) to have loaded cancer antigen presenting cells.

The following describes an exemplary, non-limiting, procedure for preparing an ex vivo nitric oxide-based preparation of an individual cancer vaccine (personalized vaccine). Leukocytes and DCs Purification from Blood Samples:

Whole blood is collected from the patient by venipuncture in Ethylenediaminetetraacetic acid (EDTA)-treated collection tubes. Blood cells are then separated out in a process that includes centrifugation of all blood cells, followed by red blood cell lysis, while following methodologies known in the art. In an exemplary, non-limiting procedure, blood sample is centrifuged, for example, at about 250-350×g for, for example, about 5-10 minutes. Then, red blood cell lysis is performed via an appropriate buffer, such as, but not limited to, Ammonium-Chloride-Potassium (ACK). About 1-20 ml of the buffer is added to 1-10 ml of blood cells at room temperature for, for example, about 1-10 minutes. The blood sample is then centrifuged, for example, at about 250-350×g for, for example, about 5-10 minutes. Supernatant is discarded, and cells are re-suspended in 1-10 mL cold buffer such as, for example, cold phosphate buffered saline. Blood cells are then washed once again by centrifugation, for example, at about 250-350×g for, for example, about 5-10 minutes. Supernatant is discarded, and cells are re-suspended in 1-10 mL cold buffer such as cold phosphate buffered saline. Dendritic cells (DCs) are optionally further purified using bead-conjugated antibodies, recognizing DCs markers, such as CD11c. Purified DCs are optionally proliferated using appropriate cell culture media and/or cryo-preserved.

Cancerous Tissue Sample Processing:

(A) One or more samples of tumor tissue(s) is/are collected from the patient and further processed in a nitric oxide-based procedure. A non-limiting exemplary procedure includes one or both of A and B as described below, followed by C and optionally D and/or E, as described below. Single-cell suspension preparation: The tissue sample is processed to a cell suspension using the appropriate enzyme mixture, typically, but not limited to, collagenase and DNase enzymes. The tissue is then processed automatically using a cell dissociation device.

(B) Peptide suspension preparation: The tissue sample is processed to a peptide suspension via homogenization, enzymatic digestion, and sonication of the sample.

(C) Sample exposure to gaseous nitric oxide: Cells or tissue samples are plated onto tissue culture plates or dishes and placed inside a nitric oxide compatible chamber. Nitric oxide is supplied into the chambers via, for example, gas cylinders or generators.

(D) Purification: Bead-conjugated proteins of antibodies recognizing cell proliferation and viability markers are used to sort out active cancer cells. Alternatively, cancer cells are sorted out via appropriate protein and peptide filters. The output inactivated material is used for administration back to the patient.

(E) Cancerous material viability assessment: The viability of cells/tissues is assessed via standard cell viability assays, such as fluorescently labeling of death markers and measuring it via a flow cytometer, or cell proliferation-based assays. Inactivated material includes dead or non-proliferating cancer cells.

(F) Presentation of nitric oxide-treated cancer antigens to DCs from the patient: Obtained cancer antigens are introduced to DCs. For example, antigens obtained from previous steps are co-incubated with DCs from the patient, taken up and presented by them. The output antigen presenting DCs is used for administration back to the patient.

(G) Administration of the autologous cancerous nitric oxide processed material to the patient: The output material for administration back to the patient is either a solution, suspension, or implantation of a nitric-oxide treated tissue. The vaccination site is any part of the patient's body, such as, for example, the arm. The material is injected or implanted via any method, such as, but not limited to, intramuscularly, intratumorally, intraperitoneal, subcutaneously, intravenously. An additional agent can be injected before, simultaneously, or after cancerous material administration. This agent may be a cancer drug, an immune stimulating agent such as an adjuvant or an inhibitor of immune suppressor cells.

Figure 38:
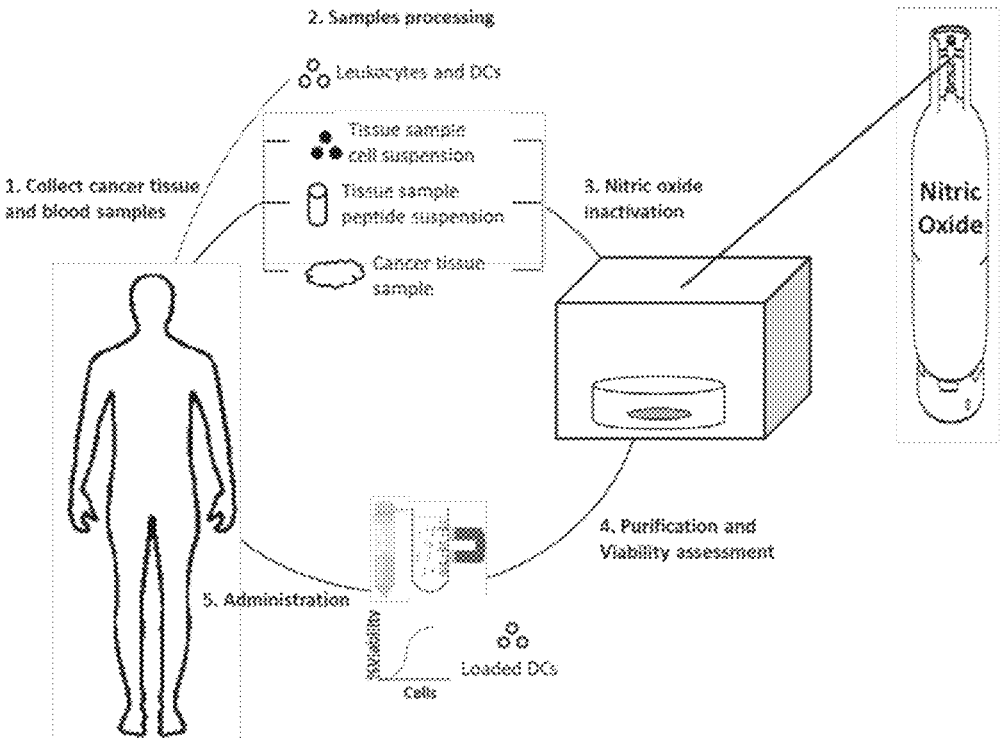
FIG. 38 presents a schematic illustration of an exemplary process of preparing an ex-vivo gNO-based personalized cancer vaccine.

An exemplary, non-limiting preparation of a personalized gNO-based cancer vaccine is presented in FIG. 38, which shows a five-step process as follows:

1. Cancer tissue and blood samples collection
2. Sample processing: single-cell or peptide suspension preparation or slicing of the tumor tissue sample.
3. Nitric oxide inactivation of cancer tissue/cell/peptide samples: exposure of the processed tissue to gaseous nitric oxide (e.g., as described herein), supplied from a gas cylinder or generator.
4. Sample purification and viability assessment: purification of dead/non-proliferating cells followed by viability assessment and/or loading of DCs with cancer antigens.
5. Administration of the resulting nitric oxide-based vaccine to the patient The gNO-based vaccine is tested in an animal model, for example, a mice model.

Mice at the age of 10-12 weeks are inoculated with cancer cells ($\sim 10^5$-$10^6$ cells per mouse) subcutaneously.

When the tumor volume is about 50 $mm^3$-500 $m^3$, the entire tumor or a sample is removed.

On tumor excision day, blood sample of about 100 $\mu$l-500 $\mu$l is collected.

The blood sample is centrifuged, for example, at 300×g for 10 minutes at room temperature;

The pellet is re-suspended in 0.1-1 ml buffer, for example, ACK buffer;

Blood cells are incubated with the buffer for 1-10 minutes;

1-10 ml of cold buffer (e.g., PBS) is added and cells are centrifuged, for example, at 300×g for 10 minutes at 4° C. Washing is repeated twice.

Bead-conjugated anti-CD11c antibodies are added and DCs are purified from the blood;

DCs are grown in an appropriate cell culture media until use.

Alternatively, or in addition, cancer tissue samples are treated as follows:

Sample is chopped, for example, by using a scalpel;

Tissue is thereafter dissociated using appropriate suitable enzyme mixture and cell-dissociator, and is homogenized, enzymatically digested and sonicated to a peptide solution.

Alternatively or in addition, tumor samples are plated in tissue culture plates or dishes, placed inside a nitric oxide compatible chamber and exposed to gaseous nitric oxide as described herein. Control samples are exposed to nitrogen gas or remain untreated. Gas exposure is performed, for example, from 1 to 60 minutes, at a flow rate of, for example, 1-10 LPM.

Live/proliferating cells are thereafter sorted-out using bead-conjugated antibodies recognizing viability cell markers. Proteins and peptides are purified using appropriate filters.

DCs are incubated with the resulting nitric oxide-treated biomaterials Tumor-bearing mice are divided into groups. One group is injected intratumorally and/or intravenously with gNO-treated cells, non-viable gNO-treated cells, gNO-treated proteins, and/or DCs expressing gNO-treated antigens. Another group is injected intratumorally and/or intravenously with nitrogen-treated cells, non-viable nitrogen-treated cells, nitrogen-treated proteins, and/or DCs expressing nitrogen-treated antigens. A third group is injected intratumorally and/or intravenously with non-treated cells, non-viable non-treated cells, non-treated proteins, and/or DCs expressing non-treated antigens.

All mice are then re-inoculated with the same cancer cells.

Primary and secondary tumor volume and mice survival are monitored.

An exemplary, non-limiting, protocol for a clinical study of the designed gNO-based personalized vaccine is as follows.

A physician removes a 0.1-3 grams tumor tissue sample from the patient.

A physician/healthcare staff collectS a 1-20 ml blood sample form the patient.

The blood sample is centrifuged, for example, at 300×g for 10 minutes at room temperature.

The pellet is re-suspended in a buffer (e.g., ACK buffer) an appropriate volume.

Blood cells are incubated with the buffer for 1-10 minutes.

1-10 ml of cold buffer (e.g., PBS) are added and cells are centrifuged, for example, at 300×g for 10 minutes at 4° C. this washing step is repeated twice.

Bead-conjugated anti-CD11c antibodies are added and DCs are purified/isolated from the blood.

The DCs are grown in appropriate suitable cell culture media until use.

The tissue samples are chopped using a scalpel, handled as described hereinabove and exposed to nitric oxide (e.g., 50,000 ppm for 10 minutes, at a flow rate of 1 LPM). Viability and proliferation of the cells is then evaluated as described hereinabove and live/proliferating cells are sorted out using bead-conjugated antibodies recognizing viability cell markers. Proteins and peptides are optionally also purified using appropriate filters.

The DCs are incubated with the obtained nitric oxide-treated biomaterials, and are administered to the patient by one or more of the following:

(I) DCs expressing nitric oxide-treated antigens are injected intravenously; (II) Dead nitric oxide-treated cancer cells and nitric oxide-treated protein/peptide solution are injected intramuscularly. (III) A mixture of (I) and (II) are injected into a specific tumor.

Total tumor burden in the patient is then assessed, for example via an imaging technique. The tumor volume of the injected outgrowth is also assessed separately.

Example 24

An exemplary system for local administration of gas, particularly, gNO, to a tumor (e.g., a tumor tissue) is described herein.

The system presented herein can effectively administer gaseous nitric oxide locally to treat tumors. Compared to conventional techniques, the system described herein is more targeted in treating tumors, particularly cancerous cells in vivo. The system described herein can effectively deliver gNO in treatment regimes, and can deliver gNO to target sites, with minimal damage, and preferably without damaging, healthy adjacent host cells, optionally and preferably while simultaneously identifying the target site and evaluating the effect of gNO local administration thereto.

Figure 39:
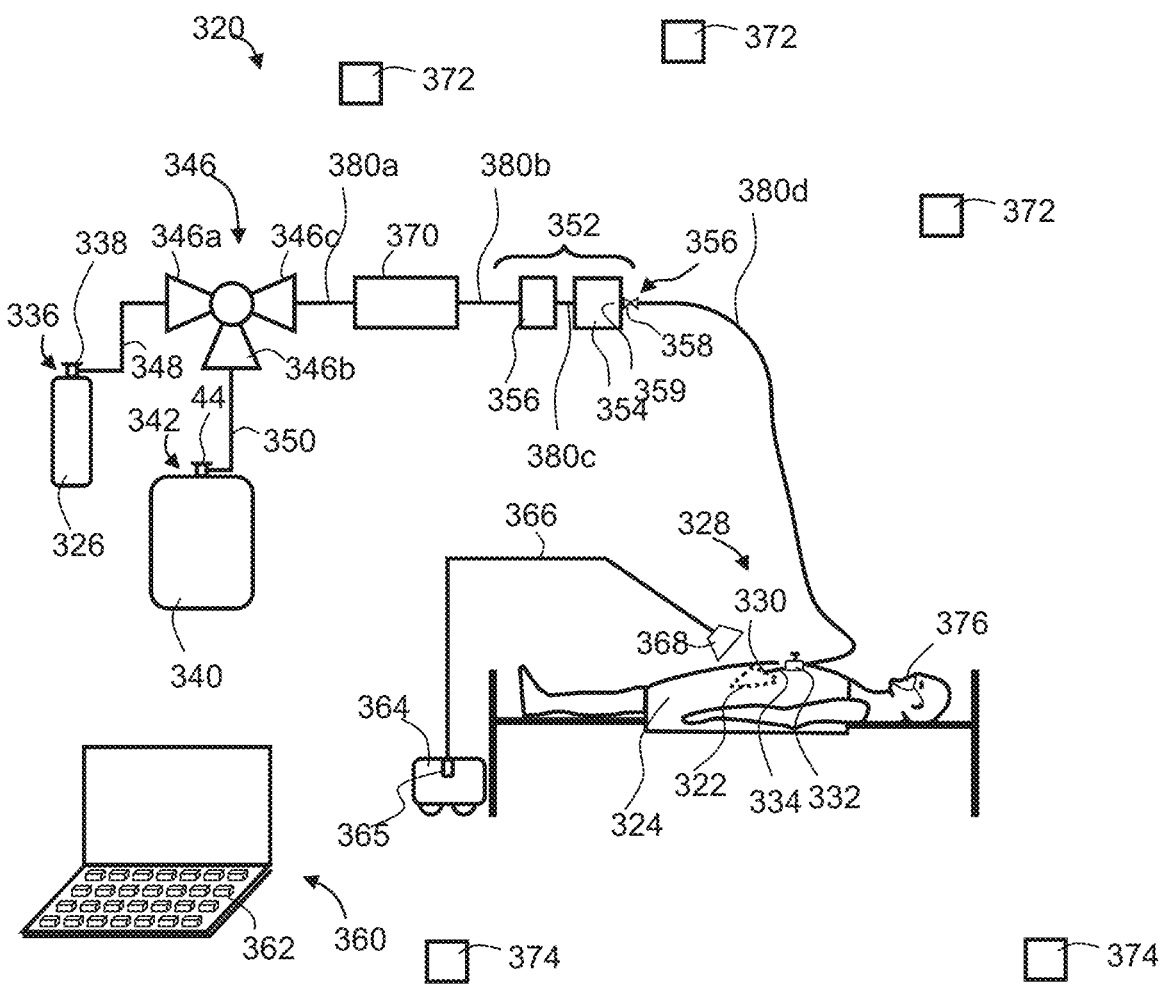
FIG. 39 is a schematic illustration of an exemplary system for delivery of gas to a tissue of a subject, according to some embodiments of the present invention.

Referring now to the drawings, FIG. 39 illustrates a system 320 for delivery of gas to a tissue 322 of a subject 324, according to some embodiments of the present invention. The subject 324 is optionally and preferably a mammalian subject, more preferably a human subject. The tissue 322 is typically a tumor or a metastasis, or a physiological cavity containing same, or any other administration site as described herein, and the gas is delivered for the purpose of treating the tumor or a tumor metastasis. In some embodiments of the present invention the tumor is a malignant tumor.

System 320 can therefore be used to treat many types of cancers, as described herein in any of the respective embodiments.

The gas is optionally and preferably gNO, but other therapeutic gases are also contemplated.

System 320 comprises a first container 326 containing the gas, and an applicator 328 having a distal end 330 arranged to deliver the gas to the tissue 322. The gas is delivered to applicator 328 via a gas flow line shown at 380d. The applicator 328 can be of any type that has an outlet through which a flow of gas can exit. Typically, but not necessarily, applicator 328 is a transcutaneous device, e.g., a cannula 332 that ends in a needle 334 or a sprayer. The needle 334 can be any suitable needle for delivering the gas (e.g., gNO) including, but not limited to, a perforated spray needle, non-perforated and non-spray needle, umbrella needle, or other needles. The needle can optionally be nano size, micron size or macro size needles. Also contemplated are embodiments in which applicator 328 is configured for spraying, or otherwise exposing the tissue to the gas, in an open or closed container (e.g., a container sized to conform to the contours of the tumor), or to fill a space or a physiological cavity containing one or more tumors with the gas.

First container 326 typically comprises an outlet 336 and a valve 338 mounted thereon. First container 326 is optionally and preferably disposable. This is particularly advantageous when the gas is toxic, as in the case of gNO, so that the disposable container can be connected to system 320 immediately before treatment, and disposed immediately after treatment, thus reducing the time at which the toxic substance is in the treating room. In various exemplary embodiments of the invention the volume of container 326 is sufficient small (e.g., less than 100 cc, or less than 90 cc, or less than 80 cc, or less than 70 cc, or less than 60 cc or less than 50 cc) so that the amount of gas in container is not more than the typical gas dose to be delivered to the tissue. This is particularly advantageous when the gas is toxic, as in the case of gNO, because in the event of undesired leakage of the gas into the treating room, the total amount of gas that can be leaked is small, compared to the size of the room, thus reducing the risk of inhaling a hazardous concentration of the gas by the subject 324 or medical personnel.

For example, when the gas is gNO, the immediately dangerous to life or health (IDLH) concentration is 100 ppm, and so the amount of gNO in container 326 is preferably less than $\frac{1}{10000}$ of a typical volume of a treating room, which is typically from about 40,000 liters to about 60,000. Thus, the volume of container 326 can be from about 10 cc to about 60 cc, and it can be filled with the gas at a volumetric concentration of from thousand ppm to several hundred-thousands ppm (e.g., 1,000-1,000,000 ppm), where "ppm" (parts per million) refers to the fraction (e.g., volumetric fraction) of the gas in a gas carrier. The gas carrier can be air, and preferably an inert gas such as nitrogen or argon, preferably nitrogen. In embodiments, the volume of first container 326 is from about 10 cc to about 3.5 L.

The gas pressure in container 326 is preferably low, e.g., less than 5 bar, e.g., from about 1 bar to about 5 bar. Alternatively, the gas pressure in container 326 can be higher (e.g., from about bar to about 20 bar).

Thus, the first container 326 can comprise from about 1,000 ppm to 1,000,000 ppm of the gas, or any intermediate subrange therebetween, for example, from about 1,000 ppm to about 200,000 ppm, or from about 1,000 ppm to about 100,000 ppm, preferably from about 10,000 ppm to about 500,000 ppm, or from about 10,000 ppm to about 200,000 ppm, or from about 10,000 ppm to about 100,000 ppm, or from about 20,000 ppm to about 100,000 ppm, or from about 25,000 ppm to about 100,000 ppm, or from about 25,000 ppm to about 75,000 ppm, or from about 10,000 ppm to about 50,000 ppm, or from about 50,000 ppm to about 100,000 ppm, including any intermediate values and subranges between any of the foregoing, or is about 50,000 ppm.

System 320 can further comprise a second container 340 containing a purging gas, and having an outlet 342 and a valve 344 mounted thereon. Preferably, the purging gas is non-hazardous to the subject, more preferably an inert gas, such as, but not limited to, nitrogen or argon. As the purging gas is non-hazardous, the volume of the second container 340 can be larger (e.g., times or 100 times or 1000 times larger) than the volume of container 326. The gas pressure in container 340 is preferably sufficiently high to ensure efficient purging. Typically, the pressure in container 340 is at least 10 bar, or at least 20 bar, or at least 30 bar, or at least 40 bar, or at least 50 bar, e.g., from about 10 bar to about 200 bar.

Containers 326 and 340 are in fluid communication with a multi-port valve 346. In the schematic illustration of FIG. 1, which is not to be considered as limiting, valve 346 is embodied as a three-port valve having a first port, 346a, a second port 346b and a third port 346c. Valve 346 can be of any type, such as, but not limited to, a ball valve, a gate valve, a plunger valve, a butterfly valve or the like. Port 346a is typically in fluid communication with first container 336, port 346b is typically in fluid communication with second container 340, and port 346c is typically in fluid communication with applicator 328. In various exemplary embodiments of the invention the fluid communications between container 326 and port 346a, and between container 340 and port 346b are direct, namely that there are gas delivery lines 348 and 350 that respectively connect the containers 326 and 340 with the ports 346a and 346b, and there is no additional elements that interact with the respective gas along these lines. The connection of line 348 and optionally also of line 350 to the respective ports of valve 346 is preferably of the fast connection type.

Valve 346 is switchable between a first state at which port 346a fluidly connects to port 346c, and a second state at which port 346b fluidly connects to port 346c. During administration, valve 46 assumes the first state, and the gas flow from container 326 to the applicator 28 and into the tissue 322. Between administrations, more preferably before and after each administration, applicator 328 and optionally and preferably also container 326 are removed from system 320, and a purge step is executed by switching valve 346 to its second state, allowing the purging gas to enter the other components of system 320. The purging using the purging gas can contain one or several pressurizing and depressurizing cycles. The purging can, in some embodiments of the present invention, employ vacuum, as further detailed hereinbelow.

System 320 optionally and preferably also comprises a flow control system 352 for controlling the flow of gas exiting port 346c of valve 346. The gas is delivered to flow control system by a gas flow line shown 380b. Flow control system 352 is typically operated during treatment session and is switched off during the purge steps, but operating control system 352 during the purge steps is also contemplated. In embodiments, the flow control system 352 is configured, to deliver the gas for a time period of from about 1 second to about 60 minutes. In embodiments, flow control system 352 is configured to deliver a predetermined amount (volume and/or mass) of gas. In embodiments, flow control system 352 is configured to apply treatment in cycles. For example, flow control system 352 can pause the delivery after a predetermined amount of time and/or after a predetermined amount (volume and/or mass) of the gas has been delivered, and then, after a predetermined time interval, resume the delivery.

In some embodiments of the present invention flow control system 352 comprises an orifice 359 controlled by a valve 358, such as, but not limited to, an on/off valve, which in some embodiments of the present invention can be a solenoid valve.

In some embodiments of the present invention flow control system 352 comprises a flow controller 354 and a flow limiter 356. The gas flow from flow limiter 356 to flow controller 354 via a gas flow line shown at 380c.

Flow limiter 356 serves for limiting the flow rate (typically the volumetric flow rate) of the gas before entering flow controller 354. For example, flow limiter 356 can be an analogue flow controller, equipped with a knob (not shown) for setting an upper limit on the flow rate of the gas passing through limiter 356. The flow limiter can in some embodiments of the present invention include an orifice of a diameter selected to limit the maximum flow, thus serving as a flow restrictor. Typically, flow limiter 356 limit the gas flow rate to a value of from about 0.01 liters per minute (LPM) to about 0.15 LPM, more preferably from about 0.011 liters per minute (LPM) to about 0.11 LPM. Suitable devices for use as flow limiter 356 include the analogue flow controller VAF-G2-01L series, and the flow restrictor 6LV-4-VCR-6-DM series, both commercially available from Swagelok, USA.

Flow controller 354 is optionally and preferably a digital flow controller, more preferably a Proportional-Derivative (PD) controller or a Proportional-Integral-Derivative (PID) controller, configured for controlling the flow through controller 354 in closed loop. The closed loop control of controller 354 can be according to tuning coefficients. Specifically, controller 354 receives, as input, a value of the flow rate, and repeatedly measures the flow rate at its outlet 356. Controller 354 calculates the difference between the measured value of the flow rate and the input value of the flow rate, and then calculates a control signal using the calculated difference. The control signal is used by controller 354 to operate a valve 358 at its outlet 356. The control signal is optionally and preferably calculated as a weighted sum of the calculated difference, the time-derivative of the calculated difference, and optionally also the time-integral of the calculated difference. The weight of the calculated difference in the control signal is referred to as a proportional tuning coefficient, the weight of the time-derivative of the calculated difference in the control signal is referred to as the pseudo-derivative tuning coefficient and, the weight of the time-integral (when computed) of the calculated difference in the control signal is referred to as the integral tuning coefficient.

In some embodiments of the present invention the value of the proportional tuning coefficient is higher for lower input flow rates than for higher input flow rates, and in some embodiments of the present invention the value of the differential tuning coefficient is lower for lower input flow rates than for higher low input flow rates. Representative preferred ranges for the proportional (P) and pseudo-derivative (D) tuning coefficients, for several input flow rates are provided in Table A, below.

TABLE A

| Input flow rate [LPM] | P | D [minute$^{-1}$] |
|---|---|---|
| 0.05 | 2000-3000 | 200-250 |
| 0.25 | 500-1000 | 300-400 |
| 0.5 | 300-500 | 400-600 |
| 0.75 | 250-350 | 500-700 |

In some embodiments of the present invention system 320 comprises a computerized controller 360 having a circuit configured to automatically control flow control system 352. For clarity of presentation, control lines from and to computerized controller 360 are not illustrated. In some embodiments of the present invention computerized controller 360 is at the treatment room (the same room with the applicator 328). More preferably computerized controller 360 is outside the treatment room (controller 360 and applicator are at different rooms). The advantage of this embodiment, is that it reduces the risk of exposure to the gas by the medical practitioner accessing and/or operating computerized controller 360.

Computerized controller 360 controls flow control system 352 according to a predetermined gas flow rate, and/or a predetermined total amount of the gas flowing through system 352, and/or a predetermined total amount of time in which the gas flows through system 352. Computerized controller 360 can comprise a dedicated circuitry and/or a general purpose computer, configured for receiving data and executing the operations described below. Computerized controller 360 can also include a user interface 362 for receiving input from the operator. For example, controller 360 can receive via user interface 362 an input flow rate of the gas, and automatically select the tuning coefficients (e.g., according to Table A, above, or according to any other scenario).

Controller 360 can also receive via user interface 362 an input dose of the gas to be delivered to the subject 324 and transmits a control signal to flow control system 352 to ensure that the total amount of delivered gas does not exceeds the input dose. For example, controller 360 can receive from the digital flow controller 354 a monitoring signal pertaining to the amount of gas that exits outlet 356 and transmit a stop signal to system 352 once the amount of gas has reached the dose. In some optional embodiments of the invention computerized controller 60 also controls one or more of valves 346 and 338, to ensure that the amount of gas delivered does not exceeds the input dose.

In some embodiments of the present invention system 320 comprises a suctioning device 364 arranged to apply suction at a vicinity of the distal end 330 of applicator 328 to withdraw excess gas exiting distal end 330. The suctioning of the gas can be done in a pulsed or continuous manner. Device 364 preferably has an adjustable arm 366 having a suction inlet 368 at its end. The length and/or orientation of arm 66 can be adjusted by the medical partitioned before beginning the treatment session such that the suction inlet 68 is at close proximity to the distal end 330 of applicator 368. In use, excess gas that does not enter tissue 322 is sucked into suction inlet 368 instead of being released to the environment. The withdrawn gas that enters the suction inlet 368 is optionally and preferably passed through a filter 365 selected to remove hazardous gas components such as gNO and NO$_2$. For example, filter 365 can be a Sodalime or alkaline activated carbon filter. Typically, a gas flow line (not shown) is mounted on or embedded in arm 366. Filter 365 can be installed in device 364, as illustrated in FIG. 39, or alternatively at a location along the gas flow line mounted on or embedded in arm 366. The gas withdrawn by device 364 can be evacuated to the medical center pipe (not shown).

In some embodiments of the present invention computerized controller 360 is configured also to control suctioning device 364. In these embodiments computerized controller 360 activates device 364 before the beginning of the treatment session, and deactivates it after the end of the treatment session.

It is to be understood that while FIG. 39 illustrates a single suction inlet 368, the present embodiments contemplate a plurality of suction inlets. For example, device 364 can include multiple suction inlets. Alternatively or additionally, system 320 can include a plurality of suctioning devices, each comprising one or more suction inlets.

In some embodiments of the present invention system 320 comprises an adjustable pressure regulator 370, in fluid communication with port 346c of valve 346. The gas flows from port 346c to regulator 370 via a gas flow line shown at 380a. Pressure regulator 370 is preferably configured for maintaining a pressure which is below a predetermined threshold when valve 346 assumes its first state (treatment session), and a pressure which is above the predetermined threshold when valve 346 assumes its second state (between treatment sessions). A typical pressure threshold employed by pressure regulator 370 is, without limitation from about 2 bars to about 5 bars. Pressure regulator 370 typically includes one or more pressure gauge devices (not shown) for providing indication regarding the gas pressure downstream and/or upstream the regulator 370.

System 320 is typically installed in a treatment room. Optionally, but not necessarily, the treatment room is sealed to the environment so as to ensure that the gas (e.g., gNO) does not leak out of the room. In various exemplary embodiments of the invention system 320 comprises an arrangement of sensors 732 distributed in the treatment room for sensing the gas. Sensors 372 are optionally and preferably configured for generating an alert signal when the level of the gas is above a respective predetermined threshold. In some embodiments of the present invention, the arraignment also include sensors 374 configured for sensing one or more reaction products of the gas. Sensors 374 are optionally and preferably configured for generating an alert signal when the level of the reaction product is above a respective predetermined threshold, which may be the same as the aforementioned threshold. For example, when the gas is gNO, sensors 374 can be configured for sensing NO$_2$, which is the reaction product of gNO with oxygen. The vertical locations of sensors 372 and 374 can be selected based on the specific density of the gas and reaction product to be sensed. For example, when sensors 372 sense gNO and sensors 374 sense $NO_2$, sensors 372 can be distributed at the upper part of the room, and when sensors 374 sense $NO_2$, sensors 374 can be distributed at the lower part of the room.

The predetermined threshold can be, for example, a value from about 25 ppm to about 100 ppm. Suitable sensors for sensing gNO are commercially available from, for example, Honeywell analytics, United Kingdom, and WatchGas, The Netherlands.

In some embodiments of the present invention computerized controller 360 receives sensing signals from sensors 372 and/or 374 issues an alert signal when the level of the gas (e.g., gNO) and/or reaction product (e.g., $NO_2$) is above the respective predetermined threshold.

Figure 40:
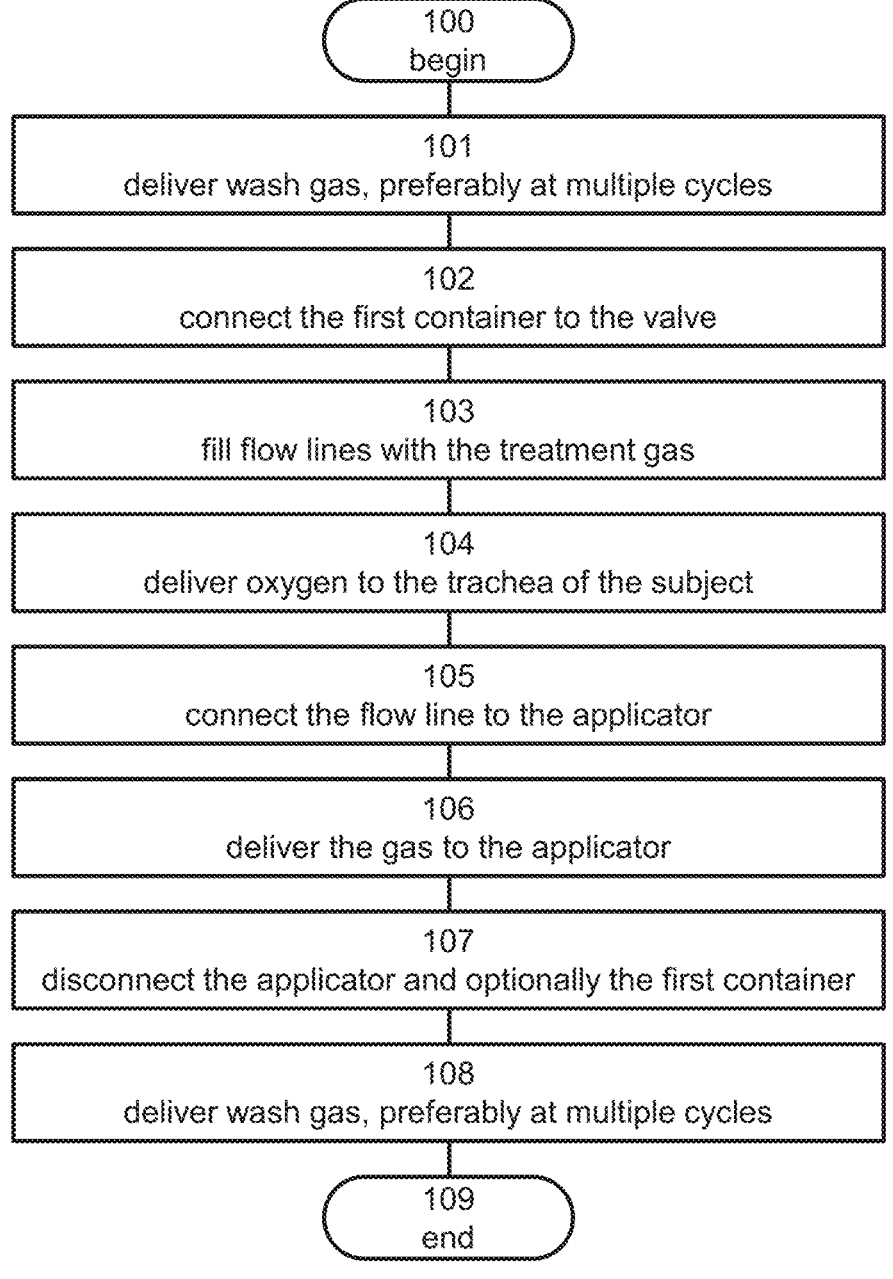
FIG. 40 is a flowchart diagram illustrating a method suitable for delivery of a gas to a tissue, according to some embodiments of the present invention.

FIG. 40 is a flowchart diagram illustrating a method suitable for delivery of a gas to a tissue, according to some embodiments of the present invention. The method is executed using system 320.

The method begins at 100 and optionally and preferably continues to 101 at which the valve 346 is switched to second state to perform purging in which the various components and gas flow lines of the system (e.g., system 352, regulator 370, and gas flow lines 380a, 380b, 80c, 380d) are washed so as to purging gas remnants and other substances (e.g., oxygen) that can react with the gas. Preferably, the purging is for a predetermined time period, e.g., at least 1 minute for at least 3 times. In some embodiments of the present invention the purging includes multiple (e.g., 3 or more) pressurize and depressurize cycles, followed by continuous flow of the purging gas. The Inventors found that such a protocol speeds up the purge and ensures that gas remnants and other substances are more effectively purged out, even from dead ended gas pathways and corners. In some embodiments of the present invention the depressurizing parts of the cycles includes application of vacuum to the gas flow lines. This can be done, for example, by temporarily connecting one of the ports of valve 346 to a vacuum source (not shown). Alternatively, valve 346 can include an additional port (e.g., a fourth port, in which case valve 346 can be a four-port valve) to which the vacuum source is connected, and the depressurizing parts of the cycles can include switching the valve to a state in which the fourth port connects to the third port 346c.

In some embodiments of the present invention a gas leak detection solution is applied to connections through which gas is to be delivered for visual inspection of leakage by formation of bubbles.

The method optionally and preferably continues to 102 at which the first container 326 is connected to valve 346. If the first container 326 is already connected to valve 346, operation 102 can be skipped.

The method optionally and preferably continues to 102 at which the gas flow lines are filled with the gas (e.g., gNO). Preferably, this operation is executed before connecting gas flow line 380d to applicator 328, and while the end of the gas flow line 380d is positioned at a suction inlet (e.g., of device 364 or a vacuum source), so as to prevent release of the gas to the treating room.

In some embodiments of the present invention operation 103 is executed while monitoring the presence and/or concentration of the gas at the end of line 380d, for example, by a sensor, such as one of sensors 372, placed in proximity to the end of line 380d. In these embodiments, the delivery is terminated once the presence of the gas is detected and/or once the monitored concentration is above a predetermined threshold.

The method optionally and preferably continues to 104 at which oxygen or air or oxygen-enriched air is delivered to the subject, e.g., to subject's trachea, for example, by means of an oxygen mask 376 (see FIG. 39) placed on the subject's nose and/or mouth. In some embodiments of the present invention the medical practitioner preparing the subject for treatment and/or performing the treatment also wears a mask such as mask 376. The method continues to $10^5$ at which the flow line 380d is connected to applicator 328. This is optionally and preferably executed after the applicator is already secured to a location near the tissue 322 and the needle 334 or sprayer already engages the tissue 322. At 106 valve 346 is again switched to its first state thereby delivering the gas to the tissue.

The method optionally and preferably proceeds to 107 at which the applicator 328 and optionally and preferably also the first container 326 are disconnected, and to 108 at which valve 346 is switched again to the second state to perform purging in which, the various components and gas flow lines of the system are washed so as to purging gas remnants and other substances (e.g., oxygen) that can react with the gas. Preferably, this operation is executed as described above with respect to operation 101. In some embodiments of the present invention at least one of operations 101 and 107 is executed while monitoring the presence and/or concentration of the gas at the end of line 380d, as further detailed hereinabove. In these embodiments, the delivery is terminated once the monitored concentration is zero or below a predetermined threshold.

The method ends at 109.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of inhibiting growth of cells or tissue of a primary and/or secondary tumor in a subject in need thereof, the method comprising locally administering to the tumor gaseous nitric oxide (gNO) at a dose of from about 1,000 ppm to about 1,000,000 ppm for a time period of from about 1 second to about 60 minutes at a volumetric flow of from about 0.00001 LPM to about 1 LPM, wherein locally administering said gNO is by intratumoral injection.

2. The method according to claim 1, wherein the gNO is administered at a dose of from about 20,000 ppm to about 200,000 ppm or from about 20,000 ppm to about 50,000 ppm.

3. The method according to claim 1, wherein the gNO is administered for a time period that ranges from about 30 seconds to about 10 minutes.

4. The method according to claim 1, wherein the gNO is administered at a volumetric flow of from about 0.001 LPM to about 0.5 LPM.

5. The method according to claim 1, wherein the gNO is administered at two or more administration sites in the tumor.

6. The method according to claim 5, wherein the distance between the two or more administration sites is, independently, from about 2.5 mm to about 1 cm, or from about 0.25 cm to about 0.5 cm.

7. The method according to claim 1, wherein the gNO is administered at a dose of from about 0.1 mg to about 300 mg, per $cm^3$ tumor.

8. The method according to claim 1, wherein gNO is administered at a dose of from about 0.01 mg to about 100 mg, or from 0.1 mg to about 10 mg, per a tumor of 20 $mm^3$ or less.

9. The method according claim 1, further comprising scavenging excess gNO from the administration site.

10. The method according to claim 1, wherein locally administering said gNO is pulsed from about 2 to about 20 times.

11. The method according to claim 1, wherein locally administering said gNO to the subject is performed at least once.

12. The method according to claim 1, wherein locally administering said gNO to the subject is performed at least twice, and wherein a time interval between said two administrations is at least one week.

13. The method according to claim 1, further comprising co-administering to the subject an anti-cancer therapy.

14. The method according to claim 1, being for inhibiting growth and/or killing cells of a primary tumor.

15. The method according to claim 1, being for preventing occurrence, inhibiting growth and/or killing cells of a secondary tumor.

16. The method according to claim 1, wherein said secondary tumor comprises metastasizing tumor and/or a recurrent tumor.

17. The method according to claim 1, being for stimulating in the subject an immunological response to the tumor, thereby inhibiting growth of a primary tumor and/or a secondary tumor.

\* \* \* \* \*